(12) United States Patent
Bogaert et al.

(10) Patent No.: US 8,772,254 B2
(45) Date of Patent: Jul. 8, 2014

(54) METHOD AND CONSTRUCTS FOR DELIVERING DOUBLE STRANDED RNA TO PEST ORGANISMS

(75) Inventors: Thierry AndréOlivier Eddy Bogaert, Kortrijk (BE); Richard Zwaal, Gent (BE); Geert Karel Maria Plaetinck, Merelbeke-Bottelare (BE); Jan Octaaf De Kerpel, Lede (BE); Titus Jan Kaletta, Merelbeke (BE)

(73) Assignee: Devgen N.V., Zwijnaarde (BE)

( * ) Notice: Subject to any disclaimer, the term of this patent is extended or adjusted under 35 U.S.C. 154(b) by 1027 days.

(21) Appl. No.: 11/666,017

(22) PCT Filed: Oct. 25, 2005

(86) PCT No.: PCT/EP2005/011441
§ 371 (c)(1),
(2), (4) Date: Apr. 23, 2007

(87) PCT Pub. No.: WO2006/045591
PCT Pub. Date: May 4, 2006

(65) Prior Publication Data
US 2009/0263364 A1    Oct. 22, 2009

Related U.S. Application Data

(60) Provisional application No. 60/621,718, filed on Oct. 25, 2004, provisional application No. 60/628,976, filed on Nov. 18, 2004.

(30) Foreign Application Priority Data

Oct. 25, 2004    (EP) ..................................... 04447234
Nov. 18, 2004    (EP) ..................................... 04447252

(51) Int. Cl.
*C12N 15/11*    (2006.01)
*C07H 21/04*    (2006.01)

(52) U.S. Cl.
USPC ........................................ 514/44 A; 536/24.5

(58) Field of Classification Search
USPC ................ 435/91.1, 91.31, 455; 514/1, 2, 44; 536/23.1, 24.5, 23, 4
See application file for complete search history.

(56) References Cited

U.S. PATENT DOCUMENTS

| 6,506,559 | B1 * | 1/2003 | Fire et al. ........................... 435/6 |
| 6,586,240 | B1 | 7/2003 | Singer et al. |
| 6,884,878 | B2 * | 4/2005 | Borovsky et al. ............. 536/23.5 |
| 6,903,077 | B1 * | 6/2005 | Heintz .......................... 514/44 R |
| 7,786,290 | B2 * | 8/2010 | Woppmann et al. .......... 536/24.5 |
| 2001/0014469 | A1 * | 8/2001 | Wilcox et al. .................. 435/183 |
| 2002/0192689 | A1 * | 12/2002 | Pasloske et al. .................... 435/6 |
| 2003/0140371 | A1 * | 7/2003 | Stevens et al. ................. 800/279 |
| 2003/0150017 | A1 * | 8/2003 | Mesa et al. ..................... 800/279 |
| 2003/0224444 | A1 * | 12/2003 | Sabbadini et al. ............. 435/7.1 |
| 2004/0019188 | A1 * | 1/2004 | Scholte ........................ 530/391.1 |
| 2010/0031396 | A1 * | 2/2010 | Mirkov et al. ................ 800/294 |
| 2010/0098680 | A1 * | 4/2010 | Rider ............................ 424/94.5 |
| 2010/0267572 | A1 * | 10/2010 | Bulyk et al. ....................... 506/7 |

FOREIGN PATENT DOCUMENTS

| DE | 101 62 867 A1 |   | 7/2004 |
| WO | WO 00/01846 A |   | 1/2000 |
| WO | WO 0001846 | * | 1/2000 |
| WO | WO 2004/005485 A |   | 1/2004 |
| WO | WO 2004/081533 | * | 9/2004 |
| WO | WO 2004/081533 A |   | 9/2004 |

OTHER PUBLICATIONS

Uherek, et al. (Adv. Drug. Del., Rev., v.44:153-66) (2000) "DNA-carrier proteins for targeted gene delivery". pp. 153-166.*
Fitches, et al. (J. Insect Phys., v.50:61-71) (2004) "Fusion proteins containing insect-specific toxins as pest control agents: snowdrop lectin delivers fused insecticidal spider venom toxin to insect haemolymph following oral injestion".*
Bass, B.L., "Double-stranded RNA as a template for gene silencing," *Cell* Apr. 28, 2000; 101(3): 235-238.
Bettinger, T. et al., "Peptide-mediated RNA delivery: A novel approach for enhanced transfection of primary and post-mitotic cells," *Nucleic Acids Research* Sep. 15, 2001; 29(18): 3882-3891.
Entelis, N.S. et al., "RNA delivery into mitochondria," *Advanced Drug Delivery Reviews* Jul. 2, 2001; 49(1-2): 199-215.
McCarter, J.P., "Genomic filtering: an approach to discovering novel antiparasitics," *Trends in Parasitology* Oct. 2004; 20(10): 462-468.
Vance, V. et al., "RNA silencing in plants: Defense and counterdefense," *Science* Jun. 22, 2001; 292(5525): 2277-2280.

* cited by examiner

*Primary Examiner* — Jennifer Pitrak McDonald

(57) ABSTRACT

The present invention relates in generally to RNAi and its use in gene silencing. In particular, the present invention relates to methods and constructs for delivering double stranded RNA (dsRNA) to pest organisms.

4 Claims, 21 Drawing Sheets

Figure 1: nucleotide sequence of the coliphage HK022 Nun gene (SEQ ID NO 1)
atgcttatggtgaaaaagactatttatgttaatcctgacagcggacaaaacagaaaagtatctgatagaggtcttacatctcga
gacaggaggagaatagcgagatgggaaaaaaggatagcatatgcattaaaaaacggtgtgacacctggatttaatgctat
agatgacggtcctgaatataagattaatgaagacccaatggacaaagttgacaaagcattagcaacaccatttcctcgcgat
gtcgaaaaaattgaagatgaaaaatatgaggatgtaatgcacagagttgttaatcacgctcaccagcgaaacccaaacaa
aaagtggtcataa (SEQ ID NO 1)

Figure 2: amino acid sequence of the coliphage HK022 Nun gene (SEQ ID NO 2)
MLMVKKTIYVNPDSGQNRKVSDRGLTSRDRRRIARWEKRIAYALKNGVTPGFNAIDDGP
EYKINEDPMDKVDKALATPFPRDVEKIEDEKYEDVMHRVVNHAHQRNPNKKWS*
(SEQ ID NO 2)

Figure 3: nucleotide sequence corresponding to the N-terminal domain of the coliphage HK022 Nun protein: nucleic acids 1 to 141 (SEQ ID NO 3)
Atgcttatggtgaaaaagactatttatgttaatcctgacagcggacaaaacagaaaagtatctgatagaggtcttacatctcga
gacaggaggagaatagcgagatgggaaaaaaggatagcatatgcattaaaaaacggt (SEQ ID NO 3)

Figure 4: amino acid sequence corresponding to the N-terminal domain of the coliphage HK022 Nun protein: amino acids 1 to 47 (SEQ ID NO 4)
MLMVKKTIYVNPDSGQNRKVSDRGLTSRDRRRIARWEKRIAYALKNG (SEQ ID NO 4)

Figure 5: nucleotide sequence corresponding to the N-terminal domain of the coliphage HK022 Nun protein: nucleic acids 37 to 141 (SEQ ID NO 5)
gacagcggacaaaacagaaaagtatctgatagaggtcttacatctcgagacaggaggagaatagcgagatgggaaaaa
aggatagcatatgcattaaaaaacggt (SEQ ID NO 5)

Figure 6: amino acid sequence corresponding to the N-terminal domain of the coliphage HK022 Nun protein: amino acids 13 to 47. (SEQ ID NO 6)
DSGQNRKVSDRGLTSRDRRRIARWEKRIAYALKNG (SEQ ID NO 6)

Figure 7: nucleotide sequence corresponding to the N-terminal domain of the coliphage HK022 Nun protein nucleic acids 64 to 141 (SEQ ID NO 7)
gatagaggtcttacatctcgagacaggaggagaatagcgagatgggaaaaaaggatagcatatgcattaaaaaacggt
(SEQ ID NO 7)

Figure 8: amino acid sequence corresponding to the N-terminal domain of the coliphage HK022 Nun protein: amino acids 22 to 47 (SEQ ID NO 8)
DRGLTSRDRRRIARWEKRIAYALKNG (SEQ ID NO 8)

Figure 9: nucleotide sequence of the gene encoding the *Bacillus subtilis* LicT protein (SEQ ID NO 9)
Atgaaaattgcgaaggtgatcaacaataatgtgatcagcgtggtcaatgaacaggggaaagaattggtcgtcatgggcagg
gggctcgcgtttcagaaaaagtccggcgatgatgtcgatgaagcccgcattgagaaagtgttcacgctcgataacaaggatg
tatcagaaaagttcaaaacccttttgtatgatataccgatcgagtgtatggaagtatccgaagagattatcagctacgcaaaatt
acagctcggcaaaaagctcaacgacagcatctatgtgtcgctgaccgaccatattaactttgccatccagcgcaaccagaa
agggcttgatatcaaaaacgccttgctgtgggaaacaaaacggctctacaaagacgaatttgcgatcggcaaagaagcgtt
ggttatggtaaaaaacaagactggtgtgtctctgccagaggatgaagcaggctttattgctctgcatattgtaaatgccgagctg
aatgaagagatgcccaatattatcaacattacaaaagtcatgcaagagattttgagtattgtaaaataccattttaagattgaatt
caacgaagaatcgcttcactattatcggttcgtcacccacttaaagttttcgcgcagcgtctatttaacggcactcacatggaaa
gccaagacgattttttgctggatacagtgaaagaaaagtatcatcgcgcgtatgaatgcacgaagaaaatccaaacctacatt
gagcgggagtatgagcacaagctcacaagtgacgagctgctgtatttaaccattcacatagaaagggtagttaaacaagca
taa (SEQ ID NO 9)

Figure 10: amino acid sequence of the gene encoding the *Bacillus subtilis* LicT protein (SEQ ID NO 10)
MKIAKVINNNVISVVNEQGKELVVMGRGLAFQKKSGDDVDEARIEKVFTLDNKDVSEKFK
TLLYDIPIECMEVSEEIISYAKLQLGKKLNDSIYVSLTDHINFAIQRNQKGLDIKNALLWETK
RLYKDEFAIGKEALVMVKNKTGVSLPEDEAGFIALHIVNAELNEEMPNIINITKVMQEILSIV
KYHFKIEFNEESLHYYRFVTHLKFFAQRLFNGTHMESQDDFLLDTVKEKYHRAYECTKKI
QTYIEREYEHKLTSDELLYLTIHIERVVKQA* (SEQ ID NO 10)

Figure 11: nucleotide sequence corresponding to the N-terminal domain of the *Bacillus subtilis* LicT protein: nucleic acids 1 to 168 (SEQ ID NO 11)
atgaaaattgcgaaggtgatcaacaataatgtgatcagcgtggtcaatgaacaggggaaagaattggtcgtcatgggcagg
gggctcgcgtttcagaaaaagtccggcgatgatgtcgatgaagcccgcattgagaaagtgttcacgctcgataacaaggatg
tatca (SEQ ID NO 11)

Figure 12: amino acid sequence corresponding to the N-terminal domain of the *Bacillus subtilis* LicT protein: amino acids 1 to 56 (SEQ ID NO 12)
MKIAKVINNNVISVVNEQGKELVVMGRGLAFQKKSGDDVDEARIEKVFTLDNKDVS (SEQ ID NO 12)

Figure 13: nucleotide sequence of the gene encoding the bacteriophage MS2 coat protein (SEQ ID NO 13)
Atggcttctaactttactcagttcgttctcgtcgacaatggcggaactggcgacgtgactgtcgccccaagcaacttcgctaacg
gggtcgctgaatggatcagctctaactcgcgttcacaggcttacaaagtaacctgtagcgttcgtcagagctctgcgcagaatc
gcaaatacaccatcaaagtcgaggtgcctaaagtggcaacccagactgttggtggtgtagagcttcctgtagccgcatggcg
ttcgtacttaaatatggaactaaccattccaattttcgctacgaattccgactgcgagcttattgttaaggcaatgcaaggtctcct
aaaagatggaaacccgattccctcagcaatcgcagcaaactccggcatctactaa (SEQ ID NO 13)

Figure 14: amino acid sequence of the gene encoding the bacteriophage MS2 coat protein. (SEQ ID NO 14)
MASNFTQFVLVDNGGTGDVTVAPSNFANGVAEWISSNSRSQAYKVTCSVRQSSAQNRK
YTIKVEVPKVATQTVGGVELPVAAWRSYLNMELTIPIFATNSDCELIVKAMQGLLKDGNPI
PSAIAANSGIY* (SEQ ID NO 14)

Figure 15: boxB RNA sequence (SEQ ID NO 15)
GCCCUGAAAAAGGGC (SEQ ID NO 15)

Figure 16: 11mer of the box B RNA sequence (SEQ ID NO 16)
GCCCUGAAAAA (SEQ ID NO 16)

Figure 17: RNA nucleotide sequence recognized by a protein homologous to the *Bacillus subtilis* LicT protein (family of the LicT/SacY)
GGAUUGUUACUGCGAAAGCAGGCAAAACC (SEQ ID NO 17)

Figure 18: RNA nucleotide sequence recognized by a protein homologous to the *Bacillus subtilis* LicT protein (family of the LicT/SacY)
GGAUUGUUACUGAUAAAGCAGGCAAAACC (SEQ ID NO 18)

Figure 19: RNA nucleotide sequence recognized by a protein homologous to the *Bacillus subtilis* LicT protein (family of the LicT/SacY)
GGUUUGUUACUGAUAAAGCAGGCAAGACC (SEQ ID NO 19)

Figure 20: RNA nucleotide sequence recognized by a protein homologous to the *Bacillus subtilis* LicT protein (family of the LicT/SacY)
GGAUUGUGACUGGUAAAGCAGGCAAGACC (SEQ ID NO 20)

Figure 21: RNA nucleotide sequence recognized by a protein homologous to the *Bacillus subtilis* LicT protein (family of the LicT/SacY)
ACGUGUUACUGAUUCGAUCAGGCAUCAGU (SEQ ID NO 21)

Figure 22: RNA nucleotide sequence recognized by a protein homologous to the *Bacillus subtilis* LicT protein (family of the LicT/SacY)
GGAUUGUUACUGCACAGGCAGGCAAGACC (SEQ ID NO 22)

Figure 23: RNA nucleotide sequence recognized by a protein homologous to the *Bacillus subtilis* LicT protein (family of the LicT/SacY)
GGAAUGUAACUGCACAGGCAGGCAGUACC (SEQ ID NO 23)

Figure 24: RNA nucleotide sequence recognized by a protein homologous to the *Bacillus subtilis* LicT protein (family of the LicT/SacY)
AGAUUGUUACCGAUUCGAUCGGGCAAAACC (SEQ ID NO 24)

Figure 25: RNA nucleotide sequence recognized by a protein homologous to the *Bacillus subtilis* LicT protein (family of the LicT/SacY)
GGAUUGUUACUGAUAAUGCAGGCAAGACC (SEQ ID NO 25)

Figure 26: RNA nucleotide sequence recognized by a protein homologous to the *Bacillus subtilis* LicT protein (family of the LicT/SacY)
ACGUGUAACUAAUUCGAUUAGGCAUGAGU (SEQ ID NO 26)

Figure 27: RNA nucleotide sequence recognized by a protein homologous to the *Bacillus subtilis* LicT protein (family of the LicT/SacY)
GUGAAUGUUAGUAACAUUGAUUACGCAUGAUCAC (SEQ ID NO 27)

Figure 28: RNA nucleotide sequence recognized by a protein homologous to the *Bacillus subtilis* LicT protein (family of the LicT/SacY)
GGAUAGUGAUUAUUAAGUUAAGCUAGACC (SEQ ID NO 28)

Figure 29: RNA nucleotide sequence recognized by a protein homologous to the *Bacillus subtilis* LicT protein (family of the LicT/SacY)
UGUGGAUUGUGACUAUUUAAUUAGGCGAGACCACA (SEQ ID NO 29)

Figure 30: RNA nucleotide sequence recognized by a protein homologous to the *Bacillus subtilis* LicT protein (family of the LicT/SacY)
GGAUUGCGACUGUAUAUCCCUCAGCGGGAAAUACAGGCAAAACC (SEQ ID NO 30)

Figure 31: RNA nucleotide sequence recognized by a protein homologous to the *Bacillus subtilis* LicT protein (family of the LicT/SacY)
GGGUUGCUACUGCCAUUGGCAGGCAAAACC (SEQ ID NO 31)

Figure 32: RNA nucleotide sequence recognized by a protein homologous to the *Bacillus subtilis* LicT protein (family of the LicT/SacY)
GGAUUGUUACCGCACUAAGCGGGCAAAACC (SEQ ID NO 32)

Figure 33: RNA nucleotide sequence recognized by a protein homologous to the *Bacillus subtilis* LicT protein (family of the LicT/SacY)
GGAUUGUUACUGCAUUCGCAGGCAAAACC (SEQ ID NO 33)

Figure 34: The 29-mer sequence recognition pattern on the *B.subtilis* ribonucleic antiterminator (RAT) for binding to LicT; N = A, G, U or C
GGNUUGUNACUGNNNNAGCAGGCAANNCC (SEQ ID NO 34)

Figure 35: An RNA recognition sequence for the bacteriophage MS2 coat protein
ACAUGAGGAUCACCCAUGA (SEQ ID NO 35)

Figure 36: An RNA recognition sequence for the bacteriophage MS2 coat protein
CCACAGUCACAGGG (SEQ ID NO 36)

Figure 37: An RNA recognition sequence for the bacteriophage MS2 coat protein
CCGGAGGAUCACCACGGG (SEQ ID NO 37)

Figure 38: An RNA recognition sequence for the bacteriophage MS2 coat protein
CCGGAGGAUCACCACGGG (SEQ ID NO 38)

Figure 39: An RNA recognition sequence for the bacteriophage MS2 coat protein
UCGCCAACAGGCGG (SEQ ID NO 39)

Figure 40: A 19-mer sequence recognition pattern for binding to the bacteriophage MS2 coat protein, wherein $N_1$-$N_5$ are the reverse complementary of $N_{15}$-$N_{19}$ and $N_7$-$N_8$ are the reverse complementary of $N_{13}$-$N_{14}$
$N_1N_2N_3N_4N_5PuN_7N_8AN_{10}PyAN_{13}N_{14}N_{15}N_{16}N_{17}N_{18}N_{19}$ (SEQ ID NO 40)

Figure 43: *Meloidogyne incognita* tubulin with LicT recognition sequence (bold and underlined)

CGGACCGCATTACGTCTTCCTTCTCTGTTGTTCCGTCGCCTAAGGTCTCTGACACGG
TCGTTGAGCCCTACAACGCAACTCTTTCTGTTCATCAACTTGTTGAGAACACCGACGA
GACTTACTGCATCGGGATTGTTACTGCGAAAGCAGGCAAAACCCGATGCAGTAAGT
CTCGTCGGTGTTCTCAACAAGTTGATGAACAGAAAGAGTTGCGTTGTAGGGCTCAAC
GACCGTGTCAGAGACCTTAGGCGACGGAACAACAGAGAAGGAAGACGTAATGCGGT
CCGGATACTCCTCACGAATCTTTGAAATGAGCAAAGTTCCCATTCCAGAGCCAGTTC
CACCACCAAGCGAGTGAGTCAATTGAAAACCTTGAAGACAATCACAACCCTCAGCCT
CTTTTCGAACAACATCCAGGATTGTTACTGCGAAAGCAGGCAAAACCTGGATGTTGT
TCGAAAAGAGGCTGAGGGTTGTGATTGTCTTCAAGGTTTTCAATTGACTCACTCGCTT
GGTGGTGGAACTGGCTCTGGAATGGGAACTTTGCTCATTTCAAAGATTCGTGAGGAG
TATC (SEQ ID NO 41)

Figure 44: *Caenorhabditis elegans* tubulin with LicT recognition sequence (bold and underlined)
CAGACAGAATCATGAGCTCATTCTCGGTTGTACCATCGCCAAAGGTGTCCGACACAG
TTGTAGAACCATACAATGCCACCCTCTCCGTCCACCAGCTTGTTGAGAACACCGATG
AGACCTACTGCATT<u>GGATTGTTACTGCGAAAGCAGGCAAAACC</u>AATGCAGTAGGTC
TCATCGGTGTTCTCAACAAGCTGGTGGACGGAGAGGGTGGCATTGTATGGTTCTACA
ACTGTGTCGGACACCTTTGGCGATGGTACAACCGAGAATGAGCTCATGATTCTGTCT
GGGTACTCTTCGCGGATTTTGGAGATGAGAAGTGTTCCCATTCCAGATCCGGTTCCT
CCTCCGAGAGAGTGAGTGAGTTGGAATCCTTGAAGACAATCGCATCCTTCGGCTTCC
TTGCGGATCACGTC<u>GGATTGTTACTGCGAAAGCAGGCAAAACC</u>GACGTGATCCGCA
AGGAAGCCGAAGGATGCGATTGTCTTCAAGGATTCCAACTCACTCACTCTCTCGGAG
GAGGAACCGGATCTGGAATGGGAACACTTCTCATCTCCAAAATCCGCGAAGAGTACC
(SEQ ID NO 42)

Figure 45: *Magnaporthe grisea* tubulin with LicT recognition sequence (bold and underlined)
TACCCAGAATGCCGGAGACGTCGTCGTCCATCCCTACAACAGCATCCTAGCCATGAG
GAGATTGACACAGAATGCCGACTCGGTGGTGGTGCTGGATAACGGCGCTCTCTCAC
ATATTGCAGCCGATAGACTCCACGTGCAAGAGCCGTCTTTTCAGCAGACAAATCAAC
TG<u>GGATTGTTACTGCGAAAGCAGGCAAAACC</u>CAGTTGATTTGTCTGCTGAAAAGAC
GGCTCTTGCACGTGGAGTCTATCGGCTGCAATATGTGAGAGAGCGCCGTTATCCAG
CACCACCACCGAGTCGGCATTCTGTGTCAATCTCCTCATGGCTAGGATGCTGTTGTA
GGGATGGACGACGACGTCTCCGGCATTCTGGGTATCCGGAAATACCGAATACGTTT
GTATGATCTTCTTGGGAAATCGGTCATTTAGCCTTTCCAAGAGGAATGAGCCCAGAC
CTGAGCCTGTGCCACCAGCAATCGAATGCAGCATCATAAAGCCCTCGAGTGAGTCG
CTTCCATCTGCTTCCCTATCAATCATCTCCATAATG<u>GGATTGTTACTGCGAAAGCAG</u>
<u>GCAAAACC</u>CATTATGGAGATGATTGATAGGGAAGCAGATGGAAGCGACTCACTCGA
GGGCTTTATGATGCTGCATTCGATTGCTGGTGGCACAGGCTCAGGTCTGGGCTCATT
CCTCTTGGAAAGGCTAAATGACCGATTTCCCAAGAAGATCATACAAACGTATTCGGTA
TTTCCGGA (SEQ ID NO 43)

Figure 46: *Nilaparvata lugens* tubulin with LicT recognition sequence (bold and underlined)
CAGACAGAATCATGAACACCTACTCCGTTGTGCCCTCACCAAAGGTATCCGACACAG
TTGTCGAGCCATACAATGCCACCCTCTCCGTTCATCAGCTCGTCGAAAACACCGATG
AAACCTACTGTATCG<u>GGATTGTTACTGCGAAAGCAGGCAAAACC</u>CGATACAGTAGG
TTTCATCGGTGTTTTCGACGAGCTGATGAACGGAGAGGGTGGCATTGTATGGCTCGA
CAACTGTGTCGGATACCTTTGGTGAGGGCACAACGGAGTAGGTGTTCATGATTCTGT
CTGGGTATTCCTCGCGGATTTTCGAGATCAGCAATGTTCCCATTCCTGATCCGGTAC
CACCTCCCAACGAATGAGTCAGCTGGAATCCCTGTAAGCAATCGCAGCTCTCGGCTT
CCTTTCTGACTACGTCGA<u>GGATTGTTACTGCGAAAGCAGGCAAAACC</u>TCGACGTAG
TCAGAAAGGAAGCCGAGAGCTGCGATTGCTTACAGGGATTCCAGCTGACTCATTCGT
TGGGAGGTGGTACCGGATCAGGAATGGGAACATTGCTGATCTCGAAAATCCGCGAG
GAATACC (SEQ ID NO 44)

Figure 47: *Meloidogyne incognita* tubulin with Nun recognition sequence (bold and underlined)
CGGACCGCATTACGTCTTCCTTCTCTGTTGTTCCGTCGCCTAAGGTCTCTGACACGG
TCGTTGAGCCCTACAACGCAACTCTTTCTGTTCATCAACTTGTTGAGAACACCGACGA
GACTTACTGCATCGGCCCTGAAAAAGGGCCGATGCAGTAAGTCTCGTCGGTGTTCT
CAACAAGTTGATGAACAGAAAGAGTTGCGTTGTAGGGCTCAACGACCGTGTCAGAGA
CCTTAGGCGACGGAACAACAGAGAAGGAAGACGTAATGCGGTCCGGATACTCCTCA
CGAATCTTTGAAATGAGCAAAGTTCCCATTCCAGAGCCAGTTCCACCACCAAGCGAG
TGAGTCAATTGAAAACCTTGAAGACAATCACAACCCTCAGCCTCTTTTCGAACAACAT
CCAGCCCTGAAAAAGGGCTGGATGTTGTTCGAAAAGAGGCTGAGGGTTGTGATTGT
CTTCAAGGTTTTCAATTGACTCACTCGCTTGGTGGTGGAACTGGCTCTGGAATGGGA
ACTTTGCTCATTTCAAAGATTCGTGAGGAGTATC (SEQ ID NO 45)

Figure 48: *Caenorhabditis elegans* tubulin with Nun recognition sequence (bold and underlined)
CAGACAGAATCATGAGCTCATTCTCGGTTGTACCATCGCCAAAGGTGTCCGACACAG
TTGTAGAACCATACAATGCCACCCTCTCCGTCCACCAGCTTGTTGAGAACACCGATG
AGACCTACTGCATTGCCCTGAAAAAGGGCAATGCAGTAGGTCTCATCGGTGTTCTCA
ACAAGCTGGTGGACGGAGAGGGTGGCATTGTATGGTTCTACAACTGTGTCGGACAC
CTTTGGCGATGGTACAACCGAGAATGAGCTCATGATTCTGTCTGGGTACTCTTCGCG
GATTTTGGAGATGAGAAGTGTTCCCATTCCAGATCCGGTTCCTCCTCCGAGAGAGTG
AGTGAGTTGGAATCCTTGAAGACAATCGCATCCTTCGGCTTCCTTGCGGATCACGTC
GCCCTGAAAAAGGGCGACGTGATCCGCAAGGAAGCCGAAGGATGCGATTGTCTTCA
AGGATTCCAACTCACTCACTCTCTCGGAGGAGGAACCGGATCTGGAATGGGAACACT
TCTCATCTCCAAAATCCGCGAAGAGTACC (SEQ ID NO 46)

Figure 49: *Magnaporthe grisea* tubulin with Nun recognition sequence (bold and underlined)
TACCCAGAATGCCGGAGACGTCGTCGTCCATCCCTACAACAGCATCCTAGCCATGAG
GAGATTGACACAGAATGCCGACTCGGTGGTGGTGCTGGATAACGGCGCTCTCTCAC
ATATTGCAGCCGATAGACTCCACGTGCAAGAGCCGTCTTTTCAGCAGACAAATCAAC
TGGCCCTGAAAAAGGGCCAGTTGATTTGTCTGCTGAAAAGACGGCTCTTGCACGTG
GAGTCTATCGGCTGCAATATGTGAGAGAGCGCCGTTATCCAGCACCACCACCGAGT
CGGCATTCTGTGTCAATCTCCTCATGGCTAGGATGCTGTTGTAGGGATGGACGACGA
CGTCTCCGGCATTCTGGGTATCCGGAAATACCGAATACGTTTGTATGATCTTCTTGG
GAAATCGGTCATTTAGCCTTTCCAAGAGGAATGAGCCCAGACCTGAGCCTGTGCCAC
CAGCAATCGAATGCAGCATCATAAAGCCCTCGAGTGAGTCGCTTCCATCTGCTTCCC
TATCAATCATCTCCATAATGGCCCTGAAAAAGGGCCATTATGGAGATGATTGATAGG
GAAGCAGATGGAAGCGACTCACTCGAGGGCTTTATGATGCTGCATTCGATTGCTGGT
GGCACAGGCTCAGGTCTGGGCTCATTCCTCTTGGAAAGGCTAAATGACCGATTTCCC
AAGAAGATCATACAAACGTATTCGGTATTTCCGGA (SEQ ID NO 47)

Figure 50: *Nilaparvata lugens* tubulin with Nun recognition sequence (bold and underlined)
CAGACAGAATCATGAACACCTACTCCGTTGTGCCCTCACCAAAGGTATCCGACACAG
TTGTCGAGCCATACAATGCCACCCTCTCCGTTCATCAGCTCGTCGAAAACACCGATG
AAACCTACTGTATCGGCCCTGAAAAAGGGCCGATACAGTAGGTTTCATCGGTGTTTT
CGACGAGCTGATGAACGGAGAGGGTGGCATTGTATGGCTCGACAACTGTGTCGGAT
ACCTTTGGTGAGGGCACAACGGAGTAGGTGTTCATGATTCTGTCTGGGTATTCCTCG
CGGATTTTCGAGATCAGCAATGTTCCCATTCCTGATCCGGTACCACCTCCCAACGAA
TGAGTCAGCTGGAATCCCTGTAAGCAATCGCAGCTCTCGGCTTCCTTTCTGACTACG
TCGAGCCCTGAAAAAGGGCTCGACGTAGTCAGAAAGGAAGCCGAGAGCTGCGATTG
CTTACAGGGATTCCAGCTGACTCATTCGTTGGGAGGTGGTACCGGATCAGGAATGG
GAACATTGCTGATCTCGAAAATCCGCGAGGAATACC (SEQ ID NO 48)

Figure 51: *Meloidogyne incognita* tubulin with MS2 recognition sequence (bold and underlined)
CGGACCGCATTACGTCTTCCTTCTCTGTTGTTCCGTCGCCTAAGGTCTCTGACACGG
TCGTTGAGCCCTACAACGCAACTCTTTCTGTTCATCAACTTGTTGAGAACACCGACGA
GACTTACTGCATCGACATGAGGATCACCCATGACGATGCAGTAAGTCTCGTCGGTG
TTCTCAACAAGTTGATGAACAGAAAGAGTTGCGTTGTAGGGCTCAACGACCGTGTCA
GAGACCTTAGGCGACGGAACAACAGAGAAGGAAGACGTAATGCGGTCCGGATACTC
CTCACGAATCTTTGAAATGAGCAAAGTTCCCATTCCAGAGCCAGTTCCACCACCAAG
CGAGTGAGTCAATTGAAAACCTTGAAGACAATCACAACCCTCAGCCTCTTTTCGAACA
ACATCCAACATGAGGATCACCCATGATGGATGTTGTTCGAAAAGAGGCTGAGGGTT
GTGATTGTCTTCAAGGTTTTCAATTGACTCACTCGCTTGGTGGTGGAACTGGCTCTG
GAATGGGAACTTTGCTCATTTCAAAGATTCGTGAGGAGTATC (SEQ ID NO 49)

Figure 52: *Caenorhabditis elegans* tubulin with MS2 recognition sequence (bold and underlined)
CAGACAGAATCATGAGCTCATTCTCGGTTGTACCATCGCCAAAGGTGTCCGACACAG
TTGTAGAACCATACAATGCCACCCTCTCCGTCCACCAGCTTGTTGAGAACACCGATG
AGACCTACTGCATTACATGAGGATCACCCATGAAATGCAGTAGGTCTCATCGGTGTT
CTCAACAAGCTGGTGGACGGAGAGGGTGGCATTGTATGGTTCTACAACTGTGTCGG
ACACCTTTGGCGATGGTACAACCGAGAATGAGCTCATGATTCTGTCTGGGTACTCTT
CGCGGATTTTGGAGATGAGAAGTGTTCCCATTCCAGATCCGGTTCCTCCTCCGAGAG
AGTGAGTGAGTTGGAATCCTTGAAGACAATCGCATCCTTCGGCTTCCTTGCGGATCA
CGTCACATGAGGATCACCCATGAGACGTGATCCGCAAGGAAGCCGAAGGATGCGAT
TGTCTTCAAGGATTCCAACTCACTCACTCTCTCGGAGGAGGAACCGGATCTGGAATG
GGAACACTTCTCATCTCCAAAATCCGCGAAGAGTACC (SEQ ID NO 50)

Figure 53: *Magnaporthe grisea* tubulin with MS2 recognition sequence (bold and underlined)
TACCCAGAATGCCGGAGACGTCGTCGTCCATCCCTACAACAGCATCCTAGCCATGAG
GAGATTGACACAGAATGCCGACTCGGTGGTGGTGCTGGATAACGGCGCTCTCTCAC
ATATTGCAGCCGATAGACTCCACGTGCAAGAGCCGTCTTTTCAGCAGACAAATCAAC
TGACATGAGGATCACCCATGACAGTTGATTTGTCTGCTGAAAAGACGGCTCTTGCAC
GTGGAGTCTATCGGCTGCAATATGTGAGAGAGCGCCGTTATCCAGCACCACCACCG
AGTCGGCATTCTGTGTCAATCTCCTCATGGCTAGGATGCTGTTGTAGGGATGGACGA
CGACGTCTCCGGCATTCTGGGTATCCGGAAATACCGAATACGTTTGTATGATCTTCTT
GGGAAATCGGTCATTTAGCCTTTCCAAGAGGAATGAGCCCAGACCTGAGCCTGTGCC
ACCAGCAATCGAATGCAGCATCATAAAGCCCTCGAGTGAGTCGCTTCCATCTGCTTC
CCTATCAATCATCTCCATAATGACATGAGGATCACCCATGACATTATGGAGATGATT
GATAGGGAAGCAGATGGAAGCGACTCACTCGAGGGCTTTATGATGCTGCATTCGATT
GCTGGTGGCACAGGCTCAGGTCTGGGCTCATTCCTCTTGGAAAGGCTAAATGACCG
ATTTCCCAAGAAGATCATACAAACGTATTCGGTATTTCCGGA (SEQ ID NO 51)

Figure 54: *Nilaparvata lugens* tubulin with MS2 recognition sequence (bold and underlined)
CAGACAGAATCATGAACACCTACTCCGTTGTGCCCTCACCAAAGGTATCCGACACAG
TTGTCGAGCCATACAATGCCACCCTCTCCGTTCATCAGCTCGTCGAAAACACCGATG
AAACCTACTGTATCGACATGAGGATCACCCATGACGATACAGTAGGTTTCATCGGTG
TTTTCGACGAGCTGATGAACGGAGAGGGTGGCATTGTATGGCTCGACAACTGTGTCG
GATACCTTTGGTGAGGGCACAACGGAGTAGGTGTTCATGATTCTGTCTGGGTATTCC
TCGCGGATTTTCGAGATCAGCAATGTTCCCATTCCTGATCCGGTACCACCTCCCAAC
GAATGAGTCAGCTGGAATCCCTGTAAGCAATCGCAGCTCTCGGCTTCCTTTCTGACT
ACGTCGAACATGAGGATCACCCATGATCGACGTAGTCAGAAAGGAAGCCGAGAGCT
GCGATTGCTTACAGGGATTCCAGCTGACTCATTCGTTGGGAGGTGGTACCGGATCAG
GAATGGGAACATTGCTGATCTCGAAAATCCGCGAGGAATACC (SEQ ID NO 52)

Figure 55:

RNA binding protein
recognition sequence

RNA binding protein
recognition sequence 3  5

Target sequence

Figure 56: *Caenorhabditis elegans* unc-22 with LicT recognition sequence (bold and underlined)
ATACTTCTCGTGGAACATGGCAGGAAGTCGGAACTTTCCCAGATTGTACAGCCAAGG
TTAATAAGCTTGTTCCTGGAAAGGAATACGCATTCCGTGTCAAGGCAGTCAATCTTCA
AGGAGAATCAAAACCATTGGAAGCTGAAGAACCAATTATTGCAAAGAATCAATTTGAT
GTTCCTGATCCAGTTGACAAACCAGAGGTTACTGACT**GGATTGTTACTGCGAAAGCA
GGCAAAACC**AGTCAGTAACCTCTGGTTTGTCAACTGGATCAGGAACATCAAATTGAT
TCTTTGCAATAATTGGTTCTTCAGCTTCCAATGGTTTTGATTCTCCTTGAAGATTGACT
GCCTTGACACGGAATGCGTATTCCTTTCCAGGAACAAGCTTATTAACCTTGGCTGTAC
AATCTGGGAAAGTTCCGACTTCCTGCCATGTTCCACGAGAAGTATCCATCTTCTCAAC
AATGTAGTGAAGAACATCAGTTCCTCCGTTATCAGTTGGAGGCTTCCAGTTCAATGTA
CATCCTTCCTTATGGATCTCGTCAATCTTGAGTGGTCCTTCTGGAGTTCCTGGTACAT
CAAGAACAGTAACATTGCACTGAGCAGTATCTTTTCCATGCTCATTTTCAACAATGATT
TTGTAAACTCCAGTATCTCCACGGATTGTTACTGCGAAAGCAGGCAAAACCGTGGA
GATACTGGAGTTTACAAAATCATTGTTGAAAATGAGCATGGAAAAGATACTGCTCAGT
GCAATGTTACTGTTCTTGATGTACCAGGAACTCCAGAAGGACCACTCAAGATTGACG
AGATCCATAAGGAAGGATGTACATTGAACTGGAAGCCTCCAACTGATAACGGAGGAA
CTGATGTTCTTCACTACATTGTTGAGAAGATGG (SEQ ID NO 54)

Figure 57: *Caenorhabditis elegans unc-22* with Nun recognition sequence (bold and underlined)
ATACTTCTCGTGGAACATGGCAGGAAGTCGGAACTTTCCCAGATTGTACAGCCAAGG
TTAATAAGCTTGTTCCTGGAAAGGAATACGCATTCCGTGTCAAGGCAGTCAATCTTCA
AGGAGAATCAAAACCATTGGAAGCTGAAGAACCAATTATTGCAAAGAATCAATTTGAT
GTTCCTGATCCAGTTGACAAACCAGAGGTTACTGACTGCCCTGAAAAAGGGCAGTCA
GTAACCTCTGGTTTGTCAACTGGATCAGGAACATCAAATTGATTCTTTGCAATAATTG
GTTCTTCAGCTTCCAATGGTTTTGATTCTCCTTGAAGATTGACTGCCTTGACACGGAA
TGCGTATTCCTTTCCAGGAACAAGCTTATTAACCTTGGCTGTACAATCTGGGAAAGTT
CCGACTTCCTGCCATGTTCCACGAGAAGTATCCATCTTCTCAACAATGTAGTGAAGAA
CATCAGTTCCTCCGTTATCAGTTGGAGGCTTCCAGTTCAATGTACATCCTTCCTTATG
GATCTCGTCAATCTTGAGTGGTCCTTCTGGAGTTCCTGGTACATCAAGAACAGTAACA
TTGCACTGAGCAGTATCTTTTCCATGCTCATTTTCAACAATGATTTTGTAAACTCCAGT
ATCTCCACGCCCTGAAAAAGGGCGTGGAGATACTGGAGTTTACAAAATCATTGTTGA
AAATGAGCATGGAAAAGATACTGCTCAGTGCAATGTTACTGTTCTTGATGTACCAGGA
ACTCCAGAAGGACCACTCAAGATTGACGAGATCCATAAGGAAGGATGTACATTGAAC
TGGAAGCCTCCAACTGATAACGGAGGAACTGATGTTCTTCACTACATTGTTGAGAAG
ATGG (SEQ ID NO 55)

Figure 58: *Caenorhabditis elegans unc-22* with MS2 recognition sequence (bold and underlined)
ATACTTCTCGTGGAACATGGCAGGAAGTCGGAACTTTCCCAGATTGTACAGCCAAGG
TTAATAAGCTTGTTCCTGGAAAGGAATACGCATTCCGTGTCAAGGCAGTCAATCTTCA
AGGAGAATCAAAACCATTGGAAGCTGAAGAACCAATTATTGCAAAGAATCAATTTGAT
GTTCCTGATCCAGTTGACAAACCAGAGGTTACTGACTACATGAGGATCACCCATGAA
GTCAGTAACCTCTGGTTTGTCAACTGGATCAGGAACATCAAATTGATTCTTTGCAATA
ATTGGTTCTTCAGCTTCCAATGGTTTTGATTCTCCTTGAAGATTGACTGCCTTGACAC
GGAATGCGTATTCCTTTCCAGGAACAAGCTTATTAACCTTGGCTGTACAATCTGGGAA
AGTTCCGACTTCCTGCCATGTTCCACGAGAAGTATCCATCTTCTCAACAATGTAGTGA
AGAACATCAGTTCCTCCGTTATCAGTTGGAGGCTTCCAGTTCAATGTACATCCTTCCT
TATGGATCTCGTCAATCTTGAGTGGTCCTTCTGGAGTTCCTGGTACATCAAGAACAGT
AACATTGCACTGAGCAGTATCTTTTCCATGCTCATTTTCAACAATGATTTTGTAAACTC
CAGTATCTCCACACATGAGGATCACCCATGAGTGGAGATACTGGAGTTTACAAAATC
ATTGTTGAAAATGAGCATGGAAAAGATACTGCTCAGTGCAATGTTACTGTTCTTGATG
TACCAGGAACTCCAGAAGGACCACTCAAGATTGACGAGATCCATAAGGAAGGATGTA
CATTGAACTGGAAGCCTCCAACTGATAACGGAGGAACTGATGTTCTTCACTACATTGT
TGAGAAGATGG (SEQ ID NO 56)

Figure 59:

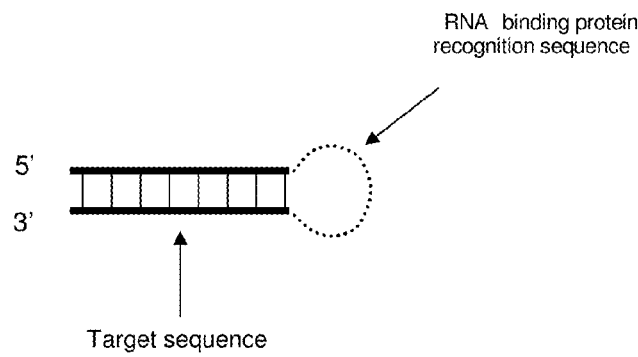

Figure 60: *Meloidogyne incognita* tubulin with LicT recognition sequence (bold and underlined)
TGGATGTTGTTCGAAAAGAGGCTGAGGGTTGTGATTGTCTTCAAGGTTTTCAATTGAC
TCACTCGCTTGGTGGTGGAACTGGCTCTGGAATGGGAACTTTGCTCATTTCAAAGAT
TCGTGAGGAGTATCCGGACCGCATTACGTCTTCCTTCTCTGTTGTTCCGTCGCCTAA
GGTCTCTGACACGGTCGTTGAGCCCTACAACGCAACTCTTTCTGTTCATCAACTTGTT
GAGAACACCGACGAGACTTACTGCATCGGGATTGTTACTGCGAAAGCAGGCAAAAC
CCGATGCAGTAAGTCTCGTCGGTGTTCTCAACAAGTTGATGAACAGAAAGAGTTGCG
TTGTAGGGCTCAACGACCGTGTCAGAGACCTTAGGCGACGGAACAACAGAGAAGGA
AGACGTAATGCGGTCCGGATACTCCTCACGAATCTTTGAAATGAGCAAAGTTCCCATT
CCAGAGCCAGTTCCACCACCAAGCGAGTGAGTCAATTGAAAACCTTGAAGACAATCA
CAACCCTCAGCCTCTTTTCGAACAACATCCA (SEQ ID NO 57)

Figure 61: *Caenorhabditis elegans* tubulin with LicT recognition sequence (bold and underlined)
GACGTGATCCGCAAGGAAGCCGAAGGATGCGATTGTCTTCAAGGATTCCAACTCACT
CACTCTCTCGGAGGAGGAACCGGATCTGGAATGGGAACACTTCTCATCTCCAAAATC
CGCGAAGAGTACCCAGACAGAATCATGAGCTCATTCTCGGTTGTACCATCGCCAAAG
GTGTCCGACACAGTTGTAGAACCATACAATGCCACCCTCTCCGTCCACCAGCTTGTT
GAGAACACCGATGAGACCTACTGCATTGGATTGTTACTGCGAAAGCAGGCAAAACC
AATGCAGTAGGTCTCATCGGTGTTCTCAACAAGCTGGTGGACGGAGAGGGTGGCAT
TGTATGGTTCTACAACTGTGTCGGACACCTTTGGCGATGGTACAACCGAGAATGAGC
TCATGATTCTGTCTGGGTACTCTTCGCGGATTTTGGAGATGAGAAGTGTTCCCATTCC
AGATCCGGTTCCTCCTCCGAGAGAGTGAGTGAGTTGGAATCCTTGAAGACAATCGCA
TCCTTCGGCTTCCTTGCGGATCACGTC (SEQ ID NO 58)

Figure 62: *Magnaporthe grisea* tubulin with LicT recognition sequence (bold and underlined)
CATTATGGAGATGATTGATAGGGAAGCAGATGGAAGCGACTCACTCGAGGGCTTTAT
GATGCTGCATTCGATTGCTGGTGGCACAGGCTCAGGTCTGGGCTCATTCCTCTTGGA
AAGGCTAAATGACCGATTTCCCAAGAAGATCATACAAACGTATTCGGTATTTCCG
GATACCCAGAATGCCGGAGACGTCGTCGTCCATCCCTACAACAGCATCCTAGCCATG
AGGAGATTGACACAGAATGCCGACTCGGTGGTGGTGCTGGATAACGGCGCTCTCTC
ACATATTGCAGCCGATAGACTCCACGTGCAAGAGCCGTCTTTTCAGCAGACAAATCA
ACTGGGATTGTTACTGCGAAAGCAGGCAAAACCCAGTTGATTTGTCTGCTGAAAAG
ACGGCTCTTGCACGTGGAGTCTATCGGCTGCAATATGTGAGAGAGCGCCGTTATCCA
GCACCACCACCGAGTCGGCATTCTGTGTCAATCTCCTCATGGCTAGGATGCTGTTGT
AGGGATGGACGACGACGTCTCCGGCATTCTGGGTATCCGGAAATACCGAATACGTTT
GTATGATCTTCTTGGGAAATCGGTCATTTAGCCTTTCCAAGAGGAATGAGCCCAGAC
CTGAGCCTGTGCCACCAGCAATCGAATGCAGCATCATAAAGCCCTCGAGTGAGTCG
CTTCCATCTGCTTCCCTATCAATCATCTCCATAATG (SEQ ID NO 59)

Figure 63: *Nilaparvata lugens* tubulin with LicT recognition sequence (bold and underlined)
TCGACGTAGTCAGAAAGGAAGCCGAGAGCTGCGATTGCTTACAGGGATTCCAGCTG
ACTCATTCGTTGGGAGGTGGTACCGGATCAGGAATGGGAACATTGCTGATCTCGAAA
ATCCGCGAGGAATACCCAGACAGAATCATGAACACCTACTCCGTTGTGCCCTCACCA
AAGGTATCCGACACAGTTGTCGAGCCATACAATGCCACCCTCTCCGTTCATCAGCTC
GTCGAAAACACCGATGAAACCTACTGTATCGGGATTGTTACTGCGAAAGCAGGCAA
AACCCGATACAGTAGGTTTCATCGGTGTTTTCGACGAGCTGATGAACGGAGAGGGT
GGCATTGTATGGCTCGACAACTGTGTCGGATACCTTTGGTGAGGGCACAACGGAGTA
GGTGTTCATGATTCTGTCTGGGTATTCCTCGCGGATTTTCGAGATCAGCAATGTTCCC
ATTCCTGATCCGGTACCACCTCCCAACGAATGAGTCAGCTGGAATCCCTGTAAGCAA
TCGCAGCTCTCGGCTTCCTTTCTGACTACGTCGA (SEQ ID NO 60)

Figure 64: *Meloidogyne incognita* tubulin with Nun recognition sequence(bold and underlined)
TGGATGTTGTTCGAAAAGAGGCTGAGGGTTGTGATTGTCTTCAAGGTTTTCAATTGAC
TCACTCGCTTGGTGGTGGAACTGGCTCTGGAATGGGAACTTTGCTCATTTCAAAGAT
TCGTGAGGAGTATCCGGACCGCATTACGTCTTCCTTCTCTGTTGTTCCGTCGCCTAA
GGTCTCTGACACGGTCGTTGAGCCCTACAACGCAACTCTTTCTGTTCATCAACTTGTT
GAGAACACCGACGAGACTTACTGCATCG<u>GCCCTGAAAAAGGGC</u>CGATGCAGTAAGT
CTCGTCGGTGTTCTCAACAAGTTGATGAACAGAAAGAGTTGCGTTGTAGGGCTCAAC
GACCGTGTCAGAGACCTTAGGCGACGGAACAACAGAGAAGGAAGACGTAATGCGGT
CCGGATACTCCTCACGAATCTTTGAAATGAGCAAAGTTCCCATTCCAGAGCCAGTTC
CACCACCAAGCGAGTGAGTCAATTGAAAACCTTGAAGACAATCACAACCCTCAGCCT
CTTTTCGAACAACATCCA (SEQ ID NO 61)

Figure 65: *Caenorhabditis elegans* tubulin with Nun recognition sequence (bold and underlined)
GACGTGATCCGCAAGGAAGCCGAAGGATGCGATTGTCTTCAAGGATTCCAACTCACT
CACTCTCTCGGAGGAGGAACCGGATCTGGAATGGGAACACTTCTCATCTCCAAAATC
CGCGAAGAGTACCCAGACAGAATCATGAGCTCATTCTCGGTTGTACCATCGCCAAAG
GTGTCCGACACAGTTGTAGAACCATACAATGCCACCCTCTCCGTCCACCAGCTTGTT
GAGAACACCGATGAGACCTACTGCATT<u>GCCCTGAAAAAGGGC</u>AATGCAGTAGGTCT
CATCGGTGTTCTCAACAAGCTGGTGGACGGAGAGGGTGGCATTGTATGGTTCTACAA
CTGTGTCGGACACCTTTGGCGATGGTACAACCGAGAATGAGCTCATGATTCTGTCTG
GGTACTCTTCGCGGATTTTGGAGATGAGAAGTGTTCCCATTCCAGATCCGGTTCCTC
CTCCGAGAGAGTGAGTGAGTTGGAATCCTTGAAGACAATCGCATCCTTCGGCTTCCT
TGCGGATCACGTC (SEQ ID NO 62)

Figure 66: *Magnaporthe grisea* tubulin with Nun recognition sequence (bold and underlined)
CATTATGGAGATGATTGATAGGGAAGCAGATGGAAGCGACTCACTCGAGGGCTTTAT
GATGCTGCATTCGATTGCTGGTGGCACAGGCTCAGGTCTGGGCTCATTCCTCTTGGA
AAGGCTAAATGACCGATTTCCCAAGAAGATCATACAAACGTATTCGGTATTTCCGGAT
ACCCAGAATGCCGGAGACGTCGTCGTCCATCCCTACAACAGCATCCTAGCCATGAG
GAGATTGACACAGAATGCCGACTCGGTGGTGGTGCTGGATAACGGCGCTCTCTCAC
ATATTGCAGCCGATAGACTCCACGTGCAAGAGCCGTCTTTTCAGCAGACAAATCAAC
TG<u>GCCCTGAAAAAGGGC</u>CAGTTGATTTGTCTGCTGAAAAGACGGCTCTTGCACGTG
GAGTCTATCGGCTGCAATATGTGAGAGAGCGCCGTTATCCAGCACCACCACCGAGT
CGGCATTCTGTGTCAATCTCCTCATGGCTAGGATGCTGTTGTAGGGATGGA
CGACGACGTCTCCGGCATTCTGGGTATCCGGAAATACCGAATACGTTTGTATGATCT
TCTTGGGAAATCGGTCATTTAGCCTTTCCAAGAGGAATGAGCCCAGACCTGAGCCTG
TGCCACCAGCAATCGAATGCAGCATCATAAAGCCCTCGAGTGAGTCGCTTCCATCTG
CTTCCCTATCAATCATCTCCATAATG (SEQ ID NO 63)

Figure 67: *Nilaparvata lugens* tubulin with Nun recognition sequence (bold and underlined)
TCGACGTAGTCAGAAAGGAAGCCGAGAGCTGCGATTGCTTACAGGGATTCCAGCTG
ACTCATTCGTTGGGAGGTGGTACCGGATCAGGAATGGGAACATTGCTGATCTCGAAA
ATCCGCGAGGAATACCCAGACAGAATCATGAACACCTACTCCGTTGTGCCCTCACCA
AAGGTATCCGACACAGTTGTCGAGCCATACAATGCCACCCTCTCCGTTCATCAGCTC
GTCGAAAACACCGATGAAACCTACTGTATCGGCCCTGAAAAAGGGCCGATACAGTA
GGTTTCATCGGTGTTTCGACGAGCTGATGAACGGAGAGGGTGGCATTGTATGGCTC
GACAACTGTGTCGGATACCTTTGGTGAGGGCACAACGGAGTAGGTGTTCATGATTCT
GTCTGGGTATTCCTCGCGGATTTTCGAGATCAGCAATGTTCCCATTCCTGATCCGGT
ACCACCTCCCAACGAATGAGTCAGCTGGAATCCCTGTAAGCAATCGCAGCTCTCGGC
TTCCTTTCTGACTACGTCGA (SEQ ID NO 64)

Figure 68: *Meloidogyne incognita* tubulin with MS2 recognition sequence (bold and underlined)
TGGATGTTGTTCGAAAAGAGGCTGAGGGTTGTGATTGTCTTCAAGGTTTTCAATTGAC
TCACTCGCTTGGTGGTGGAACTGGCTCTGGAATGGGAACTTTGCTCATTTCAAAGAT
TCGTGAGGAGTATCCGGACCGCATTACGTCTTCCTTCTCTGTTGTTCCGTCGCCTAA
GGTCTCTGACACGGTCGTTGAGCCCTACAACGCAACTCTTTCTGTTCATCAACTTGTT
GAGAACACCGACGAGACTTACTGCATCGACATGAGGATCACCCATGACGATGCAGT
AAGTCTCGTCGGTGTTCTCAACAAGTTGATGAACAGAAAGAGTTGCGTTGTAGGGCT
CAACGACCGTGTCAGAGACCTTAGGCGACGGAACAACAGAGAAGGAAGACGTAATG
CGGTCCGGATACTCCTCACGAATCTTTGAAATGAGCAAAGTTCCCATTCCAGAGCCA
GTTCCACCACCAAGCGAGTGAGTCAATTGAAAACCTTGAAGACAATCACAACCCTCA
GCCTCTTTTCGAACAACATCCA (SEQ ID NO 65)

Figure 69: *Caenorhabditis elegans* tubulin with MS2 recognition sequence(bold and underlined)
GACGTGATCCGCAAGGAAGCCGAAGGATGCGATTGTCTTCAAGGATTCCAACTCACT
CACTCTCTCGGAGGAGGAACCGGATCTGGAATGGGAACACTTCTCATCTCCAAAATC
CGCGAAGAGTACCCAGACAGAATCATGAGCTCATTCTCGGTTGTACCATCGCCAAAG
GTGTCCGACACAGTTGTAGAACCATACAATGCCACCCTCTCCGTCCACCAGCTTGTT
GAGAACACCGATGAGACCTACTGCATTACATGAGGATCACCCATGAAATGCAGTAG
GTCTCATCGGTGTTCTCAACAAGCTGGTGGACGGAGAGGGTGGCATTGTATGGTTCT
ACAACTGTGTCGGACACCTTTGGCGATGGTACAACCGAGAATGAGCTCATGATTCTG
TCTGGGTACTCTTCGCGGATTTTGGAGATGAGAAGTGTTCCCATTCCAGATCCGGTT
CCTCCTCCGAGAGAGTGAGTGAGTTGGAATCCTTGAAGACAATCGCATCCTTCGGCT
TCCTTGCGGATCACGTC (SEQ ID NO 66)

Figure 70: *Magnaporthe grisea* tubulin with MS2 recognition sequence (bold and underlined)
CATTATGGAGATGATTGATAGGGAAGCAGATGGAAGCGACTCACTCGAGGGCTTTAT
GATGCTGCATTCGATTGCTGGTGGCACAGGCTCAGGTCTGGGCTCATTCCTCTTGGA
AAGGCTAAATGACCGATTTCCCAAGAAGATCATACAAACGTATTCGGTATTTCCGGAT
ACCCAGAATGCCGGAGACGTCGTCGTCCATCCCTACAACAGCATCCTAGCCATGAG
GAGATTGACACAGAATGCCGACTCGGTGGTGGTGCTGGATAACGGCGCTCTCTCAC
ATATTGCAGCCGATAGACTCCACGTGCAAGAGCCGTCTTTTCAGCAGACAAATCAAC
TG<u>ACATGAGGATCACCCATGA</u>CAGTTGATTTGTCTGCTGAAAAGACGGCTCTTGCAC
GTGGAGTCTATCGGCTGCAATATGTGAGAGAGCGCCGTTATCCAGCACCACCACCG
AGTCGGCATTCTGTGTCAATCTCCTCATGGCTAGGATGCTGTTGTAGGGATGGACGA
CGACGTCTCCGGCATTCTGGGTATCCGGAAATACCGAATACGTTTGTATGATCTTCTT
GGGAAATCGGTCATTTAGCCTTTCCAAGAGGAATGAGCCCAGACCTGAGCCTGTGCC
ACCAGCAATCGAATGCAGCATCATAAAGCCCTCGAGTGAGTCGCTTCCATCTGCTTC
CCTATCAATCATCTCCATAATG (SEQ ID NO 67)

Figure 71: *Nilaparvata lugens* tubulin with MS2 recognition sequence (bold and underlined)
TCGACGTAGTCAGAAAGGAAGCCGAGAGCTGCGATTGCTTACAGGGATTCCAGCTG
ACTCATTCGTTGGGAGGTGGTACCGGATCAGGAATGGGAACATTGCTGATCTCGAAA
ATCCGCGAGGAATACCCAGACAGAATCATGAACACCTACTCCGTTGTGCCCTCACCA
AAGGTATCCGACACAGTTGTCGAGCCATACAATGCCACCCTCTCCGTTCATCAGCTC
GTCGAAAACACCGATGAAACCTACTGTATCG<u>ACATGAGGATCACCCATGA</u>CGATACA
GTAGGTTTCATCGGTGTTTTCGACGAGCTGATGAACGGAGAGGGTGGCATTGTATGG
CTCGACAACTGTGTCGGATACCTTTGGTGAGGGCACAACGGAGTAGGTGTTCATGAT
TCTGTCTGGGTATTCCTCGCGGATTTTCGAGATCAGCAATGTTCCCATTCCTGATCCG
GTACCACCTCCCAACGAATGAGTCAGCTGGAATCCCTGTAAGCAATCGCAGCTCTCG
GCTTCCTTTCTGACTACGTCGA (SEQ ID NO 68)

Figure 72: *Caenorhabditis elegans unc-22* with LicT recognition sequence (bold and underlined)
GTGGAGATACTGGAGTTTACAAAATCATTGTTGAAAATGAGCATGGAAAAGATACTGC
TCAGTGCAATGTTACTGTTCTTGATGTACCAGGAACTCCAGAAGGACCACTCAAGATT
GACGAGATCCATAAGGAAGGATGTACATTGAACTGGAAGCCTCCAACTGATAACGGA
GGAACTGATGTTCTTCACTACATTGTTGAGAAGATGGATACTTCTCGTGGAACATGGC
AGGAAGTCGGAACTTTCCCAGATTGTACAGCCAAGGTTAATAAGCTTGTTCCTGGAA
AGGAATACGCATTCCGTGTCAAGGCAGTCAATCTTCAAGGAGAATCAAAACCATTGG
AAGCTGAAGAACCAATTATTGCAAAGAATCAATTTGATGTTCCTGATCCAGTTGACAA
ACCAGAGGTTACTGACT<u>GGATTGTTACTGCGAAAGCAGGCAAAACC</u>AGTCAGTAAC
CTCTGGTTTGTCAACTGGATCAGGAACATCAAATTGATTCTTTGCAATAATTGGTTCTT
CAGCTTCCAATGGTTTTGATTCTCCTTGAAGATTGACTGCCTTGACACGGAATGCGTA
TTCCTTTCCAGGAACAAGCTTATTAACCTTGGCTGTACAATCTGGGAAAGTTCCGACT
TCCTGCCATGTTCCACGAGAAGTATCCATCTTCTCAACAATGTAGTGAAGAACATCAG
TTCCTCCGTTATCAGTTGGAGGCTTCCAGTTCAATGTACATCCTTCCTTATGGATCTC
GTCAATCTTGAGTGGTCCTTCTGGAGTTCCTGGTACATCAAGAACAGTAACATTGCAC
TGAGCAGTATCTTTTCCATGCTCATTTTCAACAATGATTTTGTAAACTCCAGTATCTCC
AC (SEQ ID NO 69)

Figure 73: *Caenorhabditis elegans unc-22* with Nun recognition sequence (bold and underlined)
GTGGAGATACTGGAGTTTACAAAATCATTGTTGAAAATGAGCATGGAAAAGATACTGC
TCAGTGCAATGTTACTGTTCTTGATGTACCAGGAACTCCAGAAGGACCACTCAAGATT
GACGAGATCCATAAGGAAGGATGTACATTGAACTGGAAGCCTCCAACTGATAACGGA
GGAACTGATGTTCTTCACTACATTGTTGAGAAGATGGATACTTCTCGTGGAACATGGC
AGGAAGTCGGAACTTTCCCAGATTGTACAGCCAAGGTTAATAAGCTTGTTCCTGGAA
AGGAATACGCATTCCGTGTCAAGGCAGTCAATCTTCAAGGAGAATCAAAACCATTGG
AAGCTGAAGAACCAATTATTGCAAAGAATCAATTTGATGTTCCTGATCCAGTTGACAA
ACCAGAGGTTACTGACT<u>GCCCTGAAAAAGGGC</u>AGTCAGTAACCTCTGGTTTGTCAAC
TGGATCAGGAACATCAAATTGATTCTTTGCAATAATTGGTTCTTCAGCTTCCAATGGTT
TTGATTCTCCTTGAAGATTGACTGCCTTGACACGGAATGCGTATTCCTTTCCAGGAAC
AAGCTTATTAACCTTGGCTGTACAATCTGGGAAAGTTCCGACTTCCTGCCATGTTCCA
CGAGAAGTATCCATCTTCTCAACAATGTAGTGAAGAACATCAGTTCCTCCGTTATCAG
TTGGAGGCTTCCAGTTCAATGTACATCCTTCCTTATGGATCTCGTCAATCTTGAGTGG
TCCTTCTGGAGTTCCTGGTACATCAAGAACAGTAACATTGCACTGAGCAGTATCTTTT
CCATGCTCATTTTCAACAATGATTTTGTAAACTCCAGTATCTCCAC (SEQ ID NO 70)

Figure 74: *Caenorhabditis elegans unc-22* with MS2 recognition sequence (bold and underlined)
GTGGAGATACTGGAGTTTACAAAATCATTGTTGAAAATGAGCATGGAAAAGATACTGC
TCAGTGCAATGTTACTGTTCTTGATGTACCAGGAACTCCAGAAGGACCACTCAAGATT
GACGAGATCCATAAGGAAGGATGTACATTGAACTGGAAGCCTCCAACTGATAACGGA
GGAACTGATGTTCTTCACTACATTGTTGAGAAGATGGATACTTCTCGTGGAACATGGC
AGGAAGTCGGAACTTTCCCAGATTGTACAGCCAAGGTTAATAAGCTTGTTCCTGGAA
AGGAATACGCATTCCGTGTCAAGGCAGTCAATCTTCAAGGAGAATCAAAACCATTGG
AAGCTGAAGAACCAATTATTGCAAAGAATCAATTTGATGTTCCTGATCCAGTTGACAA
ACCAGAGGTTACTGACTACATGAGGATCACCCATGAAGTCAGTAACCTCTGGTTTGT
CAACTGGATCAGGAACATCAAATTGATTCTTTGCAATAATTGGTTCTTCAGCTTCCAAT
GGTTTTGATTCTCCTTGAAGATTGACTGCCTTGACACGGAATGCGTATTCCTTTCCAG
GAACAAGCTTATTAACCTTGGCTGTACAATCTGGGAAAGTTCCGACTTCCTGCCATGT
TCCACGAGAAGTATCCATCTTCTCAACAATGTAGTGAAGAACATCAGTTCCTCCGTTA
TCAGTTGGAGGCTTCCAGTTCAATGTACATCCTTCCTTATGGATCTCGTCAATCTTGA
GTGGTCCTTCTGGAGTTCCTGGTACATCAAGAACAGTAACATTGCACTGAGCAGTAT
CTTTTCCATGCTCATTTTCAACAATGATTTTGTAAACTCCAGTATCTCCAC (SEQ ID NO 71)

Figure 75:

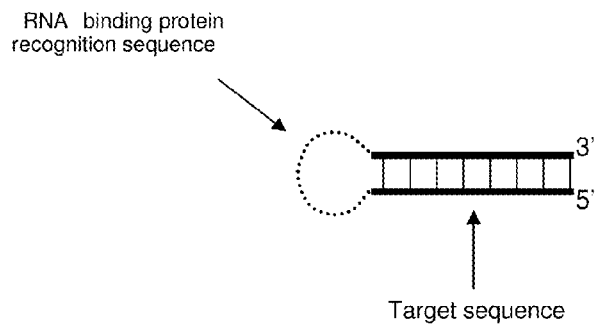

Figure 76: *Meloidogyne incognita* tubulin with LicT recognition sequence (bold and underlined)
CGATGCAGTAAGTCTCGTCGGTGTTCTCAACAAGTTGATGAACAGAAAGAGTTGCGT
TGTAGGGCTCAACGACCGTGTCAGAGACCTTAGGCGACGGAACAACAGAGAAGGAA
GACGTAATGCGGTCCGGATACTCCTCACGAATCTTTGAAATGAGCAAAGTTCCCATT
CCAGAGCCAGTTCCACCACCAAGCGAGTGAGTCAATTGAAAACCTTGAAGACAATCA
CAACCCTCAGCCTCTTTTCGAACAACATCCA**GGATTGTTACTGCGAAAGCAGGCAAA
ACC**TGGATGTTGTTCGAAAAGAGGCTGAGGGTTGTGATTGTCTTCAAGGTTTTCAATT
GACTCACTCGCTTGGTGGTGGAACTGGCTCTGGAATGGGAACTTTGCTCATTTCAAA
GATTCGTGAGGAGTATCCGGACCGCATTACGTCTTCCTTCTCTGTTGTTCCGTCGCC
TAAGGTCTCTGACACGGTCGTTGAGCCCTACAACGCAACTCTTTCTGTTCATCAACTT
GTTGAGAACACCGACGAGACTTACTGCATCG (SEQ ID NO 72)

Figure 77: *Caenorhabditis elegans* tubulin with LicT recognition sequence (bold and underlined)
AATGCAGTAGGTCTCATCGGTGTTCTCAACAAGCTGGTGGACGGAGAGGGTGGCAT
TGTATGGTTCTACAACTGTGTCGGACACCTTTGGCGATGGTACAACCGAGAATGAGC
TCATGATTCTGTCTGGGTACTCTTCGCGGATTTTGGAGATGAGAAGTGTTCCCATTCC
AGATCCGGTTCCTCCTCCGAGAGAGTGAGTGAGTTGGAATCCTTGAAGACAATCGCA
TCCTTCGGCTTCCTTGCGGATCACGTC<u>GGATTGTTACTGCGAAAGCAGGCAAAACC</u>
GACGTGATCCGCAAGGAAGCCGAAGGATGCGATTGTCTTCAAGGATTCCAACTCACT
CACTCTCTCGGAGGAGGAACCGGATCTGGAATGGGAACACTTCTCATCTCCAAAATC
CGCGAAGAGTACCCAGACAGAATCATGAGCTCATTCTCGGTTGTACCATCGCCAAAG
GTGTCCGACACAGTTGTAGAACCATACAATGCCACCCTCTCCGTCCACCAGCTTGTT
GAGAACACCGATGAGACCTACTGCATT (SEQ ID NO 73)

Figure 78: *Magnaporthe grisea* tubulin with LicT recognition sequence (bold and underlined)
CAGTTGATTTGTCTGCTGAAAAGACGGCTCTTGCACGTGGAGTCTATCGGCTGCAAT
ATGTGAGAGAGCGCCGTTATCCAGCACCACCACCGAGTCGGCATTCTGTGTCAATCT
CCTCATGGCTAGGATGCTGTTGTAGGGATGGACGACGACGTCTCCGGCATTCTGGG
TATCCGGAAATACCGAATACGTTTGTATGATCTTCTTGGGAAATCGGTCATTTAGCCT
TTCCAAGAGGAATGAGCCCAGACCTGAGCCTGTGCCACCAGCAATCGAATGCAGCA
TCATAAAGCCCTCGAGTGAGTCGCTTCCATCTGCTTCCCTATCAATCATCTCCATAAT
G<u>GGATTGTTACTGCGAAAGCAGGCAAAACC</u>CATTATGGAGATGATTGATAGGGAAG
CAGATGGAAGCGACTCACTCGAGGGCTTTATGATGCTGCATTCGATTGCTGGTGGCA
CAGGCTCAGGTCTGGGCTCATTCCTCTTGGAAAGGCTAAATGACCGATTTCCCAAGA
AGATCATACAAACGTATTCGGTATTTCCGGATACCCAGAATGCCGGAGACGTCGTCG
TCCATCCCTACAACAGCATCCTAGCCATGAGGAGATTGACACAGAATGCCGACTCGG
TGGTGGTGCTGGATAACGGCGCTCTCTCACATATTGCAGCCGATAGACTCCACGTGC
AAGAGCCGTCTTTTCAGCAGACAAATCAACTG (SEQ ID NO 74)

Figure 79: *Nilaparvata lugens* tubulin with LicT recognition sequence(bold and underlined)
CGATACAGTAGGTTTCATCGGTGTTTTCGACGAGCTGATGAACGGAGAGGGTGGCAT
TGTATGGCTCGACAACTGTGTCGGATACCTTTGGTGAGGGCACAACGGAGTAGGTGT
TCATGATTCTGTCTGGGTATTCCTCGCGGATTTTCGAGATCAGCAATGTTCCCATTCC
TGATCCGGTACCACCTCCCAACGAATGAGTCAGCTGGAATCCCTGTAAGCAATCGCA
GCTCTCGGCTTCCTTTCTGACTACGTCGA<u>GGATTGTTACTGCGAAAGCAGGCAAAA</u>
<u>CC</u>TCGACGTAGTCAGAAAGGAAGCCGAGAGCTGCGATTGCTTACAGGGATTCCAGC
TGACTCATTCGTTGGGAGGTGGTACCGGATCAGGAATGGGAACATTGCTGATCTCGA
AAATCCGCGAGGAATACCCAGACAGAATCATGAACACCTACTCCGTTGTGCCCTCAC
CAAAGGTATCCGACACAGTTGTCGAGCCATACAATGCCACCCTCTCCGTTCATCAGC
TCGTCGAAAACACCGATGAAACCTACTGTATCG (SEQ ID NO 75)

Figure 80: *Meloidogyne incognita* tubulin with Nun recognition sequence (bold and underlined)
CGATGCAGTAAGTCTCGTCGGTGTTCTCAACAAGTTGATGAACAGAAAGAGTTGCGT
TGTAGGGCTCAACGACCGTGTCAGAGACCTTAGGCGACGGAACAACAGAGAAGGAA
GACGTAATGCGGTCCGGATACTCCTCACGAATCTTTGAAATGAGCAAAGTTCCCATT
CCAGAGCCAGTTCCACCACCAAGCGAGTGAGTCAATTGAAAACCTTGAAGACAATCA
CAACCCTCAGCCTCTTTTCGAACAACATCCA<u>GCCCTGAAAAAGGGC</u>TGGATGTTGTT
CGAAAAGAGGCTGAGGGTTGTGATTGTCTTCAAGGTTTTCAATTGACTCACTCGCTTG
GTGGTGGAACTGGCTCTGGAATGGGAACTTTGCTCATTTCAAAGATTCGTGAGGAGT
ATCCGGACCGCATTACGTCTTCCTTCTCTGTTGTTCCGTCGCCTAAGGTCTCTGACAC
GGTCGTTGAGCCCTACAACGCAACTCTTTCTGTTCATCAACTTGTTGAGAACACCGAC
GAGACTTACTGCATCG (SEQ ID NO 76)

Figure 81: *Caenorhabditis elegans* tubulin with Nun recognition sequence (bold and underlined)
AATGCAGTAGGTCTCATCGGTGTTCTCAACAAGCTGGTGGACGGAGAGGGTGGCAT
TGTATGGTTCTACAACTGTGTCGGACACCTTTGGCGATGGTACAACCGAGAATGAGC
TCATGATTCTGTCTGGGTACTCTTCGCGGATTTTGGAGATGAGAAGTGTTCCCATTCC
AGATCCGGTTCCTCCTCCGAGAGAGTGAGTGAGTTGGAATCCTTGAAGACAATCGCA
TCCTTCGGCTTCCTTGCGGATCACGTGCCCTGAAAAAGGGCGACGTGATCCGCAA
GGAAGCCGAAGGATGCGATTGTCTTCAAGGATTCCAACTCACTCACTCTCTCGGAGG
AGGAACCGGATCTGGAATGGGAACACTTCTCATCTCCAAAATCCGCGAAGAGTACCC
AGACAGAATCATGAGCTCATTCTCGGTTGTACCATCGCCAAAGGTGTCCGACACAGT
TGTAGAACCATACAATGCCACCCTCTCCGTCCACCAGCTTGTTGAGAACACCGATGA
GACCTACTGCATT (SEQ ID NO 77)

Figure 82: *Magnaporthe grisea* tubulin with Nun recognition sequence (bold and underlined)
CAGTTGATTTGTCTGCTGAAAAGACGGCTCTTGCACGTGGAGTCTATCGGCTGCAAT
ATGTGAGAGAGCGCCGTTATCCAGCACCACCACCGAGTCGGCATTCTGTGTCAATCT
CCTCATGGCTAGGATGCTGTTGTAGGGATGGACGACGACGTCTCCGGCATTCTGGG
TATCCGGAAATACCGAATACGTTTGTATGATCTTCTTGGGAAATCGGTCATTTAGCCT
TTCCAAGAGGAATGAGCCCAGACCTGAGCCTGTGCCACCAGCAATCGAATGCAGCA
TCATAAAGCCCTCGAGTGAGTCGCTTCCATCTGCTTCCCTATCAATCATCTCCATAAT
GGCCCTGAAAAAGGGCCATTATGGAGATGATTGATAGGGAAGCAGATGGAAGCGAC
TCACTCGAGGGCTTTATGATGCTGCATTCGATTGCTGGTGGCACAGGCTCAGGTCTG
GGCTCATTCCTCTTGGAAAGGCTAAATGACCGATTTCCCAAGAAGATCATACAAACGT
ATTCGGTATTTCCGGATACCCAGAATGCCGGAGACGTCGTCGTCCATCCCTACAACA
GCATCCTAGCCATGAGGAGATTGACACAGAATGCCGACTCGGTGGTGGTGCTGGAT
AACGGCGCTCTCTCACATATTGCAGCCGATAGACTCCACGTGCAAGAGCCGTCTTTT
CAGCAGACAAATCAACTG (SEQ ID NO 78)

Figure 83: *Nilaparvata lugens* tubulin with Nun recognition sequence (bold and underlined)
CGATACAGTAGGTTTCATCGGTGTTTTCGACGAGCTGATGAACGGAGAGGGTGGCAT
TGTATGGCTCGACAACTGTGTCGGATACCTTTGGTGAGGGCACAACGGAGTAGGTGT
TCATGATTCTGTCTGGGTATTCCTCGCGGATTTTCGAGATCAGCAATGTTCCCATTCC
TGATCCGGTACCACCTCCCAACGAATGAGTCAGCTGGAATCCCTGTAAGCAATCGCA
GCTCTCGGCTTCCTTTCTGACTACGTCGAGCCCTGAAAAAGGGCTCGACGTAGTCA
GAAAGGAAGCCGAGAGCTGCGATTGCTTACAGGGATTCCAGCTGACTCATTCGTTGG
GAGGTGGTACCGGATCAGGAATGGGAACATTGCTGATCTCGAAAATCCGCGAGGAA
TACCCAGACAGAATCATGAACACCTACTCCGTTGTGCCCTCACCAAAGGTATCCGAC
ACAGTTGTCGAGCCATACAATGCCACCCTCTCCGTTCATCAGCTCGTCGAAAACACC
GATGAAACCTACTGTATCG (SEQ ID NO 79)

Figure 84: *Meloidogyne incognita* tubulin with MS2 recognition sequence (bold and underlined)
CGATGCAGTAAGTCTCGTCGGTGTTCTCAACAAGTTGATGAACAGAAAGAGTTGCGT
TGTAGGGCTCAACGACCGTGTCAGAGACCTTAGGCGACGGAACAACAGAGAAGGAA
GACGTAATGCGGTCCGGATACTCCTCACGAATCTTTGAAATGAGCAAAGTTCCCATT
CCAGAGCCAGTTCCACCACCAAGCGAGTGAGTCAATTGAAAACCTTGAAGACAATCA
CAACCCTCAGCCTCTTTTCGAACAACATCCAACATGAGGATCACCCATGATGGATGT
TGTTCGAAAAGAGGCTGAGGGTTGTGATTGTCTTCAAGGTTTTCAATTGACTCACTCG
CTTGGTGGTGGAACTGGCTCTGGAATGGGAACTTTGCTCATTTCAAAGATTCGTGAG
GAGTATCCGGACCGCATTACGTCTTCCTTCTCTGTTGTTCCGTCGCCTAAGGTCTCT
GACACGGTCGTTGAGCCCTACAACGCAACTCTTTCTGTTCATCAACTTGTTGAGAACA
CCGACGAGACTTACTGCATCG (SEQ ID NO 80)

Figure 85: *Caenorhabditis elegans* tubulin with MS2 recognition sequence (bold and underlined)
AATGCAGTAGGTCTCATCGGTGTTCTCAACAAGCTGGTGGACGGAGAGGGTGGCAT
TGTATGGTTCTACAACTGTGTCGGACACCTTTGGCGATGGTACAACCGAGAATGAGC
TCATGATTCTGTCTGGGTACTCTTCGCGGATTTTGGAGATGAGAAGTGTTCCCATTCC
AGATCCGGTTCCTCCTCCGAGAGAGTGAGTGAGTTGGAATCCTTGAAGACAATCGCA
TCCTTCGGCTTCCTTGCGGATCACGTCACATGAGGATCACCCATGAGACGTGATCC
GCAAGGAAGCCGAAGGATGCGATTGTCTTCAAGGATTCCAACTCACTCACTCTCTCG
GAGGAGGAACCGGATCTGGAATGGGAACACTTCTCATCTCCAAAATCCGCGAAGAGT
ACCCAGACAGAATCATGAGCTCATTCTCGGTTGTACCATCGCCAAAGGTGTCCGACA
CAGTTGTAGAACCATACAATGCCACCCTCTCCGTCCACCAGCTTGTTGAGAACACCG
ATGAGACCTACTGCATT (SEQ ID NO 81)

Figure 86: *Magnaporthe grisea* tubulin with MS2 recognition sequence (bold and underlined)
CAGTTGATTTGTCTGCTGAAAAGACGGCTCTTGCACGTGGAGTCTATCGGCTGCAAT
ATGTGAGAGAGCGCCGTTATCCAGCACCACCACCGAGTCGGCATTCTGTGTCAATCT
CCTCATGGCTAGGATGCTGTTGTAGGGATGGACGACGACGTCTCCGGCATTCTGGG
TATCCGGAAATACCGAATACGTTTGTATGATCTTCTTGGGAAATCGGTCATTTAGCCT
TTCCAAGAGGAATGAGCCCAGACCTGAGCCTGTGCCACCAGCAATCGAATGCAGCA
TCATAAAGCCCTCGAGTGAGTCGCTTCCATCTGCTTCCCTATCAATCATCTCCATAAT
GACATGAGGATCACCCATGACATTATGGAGATGATTGATAGGGAAGCAGATGGAAG
CGACTCACTCGAGGGCTTTATGATGCTGCATTCGATTGCTGGTGGCACAGGCTCAGG
TCTGGGCTCATTCCTCTTGGAAAGGCTAAATGACCGATTTCCCAAGAAGATCATACAA
ACGTATTCGGTATTTCCGGATACCCAGAATGCCGGAGACGTCGTCGTCCATCCCTAC
AACAGCATCCTAGCCATGAGGAGATTGACACAGAATGCCGACTCGGTGGTGGTGCT
GGATAACGGCGCTCTCTCACATATTGCAGCCGATAGACTCCACGTGCAAGAGCCGTC
TTTTCAGCAGACAAATCAACTG (SEQ ID NO 82)

Figure 87: *Nilaparvata lugens* tubulin with MS2 recognition sequence (bold and underlined)
CGATACAGTAGGTTTCATCGGTGTTTTCGACGAGCTGATGAACGGAGAGGGTGGCAT
TGTATGGCTCGACAACTGTGTCGGATACCTTTGGTGAGGGCACAACGGAGTAGGTGT
TCATGATTCTGTCTGGGTATTCCTCGCGGATTTTCGAGATCAGCAATGTTCCCATTCC
TGATCCGGTACCACCTCCCAACGAATGAGTCAGCTGGAATCCCTGTAAGCAATCGCA
GCTCTCGGCTTCCTTTCTGACTACGTCGAACATGAGGATCACCCATGATCGACGTAG
TCAGAAAGGAAGCCGAGAGCTGCGATTGCTTACAGGGATTCCAGCTGACTCATTCGT
TGGGAGGTGGTACCGGATCAGGAATGGGAACATTGCTGATCTCGAAAATCCGCGAG
GAATACCCAGACAGAATCATGAACACCTACTCCGTTGTGCCCTCACCAAAGGTATCC
GACACAGTTGTCGAGCCATACAATGCCACCCTCTCCGTTCATCAGCTCGTCGAAAAC
ACCGATGAAACCTACTGTATCG (SEQ ID NO 83)

Figure 88: *Caenorhabditis elegans unc-22* with LicT recognition sequence(bold and underlined)
AGTCAGTAACCTCTGGTTTGTCAACTGGATCAGGAACATCAAATTGATTCTTTGCAAT
AATTGGTTCTTCAGCTTCCAATGGTTTTGATTCTCCTTGAAGATTGACTGCCTTGACA
CGGAATGCGTATTCCTTTCCAGGAACAAGCTTATTAACCTTGGCTGTACAATCTGGGA
AAGTTCCGACTTCCTGCCATGTTCCACGAGAAGTATCCATCTTCTCAACAATGTAGTG
AAGAACATCAGTTCCTCCGTTATCAGTTGGAGGCTTCCAGTTCAATGTACATCCTTCC
TTATGGATCTCGTCAATCTTGAGTGGTCCTTCTGGAGTTCCTGGTACATCAAGAACAG
TAACATTGCACTGAGCAGTATCTTTTCCATGCTCATTTTCAACAATGATTTTGTAAACT
CCAGTATCTCCACGGATTGTTACTGCGAAAGCAGGCAAAACCGTGGAGATACTGGA
GTTTACAAAATCATTGTTGAAAATGAGCATGGAAAAGATACTGCTCAGTGCAATGTTA
CTGTTCTTGATGTACCAGGAACTCCAGAAGGACCACTCAAGATTGACGAGATCCATA
AGGAAGGATGTACATTGAACTGGAAGCCTCCAACTGATAACGGAGGAACTGATGTTC
TTCACTACATTGTTGAGAAGATGGATACTTCTCGTGGAACATGGCAGGAAGTCGGAA
CTTTCCCAGATTGTACAGCCAAGGTTAATAAGCTTGTTCCTGGAAAGGAATACGCATT
CCGTGTCAAGGCAGTCAATCTTCAAGGAGAATCAAAACCATTGGAAGCTGAAGAACC
AATTATTGCAAAGAATCAATTTGATGTTCCTGATCCAGTTGACAAACCAGAGGTTACT
GACT (SEQ ID NO 84)

Figure 89: *Caenorhabditis elegans unc-22* with Nun recognition sequence (bold and underlined)
AGTCAGTAACCTCTGGTTTGTCAACTGGATCAGGAACATCAAATTGATTCTTTGCAAT
AATTGGTTCTTCAGCTTCCAATGGTTTTGATTCTCCTTGAAGATTGACTGCCTTGACA
CGGAATGCGTATTCCTTTCCAGGAACAAGCTTATTAACCTTGGCTGTACAATCTGGGA
AAGTTCCGACTTCCTGCCATGTTCCACGAGAAGTATCCATCTTCTCAACAATGTAGTG
AAGAACATCAGTTCCTCCGTTATCAGTTGGAGGCTTCCAGTTCAATGTACATCCTTCC
TTATGGATCTCGTCAATCTTGAGTGGTCCTTCTGGAGTTCCTGGTACATCAAGAACAG
TAACATTGCACTGAGCAGTATCTTTTCCATGCTCATTTTCAACAATGATTTTGTAAACT
CCAGTATCTCCACGCCCTGAAAAAGGGCGTGGAGATACTGGAGTTTACAAAATCATT
GTTGAAAATGAGCATGGAAAAGATACTGCTCAGTGCAATGTTACTGTTCTTGATGTAC
CAGGAACTCCAGAAGGACCACTCAAGATTGACGAGATCCATAAGGAAGGATGTACAT
TGAACTGGAAGCCTCCAACTGATAACGGAGGAACTGATGTTCTTCACTACATTGTTGA
GAAGATGGATACTTCTCGTGGAACATGGCAGGAAGTCGGAACTTTCCCAGATTGTAC
AGCCAAGGTTAATAAGCTTGTTCCTGGAAAGGAATACGCATTCCGTGTCAAGGCAGT
CAATCTTCAAGGAGAATCAAAACCATTGGAAGCTGAAGAACCAATTATTGCAAAGAAT
CAATTTGATGTTCCTGATCCAGTTGACAAACCAGAGGTTACTGACT (SEQ ID NO 85)

Figure 90: *Caenorhabditis elegans unc-22* with MS2 recognition sequence (bold and underlined)
AGTCAGTAACCTCTGGTTTGTCAACTGGATCAGGAACATCAAATTGATTCTTTGCAAT
AATTGGTTCTTCAGCTTCCAATGGTTTTGATTCTCCTTGAAGATTGACTGCCTTGACA
CGGAATGCGTATTCCTTTCCAGGAACAAGCTTATTAACCTTGGCTGTACAATCTGGGA
AAGTTCCGACTTCCTGCCATGTTCCACGAGAAGTATCCATCTTCTCAACAATGTAGTG
AAGAACATCAGTTCCTCCGTTATCAGTTGGAGGCTTCCAGTTCAATGTACATCCTTCC
TTATGGATCTCGTCAATCTTGAGTGGTCCTTCTGGAGTTCCTGGTACATCAAGAACAG
TAACATTGCACTGAGCAGTATCTTTTCCATGCTCATTTTCAACAATGATTTTGTAAACT
CCAGTATCTCCACACATGAGGATCACCCATGAGTGGAGATACTGGAGTTTACAAAAT
CATTGTTGAAAATGAGCATGGAAAAGATACTGCTCAGTGCAATGTTACTGTTCTTGAT
GTACCAGGAACTCCAGAAGGACCACTCAAGATTGACGAGATCCATAAGGAAGGATGT
ACATTGAACTGGAAGCCTCCAACTGATAACGGAGGAACTGATGTTCTTCACTACATTG
TTGAGAAGATGGATACTTCTCGTGGAACATGGCAGGAAGTCGGAACTTTCCCAGATT
GTACAGCCAAGGTTAATAAGCTTGTTCCTGGAAAGGAATACGCATTCCGTGTCAAGG
CAGTCAATCTTCAAGGAGAATCAAAACCATTGGAAGCTGAAGAACCAATTATTGCAAA
GAATCAATTTGATGTTCCTGATCCAGTTGACAAACCAGAGGTTACTGACT (SEQ ID NO 86)

Figure 91: amino acid sequence corresponding to the N-terminal domain of bacteriophage λ N protein comprising amino acids 1 to 36
MDAQTRRRERRAEKQAQWKAANPLLVGVSAKPVNRP (SEQ ID NO 87).

… (1)

METHOD AND CONSTRUCTS FOR DELIVERING DOUBLE STRANDED RNA TO PEST ORGANISMS

RELATED APPLICATIONS

This application is a national stage filing under 35 U.S.C. §371 of international application PCT/EP2005/011441, filed Oct. 25, 2005, which was published under PCT Article 21(2) in English, and claims priority under 35 U.S.C. §119(e) to U.S. provisional application 60/621,718, filed Oct. 25, 2004 and to U.S. provisional application 60/628,976, filed Nov. 18, 2004, the disclosures of which are incorporated herein by reference.

FIELD OF THE INVENTION

The present invention relates generally to RNAi and its use in gene silencing. Furthermore, the present invention relates to methods and constructs for delivering double stranded RNA (dsRNA) to pest organisms.

BACKGROUND

Targeted inhibition of gene expression has been a long-felt need in biotechnology and genetic engineering. In the last few years, advances in nucleic acid chemistry and gene transfer have inspired new approaches to engineer specific interference with gene expression.

One of these approaches consists of double-stranded RNA inhibition (RNAi) as a tool for controlling gene expression, as described in WO 99/32619 and WO 00/01846. Double-stranded RNA inhibition is based on the introduction of RNA into a living cell to inhibit gene expression of a target gene in that cell. The RNA has a region with double-stranded structure. Double-stranded RNA (dsRNA) has the capability to render genes nonfunctional in a sequence-specific manner. When introduced into cells, dsRNA can activate mechanisms that target the degradation of cognate cytoplasmic mRNAs and thus can effectively silence full gene expression at the posttranscriptional level. RNAi has been observed in many cell types from divergent eukaryotes, including protozoa, fungi, plants, invertebrates, and mammals. Once inside the cells, long dsRNA molecules are cleaved into double-stranded small interfering RNAs (siRNAs) that are 21-25 base pairs in length by an enzyme with RNaseIII-like activity (Dicer). Cleavage into siRNAs is an early step in the RNAi silencing mechanism. Introduction of double-stranded RNA (dsRNA) can elicit a gene-specific RNA interference response in a variety of organisms and cell types.

In plants this technology may be used for instance with the aim of modifying or improving plant resistance towards pathogens and pests. The latter technique may involve the uptake of the dsRNA by pest organisms when feeding on the plants. In delivery by feeding, dsRNA may be distributed to cells from the gut of the feeding organism in the same manner as nutrients. It is also conceivable that dsRNA residing in "infected" cells could undergo successive rounds of cellular exit and re-entry into adjacent "uninfected" cells.

However, delivery of dsRNA to pest organisms by feeding has limits. Difficulties related to the delivery of dsRNA to feeding target organisms are numerous and may for instance involve the need to use very high amounts of dsRNA in order to be effective. Also, dsRNA may easily break down in the plants or during delivery to the target organism. Furthermore, in order to be effective, the dsRNA molecules should efficiently be taken up by the pest and delivered to the correct targeting site in the pest organisms.

Since the advent of double-stranded RNA inhibition there has been recognized a need for specialized constructs designed for site-directed delivery of double-stranded RNA in a pest organism. While there are various methods available for directly and indirectly introducing dsRNA into cells, it is clear that these methods are generally inefficient, and have practical limitation. Therefore, in view of the foregoing, there exists a need to develop tools and methods for the more efficient delivery of dsRNA into pest cells for the purpose of achieving RNAi and to kill or paralyze the pest. The present invention aims to provide improved methods and constructs useful in the delivery of double-stranded RNA in pest organisms, including nematodes, insects and fungi. An object of the present invention is thus to provide dsRNA constructs with improved properties to be effectively taken up in the cells or tissues of the pest species.

Insect, fungal and nematode pests are a major cause of damage to the world's commercially important agricultural crops. Current strategies aimed at reducing crop losses rely primarily on chemical pesticides. Alternatively transgenic crops with intrinsic pest resistance offer a promising alternative and continue to be developed. Pest-resistant plants can reduce pest population growth, the number of pesticide applications and the environmental impact of pesticides. There remains a great need in the art for plants showing resistance to pest organisms. Another object of the present invention is therefore to provide pest resistant plants showing resistance to pest organisms such as nematodes, insects and fungi.

SUMMARY

The present invention provides delivery molecules for facilitating the delivery of a double-stranded ribonucleic acid molecule to a pest organism, as well as various uses of the delivery molecule. The present invention also provides complexes of the delivery molecule and chimeric RNAi molecules, i.e. RNA molecules comprising double stranded RNA for the purpose of RNA interference.

Specifically, in a first aspect the present invention relates to an RNA delivery molecule consisting of a polypeptide sequence comprising (i) at least one RNA-binding domain, (ii) at least one targeting polypeptide able to bind to a cellular endocytosis and/or transcytosis receptor molecule and (iii) optionally at least one peptide linker and/or at least one purification tag.

The advantages of the present invention include: the ease of introducing double-stranded RNA into cells or tissues, the low concentration of RNA which can be used, the stability of double-stranded RNA, and the effectiveness of the inhibition. The present invention allows for the introduction of a double-stranded RNA molecule, such as a small interfering RNA, into a cell of a pest organism with greater ease and efficiency than previously possible using conventional methods known in the art. Accordingly, the RNA delivery molecule of the present invention provides a powerful tool for various agronomic and research applications requiring the delivery of dsRNA into a target pest organism.

In another embodiment, the invention relates to a chimeric RNAi molecule comprising
    at least one nucleotide sequence recognized by an RNA-binding protein or RNA-binding domain, and,
    at least one nucleotide sequence corresponding to a target nucleotide sequence of a target gene of a pest species.

The invention further also relates to a complex comprising an RNA delivery molecule as defined herein and a chimeric RNAi molecule as defined herein.

The present invention further provides various methods of using an RNA delivery molecule described herein, including methods of facilitating delivery of a double-stranded ribonucleic acid molecule into a pest organism. In a second aspect, the present invention therefore relates to a method for delivering a dsRNA molecule to a pest species, comprising co-expressing in a plant cell of
(a) an RNA delivery molecule according to the present invention, and
(b) an RNA molecule which comprises double-stranded RNA comprising annealed complementary strands, one of which has a nucleotide sequence which is complementary to at least part of a target nucleotide sequence of a target gene of the pest species, and which further comprises a nucleotide sequence which binds to the RNA-binding domain of the RNA delivery molecule of (a) to induce RNAi, and feeding said plant cell to said pest species, and thereby increasing the resistance of the plant (cell) towards the feeding pest.

The present invention also relates to methods for down-regulating expression of a target gene in a pest species. In an embodiment such method for down-regulating expression of a target gene in a pest species comprises:

co-expressing in a plant cell of
a) an RNA delivery molecule according to the present invention, and
b) an RNA molecule which comprises double-stranded RNA comprising annealed complementary strands, one of which has a nucleotide sequence which is complementary to at least part of a target nucleotide sequence of the target gene to be down-regulated, and which further comprises a nucleotide sequence which binds to the RNA-binding domain of the RNA delivery molecule of (a), and feeding said plant cell to said pest species, and thereby increasing the resistance of the plant (cell) towards the feeding pest.

In an embodiment, the chimeric RNAi molecule consists of an RNA molecule which comprises double-stranded RNA comprising annealed complementary strands, one of which has a nucleotide sequence which is complementary to at least part of a target nucleotide sequence of the target gene, and which further comprises a nucleotide sequence which binds to the RNA-binding domain of the RNA delivery molecule.

In another embodiment, the invention provides a method for down-regulating expression of a target gene in a pest species which comprises:

co-expressing in a plant cell of a complex comprising an RNA delivery molecule as defined herein and a chimeric RNAi molecule comprising of at least one nucleotide sequence recognized by an RNA-binding protein or RNA-binding domain of said RNA delivery molecule and, at least one nucleotide sequence is complementary to at least part of a target nucleotide sequence of a target gene of a pest species, and feeding said plant cell to said pest species, and thereby increasing the resistance of the plant (cell) towards the feeding pest.

Another aspect of the invention relates to methods for producing a transgenic plant that is resistant to a pest species, comprising:

co-expressing in a plant cell of:
a) an RNA delivery molecule according to the present invention, and
b) an RNA molecule which comprises double-stranded RNA comprising annealed complementary strands, one of which has a nucleotide sequence which is complementary to at least part of a target nucleotide sequence of the target gene of said pest species, and which further comprises a nucleotide sequence which binds to the RNA-binding domain of the RNA delivery molecule of (a), and a regenerating a plant from said plant cell.

In another embodiment, the invention provides a method for producing a transgenic plant that is resistant to a pest species, comprising:

co-expressing in a plant cell of a complex comprising an RNA delivery molecule as defined herein and a chimeric RNAi molecule comprising of at least one nucleotide sequence recognized by an RNA-binding protein or RNA-binding domain of said RNA delivery molecule and, at least one nucleotide sequence corresponding to a target nucleotide sequence of a target gene of a pest species, and regenerating a plant from said plant cell.

In yet another aspect the present invention also relates to the use of an RNA delivery molecule according to the present invention for delivery of a dsRNA molecule to a pest species and in particular to a target sequence in a pest species.

In yet another aspect the present invention also relates to the use of an RNA delivery molecule according to the present invention for producing a transgenic plant.

In another aspect the present invention also relates to the use of a complex comprising an RNA delivery molecule as defined herein and a chimeric RNAi molecule as defined herein for down-regulating expression of a target gene in a pest species.

In yet another aspect the present invention further relates to the use of a complex comprising an RNA delivery molecule as defined herein and a chimeric RNAi molecule as defined herein for producing a transgenic plant, and for producing a transgenic plant that is resistant to a pest species.

In another aspect, the present invention further relates to a nucleic acid encoding an RNA delivery molecule of the invention and to a vector comprising said nucleic acid.

In another aspect, the present invention provides a host cell which comprises a nucleic acid encoding an RNA delivery molecule of the invention or a vector comprising said nucleic acid.

In another aspect, the present invention relates to a kit comprising at least one RNA delivery molecule as defined herein.

In another aspect, the invention relates to a composition comprising at least one RNA delivery molecule as defined herein. Preferably, the invention also relates to a composition comprising a) at least one RNA delivery molecule as defined herein, and
b) at least one RNA molecule which comprises double-stranded RNA comprising annealed complementary strands, one of which has a nucleotide sequence which is complementary to at least part of a target nucleotide sequence of a target gene of a pest species, and which further comprises a nucleotide sequence which binds to the RNA-binding domain of the RNA delivery molecule of (a).

Preferably, the composition or kit according to the invention further comprise at least one excipient, e.g. an excipient which is suitable for keeping the RNA delivery molecule or the composition in a stabile condition.

The present invention further relates in another aspect to a transgenic plant resistant to a pest species, an essential derived variety thereof, plant part, plant cell or protoplast thereof obtainable by methods according to the present invention.

The invention also provides a transgenic plant, essentially derived variety thereof, plant part, plant cell or protoplast thereof which comprises a nucleic acid encoding an RNA delivery molecule as defined herein, wherein said nucleic acid is heterologous to the genome of said transgenic plant, or an essentially derived variety thereof, plant part, plant cell or plant protoplast thereof.

The invention also provides a transgenic plant which comprises a vector comprising a nucleic acid encoding an RNA delivery molecule of the invention.

The invention further relates to a plant, essentially derived variety thereof, plant part, plant cell or protoplast thereof wherein the plant essentially derived variety thereof, plant part, plant cell or protoplast thereof has been transformed with a nucleic acid encoding an RNA delivery molecule as defined herein.

In another aspect, the invention relates to a plant, essentially derived variety thereof, plant part, plant cell or protoplast thereof which co-expresses:
a) an RNA delivery molecule according to the present invention, and
b) an RNA molecule which comprises double-stranded RNA comprising annealed complementary strands, one of which has a nucleotide sequence which is complementary to at least part of a target nucleotide sequence of a target gene in a pest species, and which further comprises a nucleotide sequence which binds to the RNA-binding domain of the RNA delivery molecule of (a).

In further embodiments, the present invention relates to progeny or parts or derivatives of plants obtained from a plant or essentially derived variety thereof according to the present invention.

In yet another aspect the present invention also relates to a chimeric RNAi molecule comprising a nucleotide sequence recognized by an RNA-binding protein or RNA-binding domain, and a nucleotide sequence corresponding to a target nucleotide sequence of a target gene of a pest species.

Additional aspects of the present invention will be apparent in view of the detailed description, which follows.

DESCRIPTION OF THE FIGURES

FIGS. 1 to 14 illustrate the nucleotide and amino acid sequences of RNA binding polypeptides according to the present invention.

FIGS. 15 to 40 illustrate RNA sequences binding to the respective RNA binding polypeptides according to the present invention.

FIGS. 43 to 54 and 56 to 58 and 60 to 74 and 76 to 90 illustrate several examples of chimeric RNAi molecules according to the present invention (SEQ ID NOs 41 to 52 and SEQ ID NOs 54 to 56 and SEQ ID NOs 57 to 71 and SEQ ID NOs 72 to 86).

FIG. 55 is a schematic representation of a a chimeric RNAi molecule according to the present invention, as further represented in any of SEQ ID NOs 41 to 52 and any of SEQ ID NOs 54 to 56.

FIG. 59 is another schematic representation of a chimeric RNAi molecule according to the present invention, as further represented in any of SEQ ID NOs 57 to 71.

FIG. 75 is yet another schematic representation of a chimeric RNAi molecule according to the present invention, as further represented in any of SEQ ID NOs 72 to 86.

FIG. 91 represents the amino acid sequence of an RNA binding polypeptide according to the present invention, in particular of the N-terminal domain of bacteriophage λ N protein comprising amino acids 1 to 36 (SEQ ID NO 87).

DETAILED DESCRIPTION OF THE INVENTION

Figure 41:
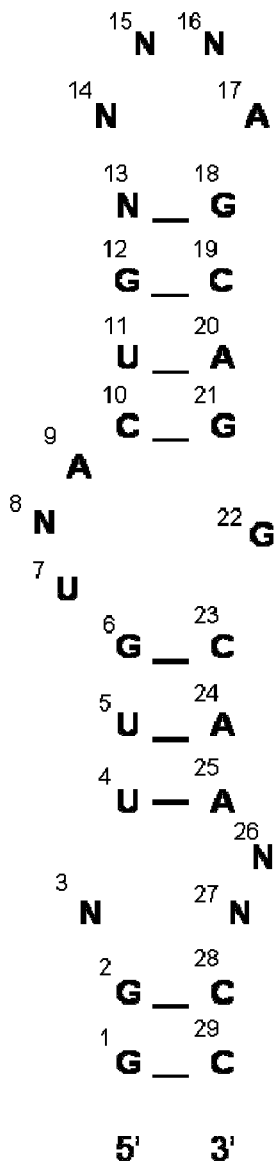
FIG. 41 illustrates the consensus secondary structure in the *Bacillus subtilis* ribonucleic anti-terminator (RAT; SEQ ID NO:34) reacting with the LicT RNA-binding domain.

The present invention describes an RNA delivery molecule for facilitating the delivery of double-stranded RNA into a target organism, as well as various uses thereof. Specifically, it has been found that RNA delivery molecule may be bound to a double-stranded ribonucleic acid molecule by means of linkage to an RNA binding domain to form a complex between a protein moiety, e.g. the RNA delivery molecule, and a nucleic acid moiety, e.g. an RNA molecule comprising the double stranded RNA that causes interference. Such RNA delivery molecule greatly facilitates uptake efficiency and allows for the efficient in vivo delivery of dsRNA into cells, or tissues of target pest organisms.

While the present invention is primarily directed to the delivery of a double-stranded ribonucleic acid molecule into a pest organism for the purposes of RNA interference, the RNA delivery molecules described herein may also be used to facilitate the delivery of other non-coding RNAs, such as small temporal RNAs, small nuclear RNAs, small nucleolar RNAs or microRNAs, which may be used in applications other than RNA interference.

A. RNA Delivery Molecule

In accordance with the present invention, a delivery promoting molecule is used to facilitate the uptake and the correct delivery of double stranded RNA to a suitable target site in a plant-feeding pest organism for the purpose of RNA interference.

The terms "RNA delivery module", "RNA delivery molecule" and "RNA delivery vehicle" are used herein as synonym and refer to the multidomain or multimodular protein which binds to an RNAi mediating molecule.

The term "RNAi" generally means "RNA interference".

In one embodiment of the present invention, the RNA delivery molecule consists of a polypeptide sequence which comprises:
i) at least one RNA binding domain,
ii) at least one targeting polypeptide able to be endocytosed and/or transcytosed or able to bind to a cellular endocytosis and/or transcytosis receptor molecule
iii) optionally at least one peptide linker for linking the RNA binding domain to the targeting polypeptide, and
iv) optionally a module comprising a purification tag.

The expression "at least one" in the context of the present invention means at least two, at least three, at least four, at least five, at least six, etc. and up to at least 10 or at least 15.

These modules can be swapped spatially. For example, the RNA binding domain can be at the N-terminus of the targeting polypeptide or can be at the C-terminus of the targeting polypeptide. The purification module can be at the N-terminus or at the C-terminus of the RNA delivery molecule. Not all modules need to be present. For example, for protein isolation the fourth module is included whereas for in vivo expression it can be present or absent. The separate modules comprised in the RNA delivery molecule will be discussed into more detail hereunder.

In a specific embodiment the invention relates to an RNA delivery molecule consisting of a polypeptide sequence comprising (i) at least one RNA-binding domain, (ii) at least one targeting polypeptide able to bind to a cellular endocytosis and/or transcytosis receptor molecule and (iii) optionally at least one peptide linker.

RNA-Binding Module

More in particular, a first module in the RNA delivery molecule according to the present invention comprises an RNA binding module. This module permits to specifically bind RNA to the RNA delivery molecule. The terms "RNA binding module", "RNA binding molecule" and "RNA binding protein" are used herein as synonym and refer to a protein or an essential part, or a homologue thereof, which is capable of binding RNA. The RNA binding molecule comprises an "RNA binding domain". An "RNA binding domain" as used herein may bind double-stranded RNA generically or specifically, single-stranded RNA generically or specifically. The RNA binding molecule may bind dsRNA, ssRNA structure specifically.

The term "essential parts thereof" or "functional part thereof" in this context refers to parts of RNA binding proteins which are capable of binding dsRNA, ssRNA or which recognize and bind a secondary structure in an RNA.

The term "homologue" of an RNA binding protein as used herein refers to a protein which has an amino acid sequence that has at least 30% identity, preferably at least 40%, 50%, 60%, 70%, 80% or 90% identity, most preferably at least 95% identity with a functional portion of the amino acid sequence of an RNA binding protein. It should be understood that instead of % "identity", also the corresponding % "similarity" can be used to define homologues according to the invention.

The term "functional portion" in the context of the present invention means a portion or fragment of the RNA binding protein comprising the RNA-binding domain.

As used herein, the "% identity and % similarity" are calculated using matcher (EMBOSS, based on Bill Pearson's 'lalign' application, version 2.0u4 Feb. 1996). Lalign is based on an algorithm developed by X. Huang and W. Miller (Adv. Appl. Math. (1991) 12:337-357) for the "sim" program, which is a linear-space version of an algorithm described by M. S. Waterman and M. Eggert (J. Mol. Biol. (1987) 197:723-728). A EBLOSUM62 was used as a substitution matrix, and a gap penalty of 14 and an extended penalty of 4 for the alignment.

For the purpose of the present invention, the RNA binding protein or RNA binding domain binds an RNA molecule comprising the double-stranded RNA causing interference in a pest species. The RNA binding domain may bind directly to said double-stranded RNA causing interference, through recognition of and binding to one or more RNA sequences within said double-stranded RNA, or through recognition of and binding to an RNA structure within said double-stranded RNA. Alternatively, the RNA molecule comprising the double-stranded RNA causing interference comprises a further RNA sequence which is recognized by the RNA binding protein or RNA binding domain as being a binding site specific for the said RNA binding protein or domain. Said further RNA sequence may be double-stranded, single-stranded or may comprise an RNA structure which is specifically recognized and bound by the RNA binding protein or RNA binding domain.

It should be noted that each of the RNA binding proteins or RNA binding domains may bind to specific RNA sequences, patterns, recognition sites, RNA structures or the like.

Preferred examples of RNA binding proteins include but are not limited to coliphage HK022 Nun protein, *Bacillus subtilis* LicT protein, or bacteriophage MS2 coat protein or essential parts, or homologues thereof.

In a preferred embodiment, the RNA binding module comprises the coliphage HK022 Nun protein (Genbank entries: nucleotide sequence: X16093 (whole viral sequence); amino acid sequence: P18683, VNBPHK) or essential parts thereof. The nucleotide and amino acids sequences corresponding to the gene encoding the coliphage HK022 Nun protein are illustrated in FIGS. 1 (SEQ ID NO 1) and 2 (SEQ ID NO 2), respectively. The HK022 Nun of phage HK022 is a transcription termination factor that acts highly template and site specific. Nun terminates transcription uniquely on phage lambda templates, thereby in competition with lambda N protein for the common binding site, the nut boxB RNA. This is a 15-mer RNA hairpin containing a purine-rich pentaloop. Nun protein, as the N protein, belongs to a family of arginine-rich motif binding proteins. They bind to the major groove of the boxB RNA, which adopts a typical hairpin confirmation closed by an apical tetraloop (Faber et al., J. Biol. Chem., 2001, 276, 32064 and reference therein). The protein is an alpha helix connecting to the hairpin of the RNA. There is a high and specific affinity of the RNA binding domain in the Nun protein towards the boxbRNA. The peptide structure seems highly charged while the RNA is rich in purines. Both are quite special entities.

In another preferred embodiment the RNA binding module comprises essential parts (for instance comprising any of SEQ ID Nos 4, 6 or 8) of the coliphage HK022 Nun protein. Preferred examples hereof comprise but are not limited to:

the N-terminal domain of coliphage HK022 Nun protein 1 to 47 (SEQ ID NO 4) comprising the RNA-binding domain, the N-terminal domain of coliphage HK022 Nun protein 13 to 47 (SEQ ID NO 6) comprising the RNA-binding domain, the N-terminal domain of coliphage HK022 Nun protein 22 to 47 (SEQ ID NO 8) comprising the RNA-binding domain, In yet another preferred embodiment the RNA binding module comprises proteins belonging to the same arginine-rich motif (ARM) family as coliphage HK022 Nun protein such as for instance bacteriophage λ N protein, or RNA binding domains of proteins belonging to the same arginine-rich motif (ARM) family as coliphage HK022 Nun such as for instance the N-terminal domain of bacteriophage λ N protein comprising amino acids 1 to 36 (as represented in SEQ ID NO 87) or amino acids 1 to 22.

In another preferred embodiment the RNA binding module comprises homologues of the coliphage HK022 Nun protein. Therefore, according to a further embodiment, the invention also relates to an RNA delivery molecule as described above, wherein said at least one RNA-binding domain comprises a polypeptide having at least 30% identity, preferably at least 40%, 501%, 60%, 70%, 80% or 90% identity, most preferably at least 95% identity with the coliphage HK022 Nun protein (or with the polypeptide as represented in SEQ ID NO 2). It should be understood that instead of % "identity", also the corresponding % "similarity" can be used to define homologues according to the invention.

In a preferred example, the N-terminal binding-domain of the bacteriophage HK022 Nun protein (SEQ ID NO 2) and in particular the peptide with sequence SEQ ID NO 8 interacts with the box B RNA sequence (SEQ ID NO 15) and in particular with the 11mer RNA sequence represented in SEQ ID NO 16. (Scharpf et al., Eur. J. Biochem. 267, p 2397 (2000), Faber et al., J. Biol. Chem. 276, 34, p 32064 (2001)).

In another embodiment, the RNA binding module comprises the *Bacillus subtilis* LicT protein or essential parts thereof (Genbank/Swissprot/PIR entries: nucleotide sequence: Z28340 (D83026, Z99124 for larger genomic fragments); amino acid sequence: P39805, S47216, BAA11696, CAA82194). The nucleotide and amino acid sequences corresponding to the gene encoding the *subtilis* LicT protein are illustrated in FIGS. 9 (SEQ ID NO 9) and 10 (SEQ ID NO 10), respectively. The transcriptional anti-terminator LicT from *Bacillus subtilis* is a regulatory protein able to prevent the premature arrest of transcription. When activated, LicT binds to RNA of around 30 nucleotides. This RNA adopts a hairpin conformation containing a variable apical loop and two asymmetric internal loops. LicT belongs to a group of antiterminator proteins (involved in carbohydrate metabolism control in Gram-positive and Gram-negative bacteria) for which the RNA recognition is embedded in the N-terminal protein fragment. This domain binds as a beta-stranded symmetric dimer that shares no structural homology with other known RNA-binding motifs (EMBO; 2002, 21, 1987 and references therein). There is a high level of sequence identity both in the protein family as in the RNA sequence for the AA/nucleotides that interact with each other. Most of the conserved residues of the protein are in direct contact (hydrophobic or via Hbond donor/acceptor) with the RNA. Those which are not in contact do not seem to be important for RNA binding, but might play a role for intra-inter protein interactions during the anti-termination process. Nine AA (from position 5 till 31) interact with the RNA, all of them highly conserved. Six of them are crucial for the in vivo anti-terminal activity or in vitro RNA binding.

In another preferred embodiment the RNA binding module comprises essential parts (for instance comprising SEQ ID NO 12) of the *Bacillus subtilis* LicT protein. Preferred examples hereof comprise but are not limited to the N-terminal domain of *Bacillus subtilus* LicT protein comprising amino acids 1 to 56 (SEQ ID NO 12) containing the RNA-binding domain.

In yet another preferred embodiment the RNA binding module comprises
proteins belonging to the same anti-terminator (AT) family as *Bacillus subtilis* LicT protein such as for instance the *Bacillus subtilis* SacY protein or the *Escherichia coli* BglG protein,
the RNA binding domain of proteins belonging to the same anti-terminator (AT) family as *Bacillus subtilus* LicT protein such as for instance N-terminal domain of *Bacillus subtilis* SacY protein comprising amino acids 1 to 55 of the SacY protein or the N-terminal domain of *Escherichia coli* BglG protein comprising amino acids 4 to 60 of the BglG protein.

In another preferred embodiment the RNA binding module comprises homologues of the *Bacillus subtilis* LicT protein. Therefore, according to a further embodiment, the invention also relates to an RNA delivery molecule as described above, wherein said at least one RNA-binding domain comprises a polypeptide having at least 30% identity, preferably at least 40%, 50%, 60%, 70%, 80% or 90% identity, most preferably at least 95% identity with the *Bacillus subtilis* LicT protein (or with the polypeptide as represented in SEQ ID NO 10), preferably said RNA-binding domain comprises a polypeptide having at least 60% identity, preferably at least 70%, 80% or 90% identity, most preferably at least 95% identity with the RNA binding domain of the *Bacillus subtilis* LicT protein (i.e. with the polypeptide as represented in SEQ ID NO 12). A non-exhaustive list of such homologous polypeptides is given in Table 1, and may further include representative members of the LicT/SacY family of transcriptional ATs from *Bacillus subtilis, Bacillus stearothermophilus, Listeria mnocytogenes, Clostridium longisporum, Clostridium acetobutylicum, Staphylococcus carnosus, Streptococcus agalactiae, Lactococcus lactis, Lactobacillus casei, E. coli* and *Erwinia chrysanthemi*. It should be understood that instead of % "identity", also the corresponding % "similarity" can be used to define homologues according to the invention.

TABLE 1

Homologues of the *Bacillus subtilis* LicT protein

| Homologues | Identity * | Similarity * | Genbank accession number | accession number ** |
|---|---|---|---|---|
| Antiterminator [*Staphylococcus cornosus*] | 29.7 | 53.6 | 2632149 | CAA74358 |
| lact2 | 31.4 | 53.6 | 6016464 | P24401 |
| beta-glucoside operon antitermintator | 54.2 | 76.6 | 114108 | P26211 |
| cryptic beta-glucoside bgl operon antiterminator | 42.4 | 69.9 | 114961 | P11989 |
| hypothetical protein [*Streptococcus agalactiae*] | 40.4 | 66.7 | 2765188 | CAA72900 |
| Levansucrase and sucrase synthesis operon antiterminator | 37.4 | 64 | 134180 | P15401 |
| transcription antiterminator [*Geobacillus stearothermophilus*] | 38.6 | 65.7 | 1737500 | AAB38977 |
| SacPA operon antiterminator | 41.2 | 67.2 | 134178 | P26212 |
| transcription antiterminator; BgIR [*Enterococcus faecium*] | 37.9 | 62.5 | 4704716 | AAD28229 |
| regulatory protein [*Clostridium longisporum*] | 47.1 | 69.7 | 7304840 | AAC05712 |
| Antiterminator [*Listeria monocytogenes*] | 35.3 | 62.2 | 4138148 | CAA07716 |

TABLE 1-continued

Homologues of the *Bacillus subtilis* LicT protein

| Homologues | Identity * | Similarity * | Genbank accession number | accession number ** |
|---|---|---|---|---|
| BgIR | 41.5 | 63.2 | 551875 | AAA57135 |
| transcription antiterminator [*Bacillus subtilis*] | 31.4 | 60.6 | 2154723 | CAA72077 |
| antiterminator homolog [*Escherichia coli*] | 33.1 | 56.1 | 2197103 | AAB61291 |

* identity or similarity with the RNA-binding protein LicT.
** accession number according to other databases such as Swissprot or PIR In a preferred embodiment, the LicT RNA-binding domain (comprising SEQ ID NO 12) interacts with the *Bacillus subtilis* ribonucleic antiterminator (RAT) that has a secondary structure as depicted in FIG. 41 or binds to an RNA having a sequence as given in any of SEQ ID NOs 17 to 34 (Scharpf, Sticht et al., Eur. J. Biochem. 267, p 2397 (2000), Scharpf et al. 2002, Yang 2000). Any of SEQ ID NOs 17 to 33 corresponds with the RNA binding recognition site in the homologous protein in the representative members of the LicT/SacY family of transcriptional Ats from *Bacillus subtilis, Bacillus stearothermophilus, Listeria mnocytogenes, Clostridium longisporum, Clostridium acetobutylicum, Staphylococcus carnosus, Streptococcus agalactiae, Lactococcus lactis, Lactobacillus casei, E. coli* and *Erwinia chrysanthemi*. The 29-mer sequence recognition pattern for binding to LicT homologues is represented in FIG. 34 (SEQ ID NO: 34).

In yet another preferred embodiment, the RNA binding module comprises the bacteriophage MS2 coat protein or essential parts thereof (Genbank/Swisprot/PIR entries: nucleotide sequence: V00642 (whole genome), NC_001417 (whole genome); amino acid sequence: P03612, CAA23989, NP_040648, VCBPM2, 721932A). FIG. 13 (SEQ ID NO 13) and 14 (SEQ ID NO 14) illustrate the nucleotide and amino acid sequences of the gene encoding bacteriophage MS2 coat protein. A dimer of the MS2 coat protein binds specifically to a 19 nt long hairpin in the single stranded viral RNA genome which results in the repression of the replicase translation. The complex also functions as an initiation site for viral assembly and controls the encapsidation of the cognate RNA in vivo (Nucleic Acid Research, 2002, 30, 2678-2685, Nature, 1994, 13, 623-626 and references therein).

In another preferred embodiment the RNA binding module comprises essential parts (comprising the RNA binding domain) of the bacteriophage MS2 coat protein. Other preferred examples of suitable RNA binding modules according to the present invention may comprise but are not limited to coat proteins of other Leviviridae such as those of subgroup I, e.g. f2, R17, or subgroup II, e.g. JP34, RNA-binding domains of coat proteins of other Leviviridae (subgroup I, e.g. f2, R17, or subgroup II, e.g. JP34).

In another preferred embodiment the RNA binding module comprises homologues of the bacteriophage MS2 coat protein. Therefore, according to a further embodiment, the invention also relates to an RNA delivery molecule as described above, wherein said at least one RNA-binding domain comprises a polypeptide having at least 30% identity, preferably at least 40%, 50%, 60%, 70%, 80% or 90% identity, most preferably at least 95% identity with the bacteriophage MS2 coat protein (or with the polypeptide as represented in SEQ ID NO 14), preferably said RNA-binding domain comprises a polypeptide having at least 60% identity, preferably at least 70%, 80% or 90% identity, most preferably at least 95% identity with the RNA binding domain of the MS2 coat protein. A non-exhaustive list of such homologous polypeptides is given in Table 2. It should be understood that instead of % "identity", also the corresponding % "similarity" could be used to define homologues according to the invention.

TABLE 2

Homologues of the bacteriophage MS2 coat protein

| Homologous | Identity * | Similarity * | accession number ** |
|---|---|---|---|
| Coat protein bacteriophage R17 | 98 | 100 | PO3613 |
| Coat protein enterobacterio phage M12 | 98 | 98.4 | Q9T1C7 |
| Coat protein bacteriophage JP501 | 95 | 97.7 | Q9MCD7 |
| Coat protein bacteriophage Fr | 87 | 91.5 | P03614 |
| Coat protein bacteriophage Ku1 | 63 | 79.7 | Q9MBL2 |
| Coat protein bacteriophage JP34 | 65 | 78.9 | P34700 |
| Coat protein bacteriophage GA | 63 | 77.2 | P07234 |
| Coat protein enterobacterio phage MX1 | 24 | 48.6 | O64307 |
| Coat protein bacteriophage PRR1 | 30 | 45.4 | P03616 |
| Coat protein bacteriophage SP | 23 | 44.6 | P09673 |
| Coat protein bacteriophage M11 | 26 | 43.6 | O64303 |
| Coat protein bacteriophage Q-beta | 23 | 43.3 | P03615 |
| Coat protein enterobacteriol phage NL95 | 25 | 42.4 | O64310 |

Figure 42:
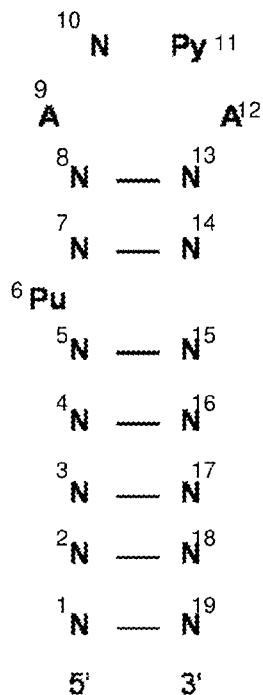
FIG. 42 illustrates the consensus secondary structure of RNA stem-loops (SEQ ID NO:40) that bind to bacteriophage MS2 coat protein.

* identity or similarity with the MS2 coat protein.
** accession number according to databases such as Genbank/Swissprot/PIR In a preferred embodiment, the bacteriophage MS2 coat protein (SEQ ID NO 14) interacts with RNA stem-loops that have a secondary structure as depicted in FIG. 42 or binds to RNA sequences having a sequence as given in any of SEQ ID NOs 35 to 40 (Rowsell et al., Nat. Struct. Biol. 5, 11, p 970, 1998). The sequence recognition pattern comprises: 5'-$N_1N_2N_3N_4N_5PuN_7N_8AN_{10}PyAN_{13}N_{14}N_{15}N_{16}N_{17}N_{18}N_{19}$-3' (SEQ ID NO 40); in this formula, $N_1$-$N_5$ are the reverse complementary of $N_{15}$-$N_{19}$ and $N_7$-$N_8$ are the reverse complementary of $N_{13}$-$N_{14}$, and preferably with the restriction that $N_6$ (Pu) does not pair with $N_{14}$.

The present invention thus relates to an RNA delivery molecule as described above, wherein said at least one RNA-binding domain (i) is chosen from:

a polypeptide comprising the coliphage HK022 Nun protein (for instance as represented in SEQ ID NO 2), a homologue thereof, or a fragment thereof comprising the RNA-binding domain, said fragment preferably comprising amino acids 1 to 47 (SEQ ID NO 4) of the aminoterminal sequence, more preferably comprising amino acids 13 to 47 (SEQ ID NO 6) of the aminoterminal sequence, more preferably comprising amino acids 22 to 47 (SEQ ID NO 8) of the aminoterminal sequence, a polypeptide comprising the *Bacillus subtilis* LicT protein (for instance as represented in SEQ ID NO 10), a homologue thereof, or a fragment thereof comprising the RNA-binding domain, said fragment preferably comprising amino acids 1 to 56 (SEQ ID NO 12) of the aminoterminal sequence, and a polypeptide comprising the bacteriophage MS2 coat protein (for instance as represented in SEQ ID NO 14), a homologue thereof, or a fragment thereof comprising the RNA-binding domain.

Targeting Module

A second module of the RNA delivery molecule comprises a targeting module. The terms "targeting module", "targeting molecule", "targeting protein" and "targeting polypeptide" are used herein as synonym and refer to a protein, or an essential part, or a homologue thereof capable of targeting the RNA delivery molecule to a targeting site in a living pest organism. The term "essential parts thereof" refers to parts of a targeting protein which are capable of targeting the RNA delivery molecule to a targeting site in a living pest organism. The term "homologue" of a targeting protein as used herein refers to a protein which has an amino acid sequence that has at least 30% identity, preferably at least 40%, 50%, 60%, 70%, 80% or 90% identity, most preferably at least 95% identity to a functional portion of the amino acid sequence of a targeting protein. It should be understood that instead of % "identity", also the corresponding % "similarity" could be used to define homologues according to the invention.

The term "functional portion" in the context of the present invention means a portion or fragment of the targeting protein comprising the domain or sequence which binds to the target cell or tissue in the pest organism.

As used herein the term "targeting site" refers to a specific cell or tissue in a living pest organism, as defined herein, to which the RNA delivery molecule according to the present invention is targeted.

The targeting module preferably comprises a protein which is capable of being endocytosed and/or transcytosed in a cell of the pest organism, or a protein able to bind an endocytosis and/or transcytosis receptor molecule present on a cell or a tissue of the pest organism, or any combinations thereof. In a preferred embodiment, the invention relates to an RNA delivery molecule as described above, wherein said at least one targeting polypeptide binds to a gut cell endocytosis or transcytosis receptor molecule. In another preferred embodiment, the invention relates to an RNA delivery molecule as described above, wherein said at least one targeting polypeptide binds to a tissue cell endocytosis or transcytosis receptor molecule.

"Endocytosis" is defined herein as the cellular uptake of macromolecules and particulate substances by localized regions of the plasma membrane that surround the substance and pinch off to form an intracellular vesicle. "Receptor-mediated endocytosis" is an essential process in all eukaryotes, including invertebrates such as insects or nematodes, and is required for general cellular functions, including uptake of nutrients (e.g., low-density lipoprotein [LDL] or transferrin) and recycling of membranes and membrane proteins.

"Transcytosis" is defined herein as the process by which a molecule may enter through one side of a cell and then migrate across the cell to exit on the other side. Transcytosis refers to the transport of substances across an epithelium by uptake into and release from coated vesicles. Also "receptor-mediated transcytosis" is an essential process in eukaryotes.

In certain embodiments of the present invention, the RNA delivery molecule comprises one targeting molecule, for instance a targeting molecule which allows endocytosis into the gut cell of a pest organism. In another example, the targeting molecule allows transcytosis from the lumen of the gut to the coelumic fluid or haemolymph of the pest organism. In other embodiments of the present invention the RNA delivery molecule comprises one targeting molecule which allows endocytosis into a tissue cell of the pest organism, such as for instance, but not limited to, a muscle cell, a gonade cell, a nerve cell. In another example, the targeting molecule allows transcytosis from an endothelial cell lining an organ to the lumen of said organ of the pest organism. In still other embodiments of the present invention, the RNA delivery molecule comprises two targeting molecules, for instance one targeting molecule which allows transcytosis from the gut cell of a pest organism to the coelumic fluid or haemolymph of the pest organism, and another targeting molecule which allows endocytosis into a tissue cell of the pest organism.

In particular examples, where the pest species is a fungal species, the term "endocytosis" is to be understood in the context of the fungi's feeding process. Upon feeding, fungi secrete enzymes or proteins in the process used by said fungal species for uptake of nutrients. As part of the feeding process, said enzyme or protein (bound or not to nutrients) is taken up again by said fungal species through endocytosis processes. Therefore, according to the present invention, the complex between the RNA delivery molecule and the dsRNA molecule that may cause RNA interference in the fungus, may simultaneously be taken up by the fungus through binding of a domain in the RNA delivery molecule to a secreted enzyme or protein (or to a part thereof, which is re-uptaken). The present invention is thus equally applicable to target the RNA delivery molecule or the complex to endocytosed proteins (or to their receptors on the fungal cell wall) in fungi.

In another embodiment the targeting molecule comprises at least one sequence which is recognized by a gut cell or a receptor on the gut cell of a pest organism, and which recognition triggers the endocytosis or transcytosis of the complex between the RNA delivery molecule and the chimeric RNAi molecule.

Preferred examples of endocytosis receptor binding molecules suitable for use in the present invention comprise but are not limited to transferrin proteins from any pest species, such as nematode or insect species such as for instance *Caenorhab-*

*ditis elegans, Drosophila melanogaster, Meloidygyne incognita* Corn Root Worm, Tabacco Budworm etc. . . . ;
serum transport proteins from any pest species, such as nematode or insect species
homologues of the above mentioned proteins in fungal species
vitellogenin, low density lipoprotein, transcobalamin, yolk proteins, and/or homologues thereof
Antibodies raised against receptors involved in receptor-mediated endocytosis in the pest organism
Antibodies such as IgG, IgA, IgE, (Trf)-specific camel antibodies
Antibodies raised against pest gut proteins, preferably camel antibodies
lectins such as snowdrop lectin, concanavalinA, Ricin
coat proteins from viruses such as Luteoviridae,
coat proteins from viruses such as Rous sarcoma virus, Semliki forest virus, Vesicular stomatitis virus, Adenovirus,
hormones and growth factors such as Insulin, Epidermal Growth Factor, Growth Hormone, thyroid stimulating hormone, Nerve Growth Factor, Calcitonin, Glucagon, Prolactin, Luteinizing Hormone, Thyroid hormone, Platelet Derived Growth Factor, Interferon, Catecholamines.

In a preferred embodiment, the endocytosis receptor binding molecule suitable for use in the present invention comprises transferrin proteins from any pest species, such as nematode or insect species, lectins such as snowdrop lectin, and coat proteins from viruses such as Luteoviridae.

Preferred examples of transcytosis receptor binding molecules suitable for use in the present invention comprise but are not limited to:
transferrin proteins from any pest species, such as nematode or insect species such as for instance
lectins such as snowdrop lectin, concanavalinA, Ricin
coat proteins from viruses such as Luteoviridae, In another preferred embodiment, the transcytosis receptor binding molecule suitable for use in the present invention comprise lectins such as snowdrop lectin, and coat proteins from viruses such as Luteoviridae.

In the examples section, a non-limiting number of RNA delivery molecules are described, comprising targeting polypeptides according to the invention.

According to yet another aspect of the invention, the RNA delivery molecule does not comprise a targeting polypeptide. The RNA delivery molecules according to this aspect of the invention may further comprise all elements of RNA delivery molecules as described herein. The major advantage of these RNA delivery molecules is that it may protect RNAi molecules by binding them in the complex, i.e. protection from plant Dicer and/or other plant degradation systems. Another advantage is that the RNA delivery molecule may direct and/or store the chimeric RNAi molecule of the invention in plant organelles, for instance in case the chimeric RNAi molecules do not encode such signals.

Linker Module

The RNA delivery module according to the invention preferably comprises a third module which consists of at least one peptide linker for linking the first to the second module. Said linker polypeptide preferably comprises a polypeptide of at least 3, preferably at least 4 or 5, most preferably at least 7, and more preferably at least 12 amino acids. Preferably said linker is a polypeptide comprising between 3 and 15 amino acids. Preferably said linker is a polypeptide comprising non-charged amino acids such as glycine, serine, cysteine, aspar- agine, tyrosine, glutamine, alanine, valine, proline, threonine, and preferably glycine or serine. A preferred example of a linker polypeptide comprises the polypeptide having the amino acid sequence GGGGSGGGGSGGGGS (SEQ ID NO 53). In preferred examples, the linker polypeptide comprises one of the following:
a factor Xa cleavage site, i.e. IEDR (SEQ ID NO 88),
a thrombin cleavage site, i.e. LVPGRS (SEQ ID NC) 89)
PGISGGGGG (SEQ ID NO 90)
GGS, or
AAA.

In a preferred embodiment, the present invention thus relates to an RNA delivery molecule as described above further comprising at least one linker module, preferably a linker module as described above.

Purification Module

The RNA delivery module according to the invention may further comprise a fourth module which consists of a purification tag. Said purification tags, defined by specific amino acid sequences, enables the easy purification of the tagged delivery molecule. Preferred examples of purification modules comprise but are not limited to His-tag, GST-tag, c-myc-tag, FLAG-tag, E-tag.

The invention thus further relates to an RNA delivery molecule as described above, further comprising a purification tag, preferably a purification tag as described above.

B. Chimeric RNAi Molecule

Chimeric RNAi Molecule

The term "chimeric RNAi molecule" or "RNAi molecule" as used herein means a sequence that contains
a nucleotide sequence corresponding to the target nucleotide sequence of the target gene of the pest organism and capable of inducing RNA interference, and
an RNA sequence recognized by RNA-binding protein or RNA-binding domain.

In the context of the present invention, the sequence corresponding to the target nucleotide sequence is contained in a double-stranded RNA (dsRNA) wherein said double-stranded RNA comprises annealed complementary strands, one of which has a nucleotide sequence which is complementary to at least part of a target nucleotide sequence of a target gene. The expressions "chimeric RNAi molecule", "RNAi mediating molecule", and "chimeric RNAi mediating molecule" all relate to a sequence containing a sequence corresponding to a target nucleotide sequence and the RNA sequence recognized by the RNA-binding protein or RNA-binding domain.

Preferred examples of chimeric RNAi molecules are molecules that consist of a target RNA sequence and an RNA sequence that is recognized by an RNA binding module as described in the present invention. The RNA sequences that are recognized by an RNA binding protein or RNA binding domain include but are not limited to RNA sequences recognized by the coliphage HK022 Nun protein, *Bacillus subtilis* LicT protein, or bacteriophage MS2 coat protein or essential parts, or homologues of said RNA binding proteins. The RNA sequences that are recognized by an RNA binding module as described in the present invention are specific, meaning that RNA sequences identical or comprising the consensus sequences as depicted in FIGS. 15 to 40 or as represented in FIGS. 41 and 42 are not or rarely found in a host (plant), target species or non-target species genome.

In a preferred embodiment, the present invention relates to a chimeric RNAi molecule comprising
at least one nucleotide sequence recognized by an RNA-binding protein or RNA-binding domain, for instance as represented in any of SEQ ID NOs 15 to 40, or an RNA secondary structure as represented in FIG. 41 or 42, and at least one nucleotide sequence corresponding to a target nucleotide sequence of a target gene of a pest species.

Table 3 provides an overview of different RNA sequences contained in chimeric RNAi molecules according to the present invention which are specifically recognized by a Nun, LicT or MS2 RNA-binding protein or RNA-binding domain as indicated

TABLE 3

| Amino acid sequence | Nucleic acid sequence |
| --- | --- |
| SEQ ID NOs 2, 4, 6 or 8 (coliphage HK022 Nun protein (*)) | SEQ ID NO 15 and 16 |
| SEQ ID NO 10 or 12 (*Bacillus subtilis* LicT protein (*)) | SEQ ID NOs 17 to 34 |
| SEQ ID NO 14 (bacteriophage MS2 coat protein (*)) | SEQ ID NOs 35 to 40 |

(*) or essential parts, or homologues thereof

According to a preferred embodiment, said chimeric RNAi molecule is a molecule as described in Example 2. According to further embodiments, the chimeric RNAi molecule has a sequence as represented in any of FIGS. 43 to 54 (any of SEQ ID NOs 41 to 52) or in any of FIGS. 56 to 58 (any of SEQ ID NOs 54 to 56), or in any of FIGS. 60 to 74 (any of SEQ ID NOs 57 to 71), or in any of FIGS. 76 to 90 (any of SEQ ID NOs 72 to 86).

In yet another embodiment, the present invention relates to a chimeric RNAi molecule according to the present invention as represented by any of SEQ ID NOs 41, 42, 43, 44, 45, 46, 47, 48, 49, 50, 51, 52, 54, 55 or 56. In another embodiment, the present invention relates to a chimeric RNAi molecule according to the present invention as represented by any of SEQ ID NOs 57, 58, 59, 60, 61, 62, 63, 64, 65, 66, 67, 68, 69, 70, 71. In yet another embodiment, the present invention relates to a chimeric RNAi molecule according to the present invention as represented by any of SEQ ID NOs 72, 73, 74, 75, 76, 77, 78, 79, 80, 81, 82, 83, 84, 85, 86.

Table 4 provides an overview of different examples of chimeric RNAi molecules according to the present invention which contain an RNA sequence that is specifically recognized by a Nun, LicT or MS2 RNA-binding protein or RNA-binding domain or essential parts, or homologues thereof as indicated.

TABLE 4

| | |
| --- | --- |
| SEQ ID NOs 2, 4, 6 or 8 (coliphage HK022 Nun protein (*)) | SEQ ID NOs 45, 46, 47, 48, 55, 61, 62, 63, 64, 70, 76, 77, 78, 79, 85 |
| SEQ ID NO 10 or 12 (*Bacillus subtilis* LicT protein (*)) | SEQ ID NOs 41, 42, 43, 44, 54, 57, 58, 59, 60, 69, 72, 73, 74, 75, 84 |
| SEQ ID NO 14 (bacteriophage MS2 coat protein (*)) | SEQ ID NOs 49, 50, 51, 52, 56, 65, 66, 67, 68, 71, 80, 81, 82, 83, 86 |

(*) or essential parts, or homologues thereof

In another embodiment, the present invention relates to the use of a chimeric RNAi molecule as defined herein, and in particular as represented by any of SEQ ID NOs 41, 42, 43, 44, 45, 46, 47, 48, 49, 50, 51, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 or 86 for down-regulation of target genes in a pest species, for delivering dsRNA and/or for producing transgenic plants resistant to pest organisms.

Target Genes

A "target gene" as used herein means a gene that needs to be silenced in the target (pest) species. The target gene may be selected from the genome of any species as described herein. According to a preferred embodiment, the target sequence is chosen from the genome of an organism which organism is different from the organism in which the dsRNA capable of causing interference is expressed. This means that the dsRNA is expressed in one (host) cell or organism and is subsequently transferred (or taken up by) to another cell or organism comprising the target gene. According to one specific embodiment of the present invention, the dsRNA is expressed in the plant or a plant cell and the target gene is chosen from the genome of a bacterium, a virus or an invertebrate, more particularly from a plant pest species such as a nematode, fungus or an insect. In the present context, the expression "dsRNA" relates to double stranded RNA capable of causing RNA interference. In another embodiment, the dsRNA is expressed in a bacterial or fungal cell and the bacterial or fungal cell is taken up or eaten by the pest species. According to still another embodiment, the dsRNA is isolated from, or purified from, the bacterial or fungal cell expressing the dsRNA, and the dsRNA is provided as a pesticide or in a pesticidal formulation to the pest species.

Particular suitable target genes are genes that are involved in an essential biological pathway of the target pest species, meaning that the target gene is an essential gene to the target pest species and that gene silencing of the target gene has an adverse effect on the viability the growth, development feeding, movement, and/or reproduction of the target pest species. Suitable target genes are genes associated with infection, propagation or pathogenesis of the pest species in the host. In another preferred embodiment the sequence of the target RNA in the pest organism comprises sequences of genes which are essential for development, neural function, reproduction or digestion of the pest organism.

In accordance with the present invention, any suitable double-stranded RNA fragment capable of directing RNAi or RNA-mediated gene silencing of a target gene can be used.

As used herein, a "double-stranded ribonucleic acid molecule (dsRNA)" refers to any RNA molecule, fragment or segment containing two strands forming an RNA duplex, notwithstanding the presence of single stranded overhangs of unpaired nucleotides.

The double-stranded RNA comprises annealed complementary strands, one of which has a nucleotide sequence which corresponds to a target nucleotide sequence of the target gene to be down-regulated. The other strand of the double-stranded RNA is complementary to this target nucleotide sequence.

According to the invention, the "dsRNA" or "double stranded RNA", whenever said expression relates to RNA that is capable of causing interference, may be formed from two or more separate polynucleotide strands which together form a double stranded, folded or assembled structure which includes at least one double-stranded portion effective in gene silencing by RNAi. For example, said dsRNA may be formed form two separate (sense and antisense) RNA strands that are annealed together. In this embodiment, the sense and antisense strands of the dsRNA originate form distinct RNA molecules, wherein at least one of the RNA molecules is a chimeric RNAi molecule as described above, expressed in the same or in another cell, and which RNA molecule may or may not comprise other domains or sequences which protect it from degradation or which direct it to specific locations. The RNA molecules may, when folded or assembled, include both double-stranded and single-stranded regions. The dsRNA may also comprise other sequences that are not complementary to a target gene or sequence but that have other functions.

Alternatively, the dsRNA may be formed from a single RNA polynucleotide molecule which includes regions of self-complementarity, such that when folded it is capable of forming a structure including one or more double-stranded portions (also referred as "dsRNA fragment(s)") effective in gene silencing by RNAi. For example, the dsRNA may have a foldback stem-loop or hairpin structure wherein the two annealed strands of the dsRNA are covalently linked. In this embodiment, the sense and antisense strands of the dsRNA are formed from different regions of a single chimeric RNAi molecule that is partially self-complementary. The features of "hairpin" or "stem-loop" RNAs for use in RNAi are generally known in the art (references: WO 99/53050). The organization of sense and antisense portions making up the double stranded RNA is variable. RNAs having this structure are convenient if the dsRNA is to be synthesized by expression in vivo, for example in a host cell or organism as discussed below, or by in vitro transcription. Non-limiting examples of the organization of sequences within a chimeric RNAi molecule are represented in FIG. 55, 59 or 75.

Further, as used herein, a double-stranded ribonucleic acid molecule may further include single stranded RNA molecules forming functional stem-loop structures, such as small temporal RNAs, short hairpin RNAs and microRNAs, thereby forming the structural equivalent of an RNA duplex with single strand overhangs. The RNA molecule of the present invention may be isolated, purified, native or recombinant, and may be modified by the addition, deletion, substitution and/or alteration of one or more nucleotides, including non-naturally occurring nucleotides, including those added at 5' and/or 3' ends to increase nuclease resistance.

If the methods of the invention are to be used for controlling growth or infestation of a pest organism in a host, it is preferred that that the dsRNA is not harmful for organisms other than the target organism(s), and consequently the double-stranded RNA does not share any significant homology with any host gene, or at least with any essential gene of the host. In this context, it is preferred that the double-stranded RNA shows less than 30%, more preferably less that 20%, more preferably less than 10%, and even more preferably less than 5% nucleic acid sequence identity with any gene of the host cell. % sequence identity should be calculated across the full length of the double-stranded RNA sequence capable of causing RNA interference. If genomic sequence data is available for the host organism then it is simple to cross-check sequence identity with the double-stranded RNA using standard bioinformatics tools.

Alternatively, in this context, it is preferred that 21 contiguous base pairs of the dsRNA do not occur in the genome of the host organism.

Preferably, the double-stranded RNA sequence capable of causing RNA interference does not have 20 contiguous nucleotides in common with a sequence of an organism other than the target organism. For example, when the target organism is a plant pathogen, such as a plant parasitic nematode or an insect, the double-stranded RNA does not have 20 contiguous nucleotides in common with a nucleotide sequence from a plant or a mammal (a human in particular).

The "target region" of the target pest gene may be any suitable region of the gene. The target region should comprise at least 17 or 18 consecutive nucleotides of the target gene, more preferably at least 19, 20 or 21 nucleotide and still more preferably at least 22, 23, 24 or 25 nucleotides of the target gene.

The term "complementarity" as used herein relates to DNA-DNA and RNA-RNA complementarity as well as to DNA-RNA complementarity. In analogy herewith, the term "RNA equivalent" means that in a DNA sequence(s), the base "T" may be replaced by the corresponding base "U" normally present in ribonucleic acids.

The term "nucleotide sequence which is complementary to" means a sequence that is complementary to at least part of a nucleotide sequence of a target gene. The term "complementary" when used in the context of the present invention for a dsRNA, means having substantial sequence identity to one of the strands of the target gene. In the present invention, the complementary sequence will generally comprise a nucleotide sequence having more than about 75% sequence identity to the corresponding sequence of the target gene, however, a higher homology might produce a more efficient inhibition of expression of the target gene. Preferably, the sequence identity is about 80%, 85%, 90%, 95%, and even more preferably more than about 99%. In the context of the present invention, the expression "more than about" has the same meaning as "at least".

It is most preferred that (at least part of) the double-stranded RNA will share 100% sequence identity with the target region of the target pest gene. However, it will be appreciated that 100% sequence identity is not essential for functional RNA inhibition. RNA sequences with insertions, deletions, and single point mutations relative to the target sequence have also been found to be effective for RNA inhibition. The term "corresponding to", when used to refer to sequence correspondence between the double-stranded RNA and the target region of the target gene, is therefore to be interpreted accordingly as not absolutely requiring 100% sequence identity.

Although the dsRNA must contain a sequence which corresponds to the target region of the target gene (i.e. wherein one strand of the dsRNA is complementary to at least part of a target (e.g. pest) nucleotide sequence) it is not absolutely essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

In another embodiment, the dsRNA may comprises multiple dsRNA fragments, each fragment comprising annealed complementary strands, one of which is complementary to a least part of a target nucleotide sequence to be silenced. Multiple dsRNA fragments as used in the present invention are also generally referred as to "concatemers". Thus, the present invention provides a chimeric RNAi molecule comprising:
  at least one nucleotide sequence recognized by an RNA-binding protein or RNA-binding domain, and
  multiple dsRNA fragments (concatemers), each comprising annealed complementary strands, one of which comprises a nucleotide sequence which is complementary to at least part of the nucleotide sequence of a pest target gene.

The term "multiple" in the context of the present invention means at least two, at least three, at least four, at least five, at least six, etc. and up to at least 10, 15, 20 or at least 30.

Non-limiting examples of suitable concatemers for use in the present invention include concatemer cloverleaf, concatemer dumbbell, concatemer hairpin, concatemer stem dsRNA.

In one embodiment, said dsRNA comprises multiple dsRNA fragments that are complementary to different (e.g. distinct) sequences in one target gene. In another embodiment, said dsRNA comprises multiple dsRNA fragments that are complementary to different (e.g. distinct) target genes. In yet another embodiment, said dsRNA comprises at least one repeat of one dsRNA fragment. As used herein "one repeat" means two copies of the same dsRNA fragment. In yet another embodiment, said dsRNA comprises at least two or three copies, preferably at least four, five or six copies, more preferably at least seven, eight, nine ten or more copies of one (e.g. the same) dsRNA fragment. In other words, said multiple dsRNA fragments are repeats of a single dsRNA fragment. In one preferred embodiment, the dsRNA fragments are not separated by non-hybridizing RNA fragments. In another embodiment, the dsRNA fragments are separated by a linker or spacer sequence. Preferably, the linker or spacer sequence is double stranded and the strands are complementary, thus also forming a double stranded region. The linker sequence may comprise a short random nucleotide sequence that is not complementary to target sequences. In another embodiment, the dsRNA fragments are not separated by a linker, a spacer or a lock sequence as described further.

The present invention encompasses chimeric RNAi molecules comprising at least one nucleotide sequence recognized by an RNA-binding protein or RNA-binding domain, and one dsRNA fragment comprising annealed complementary strands, one of which has a nucleotide sequence which is complementary to a least part of a target nucleotide sequence of a pest target gene, and which comprises one or more additional dsRNA fragments, each comprised of annealed complementary strands, wherein at least one complementary strands of each dsRNA fragment, comprises each independently a nucleotide sequence which is complementary to
    at least part of said nucleotide sequence of said pest target gene, or
    at least part of another nucleotide sequence of said pest target gene, or
    at least part of the nucleotide sequence of another pest target gene, or a combination thereof.

It should be clear that the expression "multiple dsRNA" in the chimeric RNAi molecule also encompasses chimeric RNAi molecules comprising copies of one or more dsRNA fragments and further comprising other dsRNA fragments, that are different from the repeated or copied dsRNA fragments. Therefore, the invention also relates to chimeric RNAi molecule comprising in addition to at least one nucleotide sequence recognized by an RNA-binding protein or RNA-binding domain, one or more repeats of dsRNA fragments and further comprising at least one dsRNA fragment which is distinct from the repeated fragment(s).

In the concatemer comprising chimeric RNAi molecule, the length of each of the dsRNA fragments may be at least 17 bp, 18 bp, 19 bp, 20 bp, 21 bp, 22 bp, 23 bp, 24 bp, 25 bp or more, for example about 30 bp, about 40 bp, about 50 bp, about 60 bp, about 70 bp, about 80 bp, about 90 bp, about 100 bp, about 110 bp or about 120 bp. Preferred dsRNA fragments in a concatemer comprising chimeric RNAi molecule have a length between 17 and 300 bp, preferably between 21 and 250 bp, preferably between 40 and 150 bp, more preferably between 50 and 120 bp or any number in between.

The terms "another target gene" or "a further target gene" are use interchangeably and mean for instance a second, a third or a fourth, etc. target gene.

According to one preferred embodiment, the dsRNA fragments target at least one target gene that is essential for viability, growth, development or reproduction of the pest and target at least one gene involved in pathogenicity or infectivity. Alternatively, the dsRNA fragments target multiple genes of the same category, for example, the dsRNA fragments target at least two essential genes or at least two genes involved in pathogenicity or at least two genes involved in any of the cellular functions. According to a further embodiment, the dsRNA fragments target at least two target genes, which target genes are involved in a different cellular function. For example, the dsRNA fragments target two or more genes involved in protein synthesis (e.g. ribosome subunits), protein degradation (e.g. proteasome subunits), formation of microtubule cytoskeleton (e.g. beta-tubulin gene), and the like.

The dsRNA fragments in the chimeric RNAi molecule may be combined as follows:
  a) when multiple dsRNA fragments targeting a single target gene are combined, they may be combined in the original order (i.e. the order in which the regions appear in the target gene) in the chimeric RNAi molecule,
  b) alternatively, the original order of the fragments may be ignored so that they are scrambled and combined randomly or deliberately in any order into the chimeric RNAi molecule,
  c) alternatively, one single fragment may be repeated several times, for example from 1 to 10 times, e.g. 1, 2, 3, 4, 5, 6, 7, 8, 9 or 10 times, in the chimeric RNAi molecule, or
  d) the dsRNA fragments (targeting a single or different target genes) may be combined in the sense or antisense orientation.

The present invention thus encompasses a chimeric RNAi molecule comprising at least one nucleotide sequence recognized by an RNA-binding protein or RNA-binding domain and multiple dsRNA fragments targeting different target genes which originates from a single target (or pest) species, or wherein sa id different target genes originates from district target (or pest) species, for instance pest species belonging to the same (in one embodiment) or to different (in other embodiments) genera, families, orders or even phyla.

The chimeric RNAi molecules comprising such multiple dsRNA fragments and targeting multiple target genes, are characterized by stacking multiple RNAi capacity, resulting in synergetic effects, and capable of triggering multiple RNAi effects in the target cell or target organism.

The dsRNA may further contain DNA bases, non natural bases or non-natural backbone linkages or modifications of the sugar-phosphate backbone, for example to enhance stability during storage or enhance resistance to degradation by nucleases.

The double-stranded RNA fragment capable of causing interference will itself preferably be greater than 17 bp in length, preferably 19 bp in length, more preferably greater than 20 bp, more preferably greater than 21 bp, or greater than 22 bp, or greater than 23 bp, or greater than 24 bp, or greater than 25 bp in length.

The design and production of suitable chimeric RNAi molecules comprising double stranded RNA for the present invention is documented in the examples section. Optionally, within the chimeric RNAi molecules of the present invention, there may be included one or more moieties capable of protecting the double stranded RNA portion (causing RNA interference) against RNA processing. Such moieties and instructs are described in a patent application of applicant having application number 0423659.2 and which was filed on Oct. 25, 2004 at the UK Patent Office (and of which the publication number will be provided once available) and other patent applications of applicant having application number U.S. 60/621,800 and which was filed on Oct. 25, 2004 and having application number U.S. 60/683,551 which was filed on May 5, 2005, at the US Patent and Trademark Office (and of which the publication number will be provided once available). Both patent applications are incorporated herein in their entirety. Chimeric RNAi constructs according to the present invention may thus comprise different dsRNA core types, optionally comprising linker types, optionally comprising different lock types designed to protect the dsRNA core against RNA processing in the host cell expressing the dsRNA construct. In one embodiment of the invention a sequence capable of protecting the dsRNA against RNA processing is also referred to as a "lock". (For the terminology used in this particular section, relating to protection of dsRNA, reference is made to the above-mentioned UK and US patent applications by applicant).

Whenever a stabilized or protected chimeric RNAi molecule is described, the term "core" refers to the dsRNA portion, which core may comprise at least one dsRNA fragment or which may comprise multiple dsRNA fragments.

The term "dsRNA core" as used herein refers to the core of the dsRNA molecule. Different dsRNA core types are for example a single stem comprising one dsRNA, a single stem comprising multiple dsRNA fragments (concatemer) which dsRNA fragments are each independently complementary to one target gene or to different target sequences of one target gene or are complementary to different target genes.

The term 'lock' as used herein refers to a sequence capable of protecting the dsRNA or a portion thereof against RNA processing. Different lock types include a GC rich clamp, a short loop of about 4 or of about 5 base pairs, a mismatch lock, or a protein binding RNA structure such as an IRES, a 5' region of a virus, an Iron responsive element or other RNA motifs that are recognized by proteins.

Other mechanisms to protect the dsRNA against RNA processing may be combined within the chimeric RNAi molecules of the present invention, for example embedding the dsRNA in viroids or in natural unprocessed RNA structures (such as mi RNA, tRNA, ribosomal RNA, components of the spliceosome or other non-coding RNA's transcribed from RNA polymerase I, II or III promoters). Embedding the dsRNA in a viroid-like dsRNA structure is described and illustrated for instance in Navarro and Flores (2000 EMBO Journal 19 (11) p 2662. The dsRNA may be incorporated within the viroid as such, or in the viroid mutated to avoid internal cleavage (for example by ribozymes) or to avoid translation. Mutations can be based on information from Dais et al. (1991, NAR 19 (8), p 1893). These type of constructs may be transported to the chloroplasts, where it can receive extra protection against dsRNA processing.

Another mechanism to protect dsRNA from processing is to signal the dsRNA towards an intracellular compartment of the host cell. For example, the dsRNA can be compartmentalized in an intermediate host cell, before it is transferred to the target host cell. In particular, the chimeric RNAi molecule may be compartmentalized in a plant cell, for example, it may be located in the chloroplast, mitochondrion or plastid, before it is transferred to the plant pest species, for example the plant pest nematode or insect. Compartmentalization may occur in a variety of ways, such as for example via the use of viroid structures, or via the use of signal sequences, for example chloroplast, mitochondrial or plastid signal sequences. These organelles are from prokaryotic origin and may offer a protective environment away from the plant RNA processing machinery.

The term "linker" as used herein for the chimeric RNAi molecule refers to a molecule enabling linking of a lock to a dsRNA core. Different linker types are conditionally self-cleaving RNA moieties such as linkers that are cleaved at low pH or at high pH or that are cleaved in hydrophobic conditions, or are one of an intron, or a non-complementary RNA sequence. Optionally, the chimeric RNAi molecule may comprise an interstem base pairing moiety or can be in the form of a triple RNA. In a preferred embodiment, the multiple dsRNA fragments of the chimeric RNAi molecule are connected without linker. In another embodiment, a linker is present between the at least one nucleotide sequence recognized by an RNA-binding protein or RNA binding domain and the dsRNA in the chimeric RNAi molecule. In still another embodiment, the multiple dsRNA fragments of the chimeric RNAi molecule are connected by one or more linkers.

In a particular embodiment, the linkers may be used to disconnect smaller dsRNA regions in the pest organism. Advantageously, in this situation the linker sequence may promote division of a long dsRNA into smaller dsRNA under particular circumstances, resulting in the release of separate dsRNA fragments under these circumstances and leading to more efficient gene silencing by these smaller dsRNA fragments. Non-limiting examples of suitable conditionally self-cleaving linkers are RNA sequences that are self-cleaving at suitable pH conditions. Suitable examples of such RNA sequences are described by Borda et al. (Nucleic Acids Res. 2003 May 15, 31 (10):2595-600), which document is incorporated herein by reference. This sequence originates form the catalytic core of the hammerhead ribyozome HH16. Alternatively, the linkers are self cleaving in the endosomes. This may be advantageous when the chimeric RNAi molecule of the invention is taken up by the pest via endocytosis or transcytosis, and are therefore compartmentalized in the endosomes of the pest. The endosomes may have a low pH environment, leading to the cleavage of the linker. Linkers that are self-cleaving in hydrophobic conditions are particularly useful in chimeric RNAi molecules of the present invention when used to be transferred from one cell to another via the transit in a cell wall, for example when crossing the cell wall of a pest. Particular plant pest organisms of interest for application of this technique are plant parasitic fungi or plant parasitic viruses or bacteria.

An intro may be used as a linker. An "intron" as used herein may be any non-coding RNA sequence of a messenger RNA. Particular suitable intron sequences for the chimeric RNAi molecules of the present invention are (1) U-rich (35-45%); (2) have an average length of 100 bp (varying between about 50 and about 500 bp) which base pairs may be randomly chosen or may be based on known intron sequences; (3) strat at the 5' end with -AT:GT- or -CG:GT- and/or (4) have at their 3' end -AG/GC- or AG:AA.

According to the invention, a linker sequence may be present between the dsRNA fragments or not. Preferably, no linker sequence is present between the dsRNA fragments. For instance when the dsRNA comprising the dsRNA fragments is chemically synthesized, the dsRNA fragments may be directly adjacent to each other, without the presence of non-target sequences. When present, the linker may for instance comprise a short random nucleotide sequence that is not complementary to target sequences but that is the result of the cloning.

A by itself non-complementary RNA sequence, ranging from about 1 base pair to about 10000 base pairs, for instance of at least 10, 20, 30, 50, 60, 70, 80, 90, 100, 200, 500, 1000, 1500, 2000, 3000, 10000 base pairs, or any number in-between, may also be used as a linker.

Choice of Target Gene(s) to be Targeted by a Chimeric RNAi Molecule or a Complex Thereof Comprising an RNA Delivery Molecule According to the Invention The choice of target gene(s) to be targeted by a chimeric RNA molecule depends on the choice of target gene which is to be silenced in the target organism or organisms in order to achieve the desired effect of pest control. For the chimeric RNA molecule designed herein below the target gene(s) was (were) chosen from one or more of the following categories of genes:

1. "essential" genes encompass genes that are vital for one or more target organisms and result in a lethal or severe (e.g. movement, feeding, paralysis, drinking, fertility) phenotype when silenced.
2. "pathogenicity genes" are genes that are involved in the pathogenicity or infectivity of the pest.
3. "pest specific" genes encompass genes that have no substantial homologous counterpart in non-pest organisms as can be determined by bioinformatics homology searches, for example by BLAST searches. The choice of a pest specific target gene results in a species-specific RNAi effect, with no effect or no substantial (adverse) effect in non-target organisms.
4. "conserved pathway" genes encompass genes that are involved in the same biological pathway or cellular process, or encompass genes that have the same functionality in different species resulting in a specific and potent RNAi effect and more efficient pest control.
5. According to the present invention, the chimeric RNA molecules target genes inducing improved delivery/uptake/endocytosis in the pest, such as for example chitin synthase genes, genes encoding peritrophic membrane proteins, excreted RNAses, proteins involved in the secretion of Rnase in the gut; tight junction genes, septate junction genes, genes encoding proteins involved in the acidification of the gut (especially for lepidoteren insect, such as ion channels) and any proteins involved in the maintenance and/or regeneration of gut epithelium.

Combination of Multiple Target Sequence or Multiple Target Species

The RNA delivery molecules, chimeric RNAi molecules, complexes thereof and methods of the present invention are particularly useful to target multiple sequences simultaneously. These multiple sequences may originate from one target gene. Alternatively, the multiple target sequences may originate from multiple target genes. These multiple target genes may originate from one and the same pest species. Alternatively, these multiple target genes may originate from different pest species from the same or different order. Therefore, one chimeric RNA molecule of the present invention, for example in the form of a concatemer cloverleaf, a concatemer stem, or a concatemer hairpin, may simultaneously target multiple sequences originating from the same and/or multiple target genes of the same and or different pest species, such as from nematodes, insects, bacteria and/or fungi.

According to one particular embodiment of the present invention, the RNA delivery molecules, chimeric RNAi molecules, or complexes thereof targets multiple target genes originating from multiple species. For example, a chimeric RNAi molecule may target multiple genes from multiple plant pest organisms, and by expressing the chimeric RNAi molecule in the plant, the plant acquires resistance against multiple plant pests simultaneously. Similarly, a plant or a surface or substance susceptible to pest infestation may be sprayed with a composition (or the like) comprising the RNA delivery molecules, chimeric RNAi molecules, or complexes thereof, thereby protecting the plant or the surface or substance against infestation from multiple pests. For example, the plant acquires resistance against nematodes and insects, or against nematodes, insects and/or fungi. Also the chimeric RNAi molecule allows the plant to acquire resistance against multiple nematodes of a different genus, family, order or class, and/or against insects of a different genus, family or order, and/or against fungi of a different genus, family or order.

In another particular embodiment of the present invention, the chimeric RNAi molecule targets multiple target genes originating from different species from the same order. For example, one chimeric RNAi molecule which targets genes of different bacterial, viral, fungal, insect or nematode species, may be used as an effective and broad spectrum bacteria, virus, fungus, insect killer or broad spectrum nematode killer. Combination of dsRNA fragments with at least one nucleotide sequence recognized by an RNA-binding protein or RNA-binding domain into one chimeric RNAi molecule according to the present invention, wherein said dsRNA fragments are targeting multiple target sequences from different pest species is favorable to enlarge the pest species spectrum of the RNAi effect of the dsRNA molecules.

In another particular embodiment of the present invention, the chimeric RNAi molecule targets multiple target genes originating from the same organism, for example from the same pest species. Such a construct offers the advantage that several weak target genes from the same organism can be silenced together to efficiently control the pest organism, while silencing one or more of the weak target genes separately is not effective to control the pest. Also, several strong target genes from the same organism can be silenced simultaneously, in order to further improve the efficacy of the pest control, or to avoid the occurrence of resistance of the pest organisms by mutation.

C. Target and Pest Organisms

The terms "target organism" or "target species" or "pest organism" or "pest species" are used herein as synonym and refer to any organism or species which needs to be killed or paralyzed. Suitable target species are chosen from the group comprising fungi, insects, mites, protozoa, metazoa (comprising nematodes), algae, plants, animals (including mammals). Most suitable for the methods of the present invention are target species which are pest organisms. Preferably, in the context of the present invention, the term "target species" or "pest species" refers to plant pest organisms such as nematodes, insects and fungi and preferably refers to any organism classified in the taxonomical group of the Insecta or of the Nematoda, or of the Fungi.

Nematodes

"Nematodes" as used herein comprises species of the order Nematoda. Many species of nematodes are parasitic and cause health problems to humans and animals (for example species of the orders Ascaradida, Oxyurida, Strongylida, *Stronglyloides* and Trichocephalida), as well as to plants and fungi (for example species of the orders Aphelenchida, Tylenchida ad others). Preferably, "nematodes" a % used herein refers to plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonema* spp.; sedentary parasites such as *Heterodera* spp., *Globodera* spp., and

*Meloidogyne* spp., and stem and leaf endoparasites such as *Ditylenchus* spp., *Aphelenchoides* spp., and *Hirshmaniella* spp. According to a preferred embodiment of the invention, the nematodes are plant parasitic nematodes, in particular root parasitic soil nematodes such as, for example, those of the genera *Heterodera* and *Globodera* (cyst-forming nematodes) and *Meloidogyne* (root knot nematodes). The RNA constructs of the present invention are particularly suitable to control harmful species of the genus *Meloidogyne*, such as for example, *Meloidogyne incognita*, and of the genus *Heterodera*, such as for example, *Heterodera glycines* (soybean cyst nematode) and also of the genus *Globodera*, such, as for example, *Globodera rostochiensis* (potato cyst nematode) and also representatives of migrating endoparasites, such as, for example, *Pratylenchus penetrans* or *Radopholus similes* and representatives of ectoparasites, such as, for example, *Trichodorus* spp. and *Xiphinema* spp. However, the use of the RNA constructs according to the invention is in no way restricted to these genera, but also extends in the same manner to other nematodes.

Fungi

"Fungi" as used herein comprises all species of the order Fungi. According to a preferred embodiment of the invention, the target gene originates from a plant parasitic fungus such as *Magnaporthe oryzae* (rice blast, formerly *Magnaporthe grisae*; an amorph *Pyricularia oryzae* Cav. and *Pyricularia grisae*); *Rhizoctonia* spp., particularly *Rhizoctonia solani* and *Rhizoctonia oryzae*; *Gibberella fujikuroi*; *Sclerotinium* spp.; *Helminthosporium sigmoideum*; *Pythium* spp.; *Alternaria* spp., particularly *Alternara solani*, *Fusarium* spp., particularly *Fusarum solani* and *Fusarium germinearum*, *Acremoniella* spp.; *Leptosphaeria salvinii*; *Puccinia* spp., particularly *Puccinia recondita* and *Puccinia striiformis*; *Septoria nodorum*; *Pyrenophora teres*; *Rhincosporium secalis*; *Erysiphe* spp., particularly *Erysiphe graminis*; *Cladosporium* spp.; *Pyrenophora* spp.; *Tilletia* spp.; *Phytophthora* spp., particularly *Phytophthora infestans*; *Plasmopara viticola*; *Uncinula necator*; *Botrytis cinerea*; *Guiguardia bidwellii*; *C. viticola*; *Venturia inaequalis*; *Erwinia armylovora*; *Podosphaera leucotricha*; *Venturia pirina*; *Phakospora* sp (soybean rust), *Ustilago maydis* (corn smut).

Insects

"Insects" as used herein comprises all insect species. In an embodiment said insect species comprise species of the order Lepidoptera. According to a preferred embodiment of the invention, the insects are insects that damage plants, comprising amongst others Leptidopteran insect pests, such as *Heliothis* spp., *Helicoverpa* spp., *Spodoptera* spp., *Ostrinia* spp., *Pectinophora* spp, *Agrotis* spp., *Scirphophaga* spp., *Cnaphalocrocis* spp., *Sesamia* spp, *Chilo* spp., *Anticarsia* spp., *Pseudoplusia* spp., *Epinotia* spp., and *Rachiplusia* spp., preferably *Heliothis virescens*, *Helicoverpa zea*, *Helicoverpa armigera*, *Helicoverpa punctera*, *Ostrinia nubilafis*, *Spodoptera frugiperda*, *Agrotis ipsilon*, *Pectinophora gossypiella*, *Scirphophaga incertulas*, *Cnaphalocrocis medinalis*, *Sesamia inferens*, *Chilo partellus*, *Anticarsia gemmatalis*, *Pseudoplusia includens*, *Epinotia aporema* and *Rachiplusia nu.* e.g. Examples of preferred Insecta include, but are not limited to, members of the orders Coleoptera (*Anobium*, *Ceutorhynchus*, *Rhynchophorus Cospopolites*, *Lissorhopterus* spp., *Lissorhopterus oryzophitus*, *Meligethes*, *Echinocnemus squamos*, *Hypothenemus*, *Hylesinus*, *Acalymma*, *Lema*, *Psylliodes*, *Leptinotarsa*, *Gonocephalum*, *Agriotes*, *Dermolepida*, *Heteronychus*, *Phaedon*, *Tribolium*, *Sitophilus* spp., *Sitophilus zeamais*, *Diabrotica* spp. (*Diabrotica virgifera virgifera*, *Daibrotica undecimpunctata howardi*, *Diabrotica barberi*), *Oulema oryzae*, *Chaetocnema pulicaria*, *Epilachna varivestis*, *Cerotoma trifurcata*, *Leptinotarsa decemlineata Anthonomus* spp., *Anthonomus grandis*, or *Anthrenus* spp.), Lepidoptera(e.g. *Ephestia*, *Mamestra*, *Earies*, *Pectinophora*, *Ostrinia*, *Trichoplusia*, *Pieris*, *Laphygma*, *Agrotis*, *Amathes*, *Wiseana*, *Tryporyza*, *Diatraea*, *Sporganothis*, *Cydia*, *Archips*, *Plutella*, *Chilo*, *Heliothis*, *Helicoverpa* (especially *Helicoverpa armigera*), *Spodoptera* or *Tineola* ssp.), Diptera (e.g. *Musca*, *Aedes*, *Anopheles*, *Culex*, *Glossina*, *Sirnulium*, *Stomoxys*, *Haematobia*, *Tabanus*, *Hydrotaea*, *Lucilia*, *Chrysomia*, *Callitroga*, *Dermatobia*, *Gasterophilus*, *Hypoderma*, *Hylemyia*, *Atherigona*, *Chlorops*, *Phytomyza*, *Ceratitis*, *Liriomyza*, and *Melophagus* spp.), Phthiraptera, Hemiptera (e.g. *Laocdelphax striatellus*, *Sogatella furcifera*, *Rhopalosiphum maidis*, *Macrosiphum euphorbiae*, *Aphis* spp. (*Aphis gossypii*, *Aphis glycines*), *Bemisia* spp., *Bemisia tabaci*, *Phorodon*, *Aeneoplamia*, *Empoasca* spp. (*Empoasca fabae*, *Empoasca solana*), *Parkinsiella*, *Pyrilla*, *Aonidiella*, *Coccus*, *Pseudococcus*, *Helopeltis*, *Lygus*, *Dysdercus*, *Oxycarenus*, *Nezara*, *Aleurodes*, *Triatoma*, *Rhodnius*, *Psylla*, *Myzus* spp., *Myzus persicae*, *Megoura*, *Phylloxera*, *Adelyes*, *Nilaparvata* spp., *Nilaparvata lugens*, *Nephrotettix* spp., *Nephoteftix virescens*, or *Cimex* spp.), Orthoptera (e.g. *Locusta*, *Gryllus*, *Schistocerca* or *Acheta* spp.), Dictyoptera (e.g. *Blattella*, *Periplaneta* or *Blatta* spp.), Hymenoptera(e.g. *Athalia*, *Cephus*, *Atta*, *Lasius*, *Solenopsis* or *Monomorium* spp.), Isoptera(e.g. *Odonotermes* and *Reticulitermes* spp.), Siphonaptera(e.g. *Ctenocephalides* or *Pulex* spp.), Thysanura (e.g. *Lepisma* spp.), Dermaptera(e.g. *Forficula* spp.) and Psocoptera (e.g. *Peripsocus* spp.) and Thysanoptera (e.g. *Thrips tabaci*).

Bacteria

"Bacteria" that damage plants and that can be controlled with the constructs and methods of the present invention are for example *Agrobacterium* ssp.; *Arachnia* ssp.; *Clavibacter* ssp.; *Corynebacterium* ssp.; *Erwinia* ssp.; *Fusobacterium* ssp.; *Hafnia* ssp.; *Pseudornonas* ssp.; *Spiroplasma* ssp.; *Streptomyces* ssp.; *Xanthomonas* ssp.; *Xylella* ssp. and *Xylophilus* ssp.

Viruses

"Viruses" that damage plants and that can be controlled with the constructs and methods of the present invention are for example African cassava mosaic virus; Alfalfa mosaic virus; American plum line pattern virus; Andean potato latent virus; Andean potato mottle virus; Apple chlorotic leaf spot virus; Apple mosaic virus; Apple stem grooving virus; Arabis mosaic virus; Arracacha virus B, oca strain; Asparagus virus 2; Australian grapevine viroid; Avocado sunblotch viroid; Barley mild mosaic virus; Barley stripe mosaic virus; Barley yellow dwarf virus; Barley yellow mosaic virus; Bean common mosaic virus; Bean golden mosaic virus; Bean leaf roll virus; Bean pod mottle; Bean yellow mosaic virus; Bearded iris mosaic virus; Beet curly top virus; Beet leaf curl virus; Beet mosaic virus; Beet necrotic yellow vein virus; Beet pseudo yellows virus; Beet western yellows virus; Beet yellow stunt virus; Belladona mottle virus; Black rasberry latent virus; Blight (et analogues/en analoge); Blueberry leaf mottle virus; Broad bean wilt virus; Bromoviruses; Cacao swollen shoot virus; Cacao yellow mosaic virus; Cactus virus X; Cadan-cadang viroid; Carnation cryptic virus; Carnation etched ring virus; Carnation latent virus; Carnation mottle virus; Carnation necrotic fleck virus; Carnation ringspot virus; Carnation vein mottle virus; Cassava common mosaic virus; Cauliflower mosaic virus; Cherry leafroll virus; Cherry rasp leaf virus; Cherry rasp leaf virus (American); Cherry rugose virus; Chrysanthemum B virus; Chrysanthemum stunt viroid; Citrus exocortis viroid; Citrus leaf rugose virus; Citrus mosoie virus; Citrus tristeza virus (European isolates); Citrus tristeza virus (non-European isolates); Citrus variegation virus; Citrus veinenation woody gall; Citrus viroids; Clover Yellow vein virus; Cocksfoot mild mosaic virus group; Cocksfoot streak virus; Cowpea mild mottle virus; Cucumber mosaic virus; Cucumber yellows virus; Cucumovirus satellites; Cymbidium mosaic virus; Dahlia mosaic virus; Dasheen mosaic virus; Dianthoviruses; Echtes Ackerbohnenmosaic virus; Elderberry carlavirus; Euphorbia mosaic virus; Florida tomato virus; Grapevine algerian latent virus; Grapevine bulgarian latent virus; Grapevine fanleaf virus; Grapevine flavescence dorée mycoplasm; Grapevine leafroll associated virus (I to V); Grapevine tunusian ringspot virus; Grapevine virus A; Grapevine yellow speckle viroids (I & II); Grapewine chrome mosaic virus; Heracleum latent virus; Hippeastrum mosaic virus; Honeysuckle latent virus; Hop (American) latent virus; Hop latent virus; Hop mosaic virus; Hop stunt viroids; Hop virus A; Hop virus C; Hydrangea ringspot virus; Iliaviruses; Iris mild mosaic virus; Leek yellow stripe virus; Leprosis; Lettuce infectious yellows virus; Lettuce mosaic virus; Lilac chlorotic leafspot virus; Lilac ring mottle virus; Lilly symptomless virus; Luteovirus satellites; Maize dwarf mosaic virus; Maize streak virus; Marafiviruses; Melon necrotic spot virus; Myrobolan latent ringspot virus; Narcissus latent virus; Narcissus mosaic virus; Narcissus tip necrosis virus; Narcissus yellow stripe virus; Oat golden stripe virus; Oat mosaic virus; Odontoglossum ringspot virus; Olive latent ringspot virus; Onion yellow dwarf virus; Papaya mosaic virus; Papaya ringspot virus; Parsnip yellow fleck virus; Pea early browning virus; Pea enation mosaic virus; Pea seed borne mosaic virus; Peach mosaic virus (American); Pear decline mycoplasm; Pelargonium leaf curl virus; Pepper mild tigré virus; Plant reoviruses; Plum line pattern virus (American); Plum pox virus; Poinsettia mosaic virus; Poplar mosaic virus; Potato aucuba mosaic virus; Potato black ringspot virus; Potato leafroll virus; Potato leafroll virus (non European isolates); Potato mop-top virus; Potato spindle tuber viroid; Potato virus A; Potato virus A (non European isolates); Potato virus M; Potato virus M (non european isolates); Potato virus S; Potato virus S (non European isolates); Potato virus T; Potato virus X; Potato virus X (non European isolates); Potato virus Y; Potato virus Y (non European isolates); Potato yellow dwarf virus; Potato yellow mosaic virus; Prune dwarf virus; Prunus necrotic ringspot virus; Raspberry bushy dwarf virus; Raspberry leaf curl virus (American); Raspberry ringspot virus; Raspberry vein chlorosis virus; Red clover mottle virus; Red clover vein mosaic virus; Ribgrass mosaic virus; Rice stripe virus group; Rubus yellow net virus; Saguro cacao virus; Satellites (andere dan geciteerde); Satsuma dwarf virus; Shallot latent virus; Sharka virus; Sobemoviruses; Sowbane mosaic virus; Sowthistle yellow vein virus; Spinach latent virus; Squash leaf curl virus; Stolbur mycoplasm; Strawberry crinkle virus; Strawberry latent C virus; Strawberry latent ringspot virus; Strawberry mild yellow edge virus; Strawberry vein banding virus; Sugar beet yellows virus; Tater leaf virus; Tobacco etch virus; Tobacco mosaic virus; Tobacco necrosis virus; Tobacco rattle virus; Tobacco ringspot virus; Tobacco streak virus; Tobacco stunt virus; Tomato apical stunt viroid; Tomato aspermy virus; Tomato black ring virus; Tomato bunchy top viroid; Tomato bushy stunt virus; Tomato mosaic virus; Tomato planta macho viroid; Tomato ringspot virus; Tomato spotted wilt virus; Tomato yellow leaf curl virus; Tulare apple mosaic virus; Tulip breaking virus; Turnip crinkle virus satellites; Turnip crinkle virus; Turnip mosaic virus; Turnip yellow mosaic virus; Tymoviruses; Velvet tobacco mottle virus; other Viroids; Watermelon mosaic virus 2; Wheat dwarf virus; Wheat soil-bome mosaic virus; Wheat spindle steak mosaic virus; Wheat yellow mosaic virus; White clover mosaic virus; Yam mosaic virus; Zucchini yellow fleck virus; and Zucchini yellow mosaic virus.

The pest organism can be any species. Preferably, the pest organism is any insect or nematode of economic importance, such as, for example, organisms that cause disease, a household pest, or an agricultural pest, or that are associated with plants diseases, e.g. in corn, potatoes, soybeans, sugarbeets, turf, trees, orchards and vineyards, garden vegetables, etc.

The pest organism can be at any stage of development, however, it is preferred that when the organism is an insect, it is in a larval or adult developmental stage when the dsRNA is delivered.

D. Nucleotide Sequences, Vectors and Host Cells

In another embodiment, the invention relates to nucleic acids encoding the RNA delivery molecule and encoding the chimeric RNAi molecules as described herein.

Vectors

According to a further aspect of the present invention, there are provided expression constructs, also referred herein as recombinant DNA constructs, to facilitate introduction into a host cell and for instance a plant cell and/or facilitate expression and/or facilitate maintenance of the nucleotide sequence encoding the RNA delivery molecules and/or the chimeric RNAi molecules according to the invention. The expression constructs may be inserted into a plasmid or a vector, which may be commercially available.

According to an embodiment of the present invention, the expression construct is an expression vector, suitable for transformation into host organisms such as yeast, bacteria, fungi or plants or plant cells and suitable for maintenance and expression of an RNA delivery molecule or a chimeric RNAi molecule according to the present invention in a transformed host cell. An "expression vector" is a construct that can be used to transform a selected host cell and provides for expression of a coding sequence in the selected host. Expression vectors can for instance be cloning vectors, binary vectors or integrating vectors. The invention thus also relate to a vector comprising any of the nucleic acids described above. Said vector may further comprise regulatory sequences for controlling expression of the nucleic add in said host cell.

According to one embodiment of the present invention, the expression construct is a plant expression vector, suitable for transformation into plants and suitable for maintenance and expression of an RNA delivery molecule or a chimeric RNAi molecule according to the present invention in a transformed plant cell. The invention thus also relates to a vector comprising any of the nucleic acids described above. Said vector may further comprise regulatory sequences for controlling expression of the nucleic acid in a plant cell.

The terms "regulatory sequences" and "control sequence" used herein are to be taken in a broad context and refer to regulatory nucleic acid sequences capable of driving and/or regulating expression of the sequences to which they are ligated and/or operably linked. The control sequences differ depending upon the intended host organism and upon the nature of the sequence to be expressed. For expression of a protein in prokaryotes, the control sequences generally include a promoter, a ribosomal binding site, and a terminator. In eukaryotes, control sequences generally include promoters, terminators and, in some instances, enhancers, and/or 5' and 3' untranslated sequences. The term 'control sequence' is intended to include, at a minimum, all components necessary for expression, and may also include additional advantageous components. According to one embodiment of the present invention, the control sequence is operable in a plant; preferably the control sequence is a sequence derived from a plant sequence. The term "control sequence" encompasses a promoter or a sequence capable of activating or enhancing expression of a nucleic acid molecule in a cell, tissue or organ.

Promoters useful for the expression of dsRNA are a promoter from an RNA PoII, an RNA PoIII, an RNA PoIIII, T7 RNA polymerase or SP6 RNA polymerase. These promoters are typically used for in vitro-production of dsRNA, which dsRNA is then included in an antipesticidal agent for example in an anti-pesticidal liquid, spray or powder.

Examples of promoters suitable for the constructs and methods according to the present invention are constitutive plant promoters, such as the CaMV35S promoter, doubled CaMV35S promoter, GOS2 promoter, Figwort mosaic viruse (FMV) 34S promoter, rubisco promoter, actin promoter or ubiquitin promoter.

In order to improve the transfer of the dsRNA from the plant cell to the plant pest, the plants preferably express the dsRNA in plant parts easily accessible to the plant pest. Preferred tissues to express the dsRNA in are the roots, leafs, stems, rhizomes, shoots, tubers, anthers, petioles, seeds, flowers, fruits. Therefore, tissue-preferred promoters may be used, such as a root specific promoter or a leaf specific promoter. Suitable examples of a root preferred promoter are PsMTA (Fordam-Skelton, A. P., et al., 1997 Plant Molecular Biology 34: 659-668), Class III Chitinase promoter, etc. . . . . Examples of leaf- and stem-specific or photosynthetic tissue-specific promoters that are also photoactivated are promoters of two chlorophyll binding proteins (cab1 and cab2) from sugar beet (Stahl D. J., et al., 2004 BMC Biotechnology 2004 4:31), ribulose-bisphosphate carboxylase (Rubisco), encoded by rbcS (Nomura M. et al., 2000 Plant Mol. Biol. 44: 99-106), A (gapA) and B (gapB) subunits of chloroplast glyceraldehyde-3-phosphate dehydrogenase (Conley T. R. et al. 1994 Mol. Cell. Biol. 19: 2525-33; Kwon H. B. et al. 1994 Plant Physiol. 105: 357-67), promoter of the *Solanum tuberosum* gene encoding the leaf and stem specific (ST-LS1) protein (Zaidi M. A. et al., 2005 Transgenic Res. 14:289-98), stern-regulated, defense-inducible genes, such as JAS promoters (patent publication no. 20050034192/US-A1), flower-specific promoters such as chalcone synthase promoter (Faktor O. et al. 1996 Plant Mol. Biol. 32: 849) and fruit-specific promoters such as that of RJ39 from strawberry (WO 98 31812). Other suitable promoters are pathogen-induced promoters, such as nematode induced plant promoters, or feeding-site specific promoters, examples of which are Wun-1 (Hansen et al. 1996. Physiol. Mol. Plant. Pathol. 48: 161-170); Lea-14, Lemmi 9 (Van der Eycken W et al. Plant J. 1996 9 (1): 45-54; Escobar C et al. Mol Plant Microbe Interact. 1999, 12 (5):440-9), pin-2 (Keil et al. 1989. EMBO J. 8:1323-1330) and TobRB7 (Opperman et al. 1994. Science, 263: 221-223).

According to one embodiment of the invention, the vectors comprise a constitutive promoter. According to another embodiment of the invention, the vectors comprise an inducible promoter. According to another embodiment of the invention, the vectors comprise a tissue-specific promoter, for instance a root-specific promoter in case of alleviating pest infestations where the pest predominantly feeds on the roots of the plant, or for instance a leaf-specific promoter in case of alleviating pest infestations where the pest predominantly feeds on the leafs of the plant. Promoters which initiate transcription only in certain tissues or cells are herein referred to 'tissue-specific or "cell-specific" promoters, respectively. In addition, the present invention relates to a vector according to the invention wherein the promoter is selected from the group comprising tissue specific promoters such as any selected from the group comprising root specific promoters of genes encoding PsMTA Class III Chitinase, photosynthetic tissue-specific promoters such as promoters of cab1 and cab2, rbcS, gapA, gapB and ST-LS1 proteins, JAS promoters, chalcone synthase promoter and the promoter of RJ39 from strawberry.

Optionally, one or more transcription termination sequences may also be incorporated in the expression construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

The expression constructs of the invention may further include an origin of replication which is required for maintenance and/r replication in a specific cell type. One example is when an expression construct is required to be maintained in a bacterial cell as an episomal genetic element (e.g. plasmid or cosmid molecule). Preferred origins of replication include, but are not limited to the f1-ori and colE1 ori.

The expression construct may optionally comprise a selectable marker gene. As used herein, the term "selectable marker gene" includes any gene, which confers a phenotype on a cell in which it is expressed to facilitate the identification and/or selection of cells which are transfected or transformed with an expression construct of the invention. Suitable markers may be selected from markers that confer antibiotic or herbicide resistance or visual markers. Examples of selectable marker genes include genes encoding neomycin phosphotransferase (nptII), hygromycin phosphotransferase (hpt) or Basta. Further examples of suitable selectable marker genes include resistance genes against ampicillin (Ampr), tetracydine (Tcr), kanamycin (Kanr), phosphinothricin, and chloramphenicol (CAT). Other suitable marker genes provide a metabolic trait, for example manA. Visual marker genes may also be used and include for example beta-glucuronidase (GUS), luciferase and Green Fluorescent Protein (GFP).

Expression of Chimeric RNAi Molecules in Plant Organelles

According to a preferred embodiment of the invention, the RNA delivery molecule and/or the chimeric RNAi molecules are expressed in plant cell organelles to protect dsRNA from processing.

According to a further embodiment, the nucleic acids encoding the RNA delivery molecule and/or the chimeric RNAi molecules may further comprise an in frame signal sequence for directing the encoded polypeptide to a plant organel, such as a chloroplast, a plastide, or a mitochondrion, for instance signaling the chimeric RNAi molecule towards an intracellular compartment of the host cell in another mechanism to protect dsRNA from processing For example, the RNA delivery molecule, and/or the chimeric RNAi molecule, and/or the complex between the RNA delivery molecule and the chimeric RNAi molecule can be compartmentalized in an intermediate host cell or organism before it is transferred to the target host cell, e.g. a pest cell. It shall be understood that the RNA delivery molecule and the chimeric RNAi molecule may be directed to the same or to different organelles of an intermediate host cell.

In particular, the RNA delivery molecule, and/or the chimeric RNAi molecule, and/or the complex between the RNA delivery molecule may be compartmentalized in a plant cell, for instance it may be located in the chloroplast, mitochondrion or plastid, before it is transferred to the plant pest species, for example a plant pest nematode or insect. Compartmentalization may occur in a variety of ways, such as for example via the use of viroid structures, or via the use of signal sequences as described above, for example chloroplast, mitochondrial or plastid signal sequences. These organelles are form prokaryotic origin and may offer a protective environment away from the plant RNA processing machinery.

A major advantage of compartmentalization of the RNA delivery molecule, and/or the chimeric RNAi molecule, and/ or the complex between the RNA delivery molecule thus include that the molecules of the complex are protected from nuclear/cytoplasmic processing (dicing) of dsRNA. In addition, compartmentalization provides for an accumulation of dsRNA sequences.

Compartmentalized Expression of Sense and Antisense Target RNA

In yet another mechanism to protect the dsRNA contained within the chimeric RNAi molecule from RNA processing is to express sense and antisense separately and to target them to different locations within the host cell or organism that expresses the sense and the antisense strands. In the context of the present invention, the sense or the antisense strand is part of the chimeric RNAi molecule. In this embodiment, sense and antisense RNA fragments corresponding to a selected gene of a particular pest species are cloned behind different promoters driving expression (i) separate plant tissues or (ii) within the same cell but in separate cellular compartments. These promoters are tissue or organel specific and allow strong simultaneous expression in different cellular compartments or in adjacent tissues.

For example, the sense and antisense strands may be targeted to different plant tissue or cell types. For example, in a leaf the sense strand may be expressed in the nerve cells while the antisense is expressed in the palisade tissue. This may be achieved by using different promoters to drive the expression of the sense and the antisense strands. The advantage of this technique is that the sense and antisense strands never come together in the plant cell, and therefore no degradation or auto-silencing or RNA interference can occur within the plant by Dicer. When the pest organism feeds on the plant, the strands are set free and mixed, allowing the annealing of the dsRNA in the gut lumen and then base pairing between the sense and antisense strands may occur to form long dsRNA. Subsequently, this dsRNA may be taken up efficiently and leads to the desired RNAi response, leading to degradation of the target mRNA in the pest and death of the pest. This approach can be accomplished by feeding the pest with two bacterial strains for instance provided in a composition, one strain producing the sense, the other producing the antisense strand.

Host Cells

In another embodiment, the present invention relates to a host cell or organism comprising a nucleic acid or a vector as defined herein. Examples of host cells which may be used in accordance with the present invention include a bacterial, yeast, fungal, or plant cell. Host cells may be prokaryotic cells such as *E. coli* and *A. tumefaciens*, or may be eukaryotic cells such as yeast, or plant cells. It is preferred that host cells are monocotyledonous or dicotyledonous plant cells.

Accordingly, the present invention also encompasses a cell, e.g. a host cell, comprising any of the chimeric RNAi molecules, RNA delivery molecule, dsRNA, nucleic acid or a vector as defined herein. The invention further encompasses prokaryotic cells (such as, but not limited to, gram-positive and gram-negative bacterial cells) and eukaryotic cells (such as, but not limited to, yeast cells or plant cells). Preferably, said cell is a bacterial cell or a plant cell. The present invention also encompasses a transgenic plant, reproductive or propagation material for a transgenic plant comprising such a plant cell.

The vector or nucleic acid molecule according to the invention may either be integrated into the genome of the host cell or it may be maintained in some form extrachromosomally.

E. Complex Between RNA Delivery Molecule and the Chimeric RNAi Molecule

In another aspect, the present invention relates to a complex comprising:
 an RNA delivery molecule as defined herein, and
 at least one chimeric RNAi molecule comprising
  at least a double-stranded RNA comprising annealed complementary strands, one of which has a nucleotide sequence which is complementary to at least part of a target nucleotide of a target gene of said pest species (i.e. capable of causing RNAi interference) and
  a sequence recognized by an RNA binding protein or RNA binding domain, for instance as represented in any of SEQ ID NOs 15 to 40, or as represented in FIG. 41 or 42.

In another embodiment, the present invention relates to a complex comprising:
 an RNA delivery molecule as defined herein, and
 at least one chimeric RNAi molecule as represented by any of SEQ ID NOs 41 to 52 or any of SEQ ID NOs 54 to 56, or any of SEQ ID NOs 57 to 71, or any of SEQ ID NOs 72 to 86,
provided that the RNA delivery molecule is recognized and may bind to the RNA binding protein or RNA binding domain of the RNA delivery molecule.

It is to be understood that said complex is provided in such a condition that binding may occur between said RNA delivery molecule and said chimeric RNAi molecule. This complex is also referred to in the present invention as the "protein-RNA complex" or the "complex between the RNA delivery molecule and the chimeric RNAi", or the "RNA vehicle complex (RVC)".

It should be understood that in the above-described complexes of the invention comprising both an RNA delivery molecule and a chimeric RNAi molecule, the sequences of the molecules should be such that the RNA binding protein or RNA binding domain in the RNA delivery molecule recognizes and is able to bind to the RNA recognition site, specific for the RNA binding protein or RNA binding domain, in the chimeric RNAi molecule.

In one specific embodiment, the invention relates to a complex between an RNA delivery molecule and a chimeric RNAi molecule, wherein the RNA-binding domain of the RNA delivery molecule comprises the coliphage HK022 Nun protein or a fragment thereof, said fragment comprising the RNA-binding domain of the HK022 Nun protein, and wherein the chimeric RNAi molecule comprising the double stranded RNA molecule further comprises a nucleotide sequence corresponding to the binding motif for binding to the coliphage HK022 Nun protein or the fragment thereof. In a preferred embodiment, the RNA-binding domain is a polypeptide comprising the sequence represented in any of SEQ ID NOs 2, 4, 6, 8 or 87, most preferably comprising the sequence represented in SEQ ID NO 8, and the chimeric RNAi molecule comprising the double stranded RNA further comprises the binding motif represented in SEQ ID NO 15 or 16. In another preferred embodiment, the RNA-binding domain is a polypeptide comprising the sequence represented in any of SEQ ID NOs 2, 4, 6, 8 or 87, most preferably comprising the sequence represented in SEQ ID NO 8, and the chimeric RNAi molecule is any of the chimeric RNAi molecules as represented by any of SEQ ID NOs 45 to 48, 55, 61 to 64, 70, 76 to 79, and 85.

In another preferred embodiment, the invention relates to a complex between an RNA delivery molecule and a chimeric RNAi molecule wherein the RNA-binding domain of the RNA delivery molecule is the *Bacillus subtilis* LicT protein or a fragment thereof, said fragment comprising the RNA binding domain and wherein the chimeric RNAi molecule comprising the double stranded RNA molecule comprises a nucleotide sequence corresponding to the binding motif for binding to the *Bacillus subtilis* LicT protein or the fragment thereof. In a preferred embodiment the RNA binding domain is a polypeptide comprising the sequence represented in SEQ ID NO 10 or 12, preferably a polypeptide comprising the sequence represented in SEQ ID NO 12, and the chimeric RNAi molecule comprising the double stranded RNA molecule comprises the binding motif represented in FIG. 41, or as represented in any of SEQ ID NOs 17 to 34. In another preferred embodiment, the RNA binding domain is a polypeptide comprising the sequence represented in SEQ ID NO 10 or 12, preferably a polypeptide comprising the sequence represented in SEQ ID NO 12, and the chimeric RNAi molecule is any of the chimeric RNAi molecules as represented by any of SEQ ID NOs 41 to 44, 54, 57 to 60, 69, 72 to 75, and 84.

In yet another preferred embodiment, the invention relates to a complex between an RNA delivery molecule and a chimeric RNAi molecule wherein the RNA-binding domain of the RNA delivery molecule is MS2 or a fragment thereof, said fragment comprising the RNA binding domain and wherein the chimeric RNAi molecule comprising the double stranded RNA molecule comprises a nucleotide sequence corresponding to the binding motif for binding to MS2 or the fragment thereof. In a preferred embodiment, the RNA binding domain is a polypeptide comprising the sequence represented in SEQ ID NO 14 and the chimeric RNAi molecule comprising the double stranded RNA molecule comprises the binding motif represented in FIG. 42, or as represented in any of SEQ ID NOs 35 to 40. In another preferred embodiment, the RNA binding domain is a polypeptide comprising the sequence represented in SEQ ID NO 14, and the chimeric RNAi molecule is any of the chimeric RNAi molecules as represented by any of SEQ ID NOs 49 to 52, 56, 65 to 68, 71, 81 to 83, and 86.

Table 5 provides an overview of specific embodiments of complexes according to the invention comprising an RNA delivery molecule showing a specific RNA binding domain, combined with a chimeric RNAi molecule comprising RNA sequences that are recognized by said specific RNA binding domain of the RNA delivery molecule as indicated in Table 5.

TABLE 5

| RNA binding domain of the RNA delivery molecule | RNA sequences recognized by RNA binding domain |
|---|---|
| SEQ ID NOs 2, 4, 6 or 8 (coliphage HK022 Nun protein (*)) | SEQ ID NO 15 and 16 |
| SEQ ID NO 10 or 12 (*Bacillus subtilis* LicT protein (*)) | SEQ ID NOs 17 to 34 |
| SEQ ID NO 14 (bacteriophage MS2 coat protein (*)) | SEQ ID NOs 35 to 40 |
| SEQ ID NO 87 (N-terminal domain of Bacteriophage λ N protein) | SEQ ID NO 15 and 16 |

(*) or essential parts, or homologues thereof

Table 6 provides an overview of other specific embodiments of complexes according to the invention comprising an RNA delivery molecule containing an RNA binding domain, combined with a specific chimeric RNAi molecule as indicated in Table 6.

TABLE 6

| RNA binding domain of the RNA delivery molecule amino acid sequences | chimeric RNAi molecule nucleic acid sequences |
|---|---|
| SEQ ID NOs 2, 4, 6 or 8 (coliphage HK022 Nun protein (*)) | SEQ ID NOs 45, 46, 47, 48, 55, 61, 62, 63, 64, 70, 76, 77, 78, 79, 85 |
| SEQ ID NO 10 or 12 (*Bacillus subtilis* LicT protein (*)) | SEQ ID NOs 41, 42, 43, 44, 54, 57, 58, 59, 60, 69, 72, 73, 74, 75, 84 |
| SEQ ID NO 14 (bacteriophage MS2 coat protein (*)) | SEQ ID NOs 49, 50, 51, 52, 56, 65, 66, 67, 68, 71, 80, 81, 82, 83, 84, 86 |

(*) or essential parts, or homologues thereof

It shall be understood from the present description that the present RNA delivery molecules are particularly suitable for improving the delivery of dsRNA to pest organisms which are feeding on a plant expressing dsRNA for the purpose of eliciting RNA interference in the pest organism.

In one embodiment the present invention relates to an RNA delivery molecule comprising a fusion protein which consists of an RNA binding domain fused, preferably by means of a linker polypeptide, to a targeting module. Preferably said targeting module comprises a domain that is endocytosed in the gut of a target organism. The present RNA delivery molecule is capable of forming a complex with the chimeric RNAi molecule comprising dsRNA for the purpose of interference.

In another embodiment the present invention relates to an RNA delivery molecule comprising a fusion protein which consists of an RNA binding domain fused preferably by means of a linker polypeptide, to a domain that is transcytosed from the gut to the haemolymph or coelumic fluid of a target organism. The present RNA delivery molecule is capable of forming a complex with the chimeric RNAi molecule comprising dsRNA for the purpose of interference.

F. Methods

The present invention relates to methods for delivering dsRNA to a pest species, to methods for down-regulating the expression of a target gene in a pest species and to methods for producing transgenic plants resistant to pest species.

Methods according to the present invention include feeding the RNA delivery molecules to the organism to deliver the dsRNA to the organism tissues. It is envisaged that the methods of the invention will have use in controlling plant diseases caused by feeding organisms. Methods of pest control of organisms, and of protecting plants against organisms are provided.

The RNA delivery molecule and the dsRNA for purposes of RNA interference may be taken up by the pest organism in several ways.

The invention relates to methods for delivering one or more double-stranded RNA molecules to a pest species, comprising:

co-expressing in a plant cell of:
a) an RNA delivery molecule according to the invention, and
b) an RNA molecule which comprises double-stranded RNA comprising annealed complementary strands, one of which has a nucleotide sequence which is complementary to at least part of a target nucleotide sequence of a target gene of the pest species, and which further comprises a nucleotide sequence which binds to the RNA-binding domain of the RNA delivery molecule of (a), and feeding said plant cell to said pest species.

In another embodiment, a method is provided for delivering double-stranded RNA to a pest species, comprising feeding the pest species with a mixture of an RNA molecule and an RNA delivery molecule according to the present invention, wherein the RNA molecule comprises double-stranded RNA comprising annealed complementary strands, one of which has a nucleotide sequence which is complementary to at least part of a target nucleotide sequence of a target gene of the pest species, and further comprises a nucleotide sequence which binds to the RNA-binding domain of the RNA delivery molecule, whereby the mixture is taken up into the gut of the pest species, and whereby the complex of the double-stranded RNA bound to the RNA delivery molecule is transcytosed and/or endocytosed by a gut cell and/or a tissue cell.

In one embodiment the invention also relates to a method for down-regulating expression of a target gene in a pest species, comprising feeding the pest species with a mixture of an RNA molecule and an RNA delivery molecule according to the present invention, wherein the RNA molecule comprises double-stranded RNA comprising annealed complementary strands, one of which has a nucleotide sequence which is complementary to at least part of a target nucleotide sequence of the target gene to be down-regulated, and further comprises a sequence which binds to the RNA-binding domain of the RNA delivery molecule, whereby the mixture is taken up into the gut of the pest species, and whereby the complex of the double stranded RNA bound to the RNA delivery molecule is transcytosed and/or endocytosed by a gut cell and/or a tissue cell and thereby down-regulates expression of the target gene in a pest cell.

In yet another embodiment, a method is provided for delivering double-stranded RNA to a pest species, comprising feeding the pest species with a complex comprising an RNA delivery molecule as defined herein, and at least one chimeric RNAi molecule consisting of an RNA molecule wherein the RNA molecule comprises double-stranded RNA comprising annealed complementary strands, one of which has a nucleotide sequence which is complementary to at least part of a target nucleotide sequence of the target gene to be down-regulated, and further comprises a sequence which binds to the RNA-binding domain of the RNA delivery molecule, whereby the complex is taken up into the gut of the pest species, and whereby the complex of the double-stranded RNA bound to the RNA delivery molecule is transcytosed and/or endocytosed by a gut cell and/or a tissue cell.

The term "feeding" according to the present invention may refer to feeding of the pest species with a host cell or organism, e.g. plant cell, bacteria, fungi, yeast, etc., or a mixture thereof comprising or expressing, sprayed with or coated with at least one RNA delivery molecule and/or chimeric RNAi molecule of the invention. In one embodiment, a mixture of bacteria or plant(s) cell(s) may be fed to a pest species, whereby the mixture comprises at least one bacterium or plant (cell) that comprises or expresses an RNA delivery molecule and at least another bacterium or plant (cell) that comprises or expresses a chimeric RNAi molecule.

In yet another embodiment, the invention relates to a method for down-regulating expression of a target gene in a pest species, comprising:

co-expressing in a plant cell of:
(a) an RNA delivery molecule according to the invention,
(b) an RNA molecule which comprises double-stranded RNA comprising annealed complementary strands, one of which has a nucleotide sequence which is complementary to at least part of a target nucleotide sequence of the target gene to be down-regulated, and which further comprises a nucleotide sequence which binds to the RNA-binding domain of the RNA delivery molecule of (a), and feeding said plant cell to said pest species.

In more specific embodiments, the invention relates to any of the methods described above wherein the RNA-binding domain of an RNA delivery molecule (a) comprises the coliphage HK022 Nun protein or a fragment thereof, said fragment comprising the RNA-binding domain of the HK022 Nun protein, and wherein the double stranded RNA molecule (b) comprises a nucleotide sequence corresponding to the binding motif for binding to the coliphage HK022 Nun protein or the fragment thereof. Even more specific, the invention relates to such a method wherein the RNA-binding domain is a polypeptide comprising the sequence represented in any of SEQ ID NOs 2, 4, 6, a or 87, preferably comprising the sequence represented in SEQ ID NO 8, and wherein the double stranded RNA molecule (b) comprises the binding motif represented in SEQ ID NO 15 or 16.

In other specific embodiments, the invention relates to any of the methods described above wherein in (a) the RNA binding domain is the *Bacillus subtilis* LicT protein or a fragment thereof, said fragment comprising the RNA binding domain and wherein the double stranded RNA molecule (b) comprises a nucleotide sequence corresponding to the binding motif for binding to the *Bacillus subtilis* LicT protein or the fragment thereof. Even more specific, the invention relates to such a method wherein the RNA binding domain is a polypeptide comprising the sequence represented in SEQ ID NO 10 or 12, preferably a polypeptide comprising the sequence represented in SEQ ID NO 12, and wherein the double stranded RNA molecule (b) comprises the binding motif represented in FIG. 41, or as represented in any of SEC ID NOs 17 to 34.

In other specific embodiments, the invention relates to any of the methods described above wherein in (a) the RNA binding polypeptide is MS2 or a fragment thereof said fragment comprising the RNA binding domain and double stranded RNA molecule (b) comprises a nucleotide sequence corresponding with the binding motif for binding to MS2 or the fragment thereof. Even more specific, the invention relates to such a method wherein in (a) the RNA binding domain is a polypeptide comprising the sequence represented in SEQ ID NO 14, and wherein (b) comprises the binding motif represented in FIG. 42 or as represented in any of SEQ ID NOs 35 to 40.

A method for producing a transgenic plant that is resistant to a pest species, comprising:

co-expressing in a plant cell or plant tissue of:
(a) an RNA delivery molecule according to the present invention, and
(b) an RNA molecule which comprises double-stranded RNA comprising annealed complementary strands, one of which has a nucleotide sequence which is complementary to at least part of a target nucleotide sequence of the target gene of said pest species, and which further comprises a nucleotide sequence which binds to the RNA-binding domain of the RNA delivery molecule of (a), and regenerating a plant from said plant cell or plant tissue.

In more specific embodiments, the invention relates to any of the methods described above for producing a transgenic plant that is resistant to a pest species, where in the RNA-binding domain of an RNA delivery molecule (a) comprises the coliphage HK022 Nun protein or a fragment thereof, said fragment comprising the RNA-binding domain of the HK022 Nun protein, and wherein the double stranded RNA molecule (b) comprises a nucleotide sequence corresponding to the binding motif for binding to the coliphage HK022 Nun protein or the fragment thereof. Even more specific, the invention relates to such a method wherein the RNA-binding domain is a polypeptide comprising the sequence represented in any of SEQ ID NOs 2, 4, 6, 8 or 87, preferably comprising the sequence represented in SEQ ID NO 8, and wherein the double stranded RNA molecule (b) comprises the binding motif represented in SEQ ID NO 15 or 16.

In other specific embodiments, the invention relates to any of the methods described above for producing a transgenic plant that is resistant to a pest species wherein in (a) the RNA binding domain is the *Bacillus subtilis* LicT protein or a fragment thereof, said fragment comprising the RNA binding domain and wherein the double stranded RNA molecule (b) comprises a nucleotide sequence corresponding to the binding motif for binding to the *Bacillus subtilis* LicT protein or the fragment thereof. Even more specific, the invention relates to such a method wherein the RNA binding domain is a polypeptide comprising the sequence represented in SEQ ID NO 10 or 12, preferably a polypeptide comprising the sequence represented in SEQ ID NO 12, and wherein the double stranded RNA molecule (b) comprises the binding motif represented in FIG. 41, or as represented in any of SEQ ID NOs 17 to 34.

In other specific embodiments, the invention relates to any of the methods described above for producing a transgenic plant that is resistant to a pest species wherein in (a) the RNA binding polypeptide is MS2 or a fragment thereof said fragment comprising the RNA binding domain and double stranded RNA molecule (b) comprises a nucleotide sequence corresponding with the binding motif for binding to MS2 or the fragment thereof. Even more specific, the invention relates to such a method wherein in (a) the RNA binding domain is a polypeptide comprising the sequence represented in SEQ ID NO 14, and wherein (b) comprises the binding motif represented in FIG. 42 or as represented in any of SEQ ID NOs 35 to 40.

In yet another embodiment, the method for producing a transgenic plant that is resistant to a pest species, comprises:
co-expressing in a plant cell or plant tissue of:
a) an RNA delivery molecule according to the present invention, and
b) a chimeric RNAi molecule according to the present invention and preferably comprising
at least one nucleotide sequence recognized by an RNA-binding protein or RNA-binding domain, for instance as represented in any of SEQ ID NOs 15 to 40, or an RNA secondary structure as represented in FIG. 41 or 42, and
at least one nucleotide sequence corresponding to a target nucleotide sequence of a target gene of a pest species, and
regenerating a plant from said plant cell or plant tissue.

Even more specific, the invention relates to such a method for producing a transgenic plant that is resistant to a pest species wherein said chimeric RNAi molecule is a molecule as described in Example 2. According to further specific embodiments, the invention relates to such a method for producing a transgenic plant that is resistant to a pest species wherein said chimeric RNAi molecule has a sequence as represented any of FIGS. 43 to 54 (any of SEQ ID NOs 41 to 52) or FIGS. 56 to 58 (any of SEQ ID NOs 54 to 56), or any of FIGS. 60 to 74 (any of SEQ ID NOs 57 to 71), or any of FIGS. 76 to 90 (any of SEQ ID NOs 72 to 86). In this context it should be understood that the chimeric RNAi molecule is recognized and able to be bound by the RNA binding protein or RNA binding domain present in the RNA delivery molecule according to the invention.

Thus, the present invention provides for methods for the production of transgenic plants, plant cells or plant tissues comprising the introduction of a nucleic acid or vector according to the invention into the genome of said plant, plant cell or plant tissue.

The present invention also relates to a transgenic plant resistant to a pest species, an essential derived variety thereof, plant part, plant cell or protoplast thereof obtainable by any of the methods as described herein.

In another embodiment, the invention relates to a transgenic plant, essentially derived variety thereof, plant part, plant cell or protoplast thereof which comprises a nucleic acid encoding an RNA delivery molecule as defined herein, wherein said nucleic acid is heterologous to the genome of said transgenic plant, or an essentially derived variety thereof, plant part, plant cell or plant protoplast thereof.

The invention also relates to a transgenic plant, essentially derived variety thereof, plant part, plant cell or protoplast thereof which comprises a nucleic acid encoding an RNA delivery molecule as defined herein, and which comprises a nucleic acid encoding a chimeric RNAi molecule as defined herein, wherein said nucleic acids are heterologous to the genome of said transgenic plant, or an essentially derived variety thereof, plant part, plant cell or plant protoplast thereof.

In yet another embodiment, the invention provides a transgenic plant which comprises a vector as described herein.

As used herein, 'transgenic plant' includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a vector. 'Transgenic' is used herein to include any cell, cell line, callus, tissue, plant part or plant, the genotype of which has been altered by the presence of the heterologous nucleic acid including those transgenics initially so altered as well as those created by sexual crosses or asexual propagation from the initial transgenic.

In another embodiment of the invention, there is provided a plant, essentially derived variety thereof, plant part, plant cell or protoplast thereof wherein the plant, essentially derived variety thereof, plant part, plant cell, or protoplast thereof has been transformed with a nucleic acid encoding an RNA delivery molecule as defined herein, and optionally also with a nucleic acid encoding a corresponding chimeric RNAi molecule as described herein.

The present invention also provides a plant, essentially derived variety thereof, plant part, plant cell, or protoplast thereof which co-expresses:
a) an RNA delivery molecule as described herein, and
b) an RNA molecule which comprises double-stranded RNA comprising annealed complementary strands, one of which has a nucleotide sequence which is complementary to at least part of a target nucleotide sequence of a target gene in a pest species, and which further comprises a nucleotide sequence which binds to the RNA-binding domain of the RNA delivery molecule of (a).

In another embodiment of the invention also provides a plant, essentially derived variety thereof, plant part, plant cell, or protoplast thereof which co-expresses:
a) an RNA delivery molecule as defined herein, and
b) a chimeric RNAi molecule according to the present invention and preferably comprising at least one nucleotide sequence recognized by an RNA-binding protein c) r RNA-binding domain, for instance as represented in any of SEQ ID NOs 15 to 40, or an RNA secondary structure as represented in FIG. 41 or 42, and at least one nucleotide sequence corresponding to a target nucleotide sequence of a target gene of a pest species.

Even more specific, the invention relates to a plant, essentially derived variety thereof, plant part, plant cell, or protoplast thereof which co-expresses an RNA delivery molecule as defined herein, and a chimeric RNAi molecule according to the present invention, wherein said chimeric RNAi molecule has a sequence as represented any of FIGS. 43 to 54 (any of SEQ ID NOs 41 to 52) or FIGS. 56 to 58 (any of SEQ ID NOs 54 to 56), or any of FIGS. 60 to 74 (any of SEQ ID NOs 57 to 71), or any of FIGS. 76 to 90 (any of SEQ ID NOs 72 to 86). In this context it should be understood that the chimeric RNAi molecule is recognized and able to be bound by the RNA binding protein or RNA binding domain present in the RNA delivery molecule according to the invention.

In one specific embodiment, the invention relates to a plant, essentially derived variety thereof, plant part, plant cell, or protoplast thereof which co-expresses an RNA delivery molecule as defined herein, and a chimeric RNAi molecule according to the present invention, wherein the RNA-binding domain of the RNA delivery molecule comprises the coliphage HK022 Nun protein or a fragment thereof, said fragment comprising the RNA-binding domain of the HK022 Nun protein, and wherein the chimeric RNAi molecule comprises a nucleotide sequence corresponding to the binding motif for binding to the coliphage HK022 Nun protein or the fragment thereof. In a preferred embodiment, the RNA-binding domain is a polypeptide comprising the sequence represented in any of SEQ ID NOs 2, 4, 6, 8 or 87, most preferably comprising the sequence represented in SEQ ID NO 8, and the chimeric RNAi molecule comprises the binding motif represented in SEQ ID NO 15 or 16. In another preferred embodiment, the RNA-binding domain is a polypeptide comprising the sequence represented in any of SEQ ID NOs 2, 4, 6, 8 or 87 most preferably comprising the sequence represented in SEQ ID NO 8, and the chimeric RNAi molecule is any of the chimeric RNAi molecules as represented by any of SEQ ID NOs 45 to 48, 55, 61 to 64, 70, 76 to 79, and 85.

In another specific embodiment, the invention relates to a plant, essentially derived variety thereof, plant part, plant cell, or protoplast thereof which co-expresses an RNA delivery molecule as defined herein, and a chimeric RNAi molecule according to the present invention, wherein the RNA-binding domain of the RNA delivery molecule is the *Bacillus subtilis* LicT protein or a fragment thereof, said fragment comprising the RNA binding domain and wherein the chimeric RNAi molecule le comprises a nucleotide sequence corresponding to the binding motif for binding to the *Bacillus subtilis* LicT protein or the fragment thereof. In a preferred embodiment the RNA binding domain is a polypeptide comprising the sequence represented in SEQ ID NO 10 or 12, preferably a polypeptide comprising the sequence represented in SEQ ID NO 12, and the chimeric RNAi molecule comprises the binding motif represented in FIG. 41, or as represented in any of SEQ ID NOs 17 to 34. In another preferred embodiment, the RNA binding domain is a polypeptide comprising the sequence represented in SEQ ID NO 10 or 12, preferably a polypeptide comprising the sequence represented in SEQ ID NO 12, and the chimeric RNAi molecule is any of the chimeric RNAi molecules as represented by any of SEQ ID NOs 41 to 44, 54, 57 to 60, 69, 72 to 75 and 84.

In yet another specific embodiment, the invention relates to a plant, essentially derived variety thereof, plant part, plant cell, or protoplast thereof which co-expresses an RNA delivery molecule as defined herein, and a chimeric RNAi molecule according to the present invention, wherein the RNA-binding domain of the RNA delivery molecule is MS2 or a fragment thereof, said fragment comprising the RNA binding domain and wherein the chimeric RNAi molecule comprises a nucleotide sequence corresponding to the binding motif for binding to MS2 or the fragment thereof. In a preferred embodiment, the RNA binding domain is a polypeptide comprising the sequence represented in SEQ ID NO 14 and the chimeric RNAi molecule comprises the binding motif represented in FIG. 42, or as represented in any of SEQ ID NOs 35 to 40. In another preferred embodiment, the RNA binding domain is a polypeptide comprising the sequence represented in SEQ ID NO 14, and the chimeric RNAi molecule is any of the chimeric RNAi molecules as represented by any of SEQ ID NOs 49 to 52, 56, 65 to 68, 71, 80 to 83 and 86.

The term "transformation" as used herein, refers to the transfer of an exogenous polynucleotide into a host cell, irrespective of the method used for the transfer. The polynucleotide may be transiently or stably introduced into the host cell or organism and may be maintained non-integrated, for example, as a plasmid, or alternatively, may be integrated into the host genome. Transformation may be transient or stable. The invention thus also relates to such a stably or transiently transformed transgenic plant, plant cell or plant tissue. The invention further relates to any plant which comprises any of the subject vectors in accordance with the invention.

According to a further embodiment, the invention also relates to any of the transgenic plants described herein comprising a nucleic acid encoding an RNA delivery molecule as defined herein characterized in that said plant has increased resistance to a pest organism, for instance increased resistance of between 30% to 80% compared to control plants.

In other embodiments, the invention also relates to the progeny of a plant or essentially derived variety thereof obtainable by a method of the present invention or as described herein which has been obtained in a generative or vegetative manner.

The present invention also includes parts or derivatives of obtainable by a method of the present invention or as described herein, such as but not limited to leaves, sterns, roots, shoots, cuttings or explants and the like, protoplasts, somatic embryos, anthers, petioles, cells in culture, seeds, flowers, fruits and tubers.

In another embodiment the invention relates to a method for controlling a pest species comprising feeding said pest species with a mixture of an RNA molecule and an RNA delivery molecule as defined herein, wherein the RNA molecule comprises double-stranded RNA comprising annealed complementary strands, one of which has a nucleotide sequence which is complementary to at least part of a target nucleotide sequence of the target gene of said pest species and further comprises a nucleotide sequence which binds to the RNA-binding domain of the RNA delivery molecule, whereby the mixture is taken up into the gut of the pest species, and whereby a complex is formed between the double-stranded RNA of said RNA molecule and said RNA delivery molecule, whereby the complex of the double-stranded RNA bound to the RNA delivery molecule is transcytosed and/or endocytosed by a gut cell and/or a tissue cell; and whereby the double-stranded RNA causes RNAi interference with the target gene in a pest cell such that the pest species is killed or paralyzed.

In yet another embodiment the invention relates to a method for controlling a pest species comprising feeding the pest species with a complex comprising an RNA delivery molecule as defined herein, and at least one chimeric RNAi molecule consisting of an RNA molecule wherein the RNA molecule comprises double-stranded RNA comprising annealed complementary strands, one of which has a nucleotide sequence which is complementary to at least part of a target nucleotide sequence of the target gene to be down-regulated, and further comprises a sequence which binds to the RNA-binding domain of the RNA delivery molecule, whereby the complex is taken up into the gut of the pest species, and whereby the complex of the double-stranded RNA bound to the RNA delivery molecule is transcytosed and/or endocytosed by a gut cell and/or a tissue cell, and whereby the double-stranded RNA causes RNAi interference with the target gene in a pest cell such that the pest species is killed or paralyzed.

In yet another embodiment the invention also relates to a method for controlling a pest species comprising feeding the pest species with a transgenic plant or any progeny or part thereof as defined herein which is resistant to said pest species.

In yet another embodiment a method is provided for protecting a plant against a pest organism comprising co-expressing in said plant of:

a) an RNA delivery molecule as defined herein, and b) an RNA molecule which comprises double-stranded RNA comprising annealed complementary strands, one of which has a nucleotide sequence which is complementary to at least part of a target nucleotide sequence of the target gene to be down-regulated, and which further comprises a nucleotide sequence which binds to the RNA-binding domain of the RNA delivery molecule of (a).

In yet another embodiment a method is provided for protecting a plant against a pest organism comprising co-expressing in said plant a) an RNA delivery molecule as defined herein, and b) a chimeric RNAi molecule according to the present invention and preferably comprising at least one nucleotide sequence recognized by an RNA-binding protein or RNA-binding domain, for instance as represented in any of SEQ ID NOs 15 to 40, or an RNA secondary structure as represented in FIG. 41 or 42, and at least one nucleotide sequence corresponding to a target nucleotide sequence of a target gene of a pest species.

Even more specific, said chimeric RNAi molecule has a sequence as represented in any of FIGS. 43 to 54 (any of SEQ ID NOs 41 to 52) or FIGS. 56 to 58 (any of SEQ ID NOs 54 to 56), or in any of FIGS. 60 to 74 (any of SEQ ID NOs 57 to 71), or in any of FIGS. 76 to 90 (any of SEQ ID NOs 72 to 86). In this context it should be understood that the chimeric RNAi molecule is recognized and able to be bound by the RNA binding protein or RNA binding domain present in the RNA delivery molecule according to the invention.

The invention further relates to any of the methods described herein wherein the said pest species is any pest species described herein.

Plants

In a preferred embodiment the host organism is a plant and the pest species is a plant pathogenic pest.

The term 'plant' as used herein encompasses any plant material such as inter alia a plant cell, plant tissue (including callus), plant part, whole plant, ancestors and progeny. A plant part may be any part or organ of the plant and include for example a seed, fruit, stem, leaf, shoot, flower, anther, root or tuber. The plant material should express, or have the capability to express, RNA delivery molecules, chimeric RNAi molecules, and dsRNA corresponding to one or more target genes of the pest species to be killed or paralyzed. The term "plant" also encompasses suspension cultures, embryos, meristematic regions, callus tissue, gametophytes, sporophytes, pollen, and microspores. The plant as used herein refers to all plants including algae, ferns and trees. In a preferred embodiment the plant belongs to the superfamily of Viridiplantae, further preferably is a monocot or a dicot. According to one embodiment of the present invention, the plant is susceptible to infestation by a plant pathogenic and/or parasitic nematode, by a fungus or an insect. Particular plants useful in the methods of the present invention are crop plants including for example monocots such as sugar cane and cereals (including wheat, oats, barley, sorghum, rye, millet, corn, rice) and dicots such as potato, tomato, vine, apple, pear, banana, sunflower, soybean, canola, alfalfa, rapeseed and cotton. Particular trees that can be used in the methods of the present invention are pine, eucalyptus and poplar.

"Administering" a DNA to a cell may be achieved by a variety of means, each well known by the person skilled in the art. Examples of useful techniques are shot-gun, ballistics, electroporation, transfection and transformation. For particular embodiments of the present invention where the cell is a plant cell, general techniques for expression of exogenous double-stranded RNA in plants for the purposes of RNAi are known in the art (Baulcombe D, 2004, Nature. 431 (7006): 356-63. RNA silencing in plants the contents of which are incorporated herein by reference). General techniques for expression of proteins in plants are known in the art (Fischer R et al. 1999, Biotechno. Appl. Biochem. 30 (Pt2) 99-101 and 101-108; or Cunningham C. 1997 (Ed.). Recombinant Proteins from Plants, 308p). More particularly, methods for expression of double-stranded RNA in plants for the purposes of down-regulating gene expression in plant pests such as nematodes or insects are also known in the art. Similar methods can be applied in an analogous manner in order to express the RNA delivery molecule and/or the chimeric RNAi molecule in plants for the purposes of down-regulating expression of a target gene in a plant pest species. In order to achieve this effect it is necessary only for the plant to express (transcribe) the RNA delivery molecule and/or the chimeric RNAi molecule in a part of the plant which will come into direct contact with the pest species, such that the RNA delivery molecule and/or the chimeric RNAi molecule (or the complex) can be taken up by the pest species. Depending on the nature of the pest species and its relationship with the host plant, expression of the RNA delivery molecule and/or the chimeric RNAi molecule could occur within a cell or tissue of a plant within which the pest species is also present during its life cycle, or the RNA delivery molecule and/or the chimeric RNAi molecule may be secreted into a space between cells, such as the apoplast, that is occupied by the pest species during its life cycle. Furthermore, the RNA delivery molecule and/or the chimeric RNAi molecule may be located in the plant cell, for example in the cytosol, or in the plant cell organelles such as chloroplast, mitochondrion, vacuole or endoplasmatic reticulum.

Alternatively, the RNA delivery molecule and/or the chimeric RNAi molecule may be secreted by the plant cell and by the plant to the exterior of the plant. As such, the RNA delivery molecule and/or the chimeric RNAi molecule may form a protective layer on the surface of the plant.

The present invention thus relates to a method for the production of a transgenic cell or organism, comprising the step of administering a molecule, nucleic acid or a vector as described herein to said cell or organism. Preferably, said cell is a plant cell or said organism is a plant. The invention further relates to any transgenic cell or transgenic organism obtainable by the above described method, preferably said transgenic cell or organism is plant cell or plant organism.

The methods of the present invention for the production of transgenic organism may further comprise the steps of cultivating the transgenic cell under conditions promoting growth and development. Where the transgenic organism is a plant, these methods may further comprise the steps of regenerating a plant from plant tissue, allowing growth to reach maturity and to reproduce. Alternatively, the transgenic plant tissue may take other forms or may form part of another plant, examples of which are chimera plants and grafts (for example a transformed rootstock grafted to an untransformed scion).

Advantages

Uses of the present RNA delivery molecule for delivering dsRNA from a plant to a feeding organism are numerous.

A first major advantage of the delivery system according to the present invention is that it permits to deliver dsRNA more efficiently intracellularly in target organisms. The present system enables the delivery and uptake of the chimeric RNAi molecules of the invention, comprising double stranded RNA for the purpose of RNA interference. The chimeric RNAi molecules may even comprise small RNA fragments, e.g. 21 mers, and efficiently deliver these to the gut cell of a target pest organism. Feeding a target organism dsRNA that has been bound to a delivery molecule according to the present invention and that is efficiently delivered results in an improved uptake of the dsRNA. As a result thereof, lower amounts of dsRNA need to be used in order to obtain a suitable effect in the target organism.

In the case that the RNA delivery molecule according to the present invention comprises a domain that binds a protein that is endocytosed in the gut of a target organism or that binds to an endocytosis receptor, the complex between the RNA delivery molecule and the chimeric RNAi molecule which is formed in the target organism or taken up by the target organism by feeding can enter the gut cells through endocytosis, e.g. by entering endocytic vesicles, and from there are capable of entering the cell cytoplasm. In the endosome the protein-RNA complex may be dissociated through proteolysis or pH-dependent dissociation. A fraction of the dsRNA will then enter the cell in a manner similar to the delivery mechanism for antisense RNAs, as is well known in the literature.

The gut of an insect is a hostile environment, having low or high pH values and RNases which degrade RNA. High pH such as found in lepidopteran guts degrades RNA chemically enhanced. Transcytosis of the RNA molecules to the haemolymph enables to quickly remove the dsRNA from an RNase rich and/or pH hostile environment. In the case that the RNA delivery molecule according to the present invention comprises a domain that binds a protein that is transcytosed through the gut of a target organism to the haemolymph or coelomic fluid, or that binds to a transcytosis receptor, the chimeric RNA molecules which are taken up by the target organism by feeding can enter the gut and pass through the gut to the haemolymph or coelomic fluid. Transcytosis of the chimeric RNAi molecules to the haemolymph or coelomic fluid allows to direct the dsRNA to a broad range of target tissues including muscles, CNS, and other.

In other cases, it may also be required to have a combination of endocytosis and transcytosis to have efficient and site-specific delivery of the dsRNA bound to the delivery molecule.

Another advantage of the present RNA delivery molecule is that when forming a complex with the dsRNA, it effectively protects the dsRNA molecules from degradation in the plant and in the gut of the target organism, which is a very hostile environment.

The present RNA delivery molecule may thus allow expression of long as well as short dsRNA fragments in plants, to be delivered by feeding to a target organism. Usually, long (of e.g. 80 bp or more) dsRNA fragments are expressed in a plant for delivery by feeding to a target organism. Expression of long dsRNA fragments involves several disadvantages. For instance, it makes it necessary to protect these long RNA fragments in the plant cytoplasm from Dicer activity in the endogenous plant. Dicing of longer RNA fragments may result in diced fragments that may create dominant negative effects in plants through tittering away RISC which is needed for normal plant growth and physiology, or which may down regulate plant genes or chromatic or even the transgenic dsRNA expressing gene. Smaller dsRNA molecules (even as short as 21 bp) may be effectively fed to target organisms and taken up in the gut enterocytes leading to target knockdown. As a consequence thereof, it may be not longer required to express long RNA fragments of 80 bp or longer in the plants and shorter—and thus more specific and selective—target fragments can be expressed in plants.

In addition, in the case long RNA fragments of 80 bp or longer are still to be expressed in the plants, using the present RNA delivery molecule which protect the RNA, may obviate the need of additionally protecting these fragments from dicing activity in the endogenous plant.

Another major advantage of the present delivery system is that the delivery molecule can be used for improving the delivery of chimeric RNAi molecules using a sequence or structure specific RNA binding protein. The present RNA delivery system can advantageously be used for binding different categories of RNA. In particular, the present system is capable of binding dsRNA generically, or dsRNA, ssRNA or RNA structures specifically, as long as they contain the recognition sequence or structure. In a preferred embodiment, the present RNA delivery system can be used to bind a chimeric RNAi consisting of a target specific region (target dsRNA) for the purpose of RNA interference, and an RNA sequence that specifically binds the RNA delivery molecule, and in particular the RNA binding domain thereof. Advantageously, in such case the dsRNA would not interact with plant Dicer. Use of a chimeric RNAi bound to the RNA delivery molecule of the present invention also allows the use of long RNA fragments in plants, which will not be processed to diced fragments that could induce negative side-effects in the plants as explained above. In addition, binding of a chimeric RNAi molecule to an RNA delivery molecule according to the present invention permits the transgenic dsRNA molecules to be accumulated in a selected compartment in the plant, and for instance in the nucleolus, nucleus, cytoplasm tRNA or ribosome, phloem, etc., which allows a more efficient protection, accumulation or delivery to a target organism.

G. Uses

In general, the present invention also relates to the use of RNA delivery molecules or complexes thereof with a chimeric RNAi molecule for various agronomic and research applications requiring the delivery of dsRNA into a target pest organism.

In an embodiment, the invention relates to the use of an RNA delivery molecule as described herein for delivering dsRNA to a pest species.

In another embodiment, the invention also relates to the use of an RNA delivery molecule in combination with a corresponding chimeric RNAi molecule as described herein for delivering dsRNA to a pest species.

It shall be understood from the present description that the present RNA delivery molecules are particularly suitable for improving the delivery of dsRNA to pest organisms which are feeding on a plant expressing dsRNA. Alternatively, it is apparent that the present RNA delivery molecules according to the present invention may also be very useful for improving the delivery of dsRNA to pest organisms by any other way, including but not limited to injection of dsRNA, soaking the organisms in dsRNA solution or by feeding the pest organisms *Escherichia coli* bacteria that simultaneously express sense and antisense RNAs and that can acquire dsRNA.

In yet another embodiment, the present invention relates to the use of RNA delivery molecules in combination with corresponding chimeric RNAi molecules for down-regulating the expression of target genes in pest species.

In another embodiment, the present complexes between RNA delivery molecules and corresponding chimeric RNAi molecules are also very useful for down-regulating the expression of target genes in pest species. The invention therefore also provides for the use of said complexes as described herein for down-regulating the expression of target genes in pest species.

In yet another embodiment, the invention relates to the use of an RNA delivery molecule as described herein for producing a transgenic plant.

In yet another embodiment, the present invention relates to the use of an RNA delivery molecule in combination with a chimeric RNAi molecule for producing transgenic plants resistant to pest organisms.

In another embodiment, the present complexes between an RNA delivery molecule and a corresponding chimeric RNAi molecule are also very useful for producing transgenic plants which are resistant to a pest species. The invention therefore also provides for the use of said complexes as described herein for producing transgenic plants resistant to pest organisms.

In more specific embodiments, the present invention relates to the use of a transgenic plant resistant to a pest organism as described herein for controlling pest population growth, and/or for reducing infestation by a pest species and/or for killing or paralyzing a pest organism, and/or for preventing or reducing the amount and the number of chemical (e.g. pesticide, fungicide, nematicide) applications, and/or for reducing the environmental impact of chemical applications pesticides and/or for reducing disease incidence in a crop and/or for improving crop yield.

In another embodiment the invention relates to the use of a plant, essentially derived variety thereof, plant part, plant cell or protoplast thereof that has been transformed with (i) a nucleic acid encoding an RNA delivery molecule and (ii) a nucleic acid encoding a corresponding chimeric RNAi molecule as herein described for improving resistance to a pest organism, and/or for controlling pest population growth, and/or for preventing or reducing infestation by a pest species and/or for killing or paralyzing a pest organism, and/or for reducing the amount and the number of chemical (e.g. pesticide, fungicide, nematode) applications and/or for reducing the environmental impact of chemical applications pesticides and/or for reducing disease incidence in a crop and/or for improving crop yield.

In yet another embodiment the invention relates to the use of a plant, essentially derived variety, plant part, plant cell or protoplast thereof which co-expresses:

a) an RNA delivery molecule as described herein, and
b) an RNA molecule which comprises double-stranded RNA comprising annealed complementary strands, one of which has a nucleotide sequence which is complementary to at least part of a target nucleotide sequence of a target gene of a pest species, and which further comprises a nucleotide sequence which binds to the RNA-binding domain of the RNA delivery molecule of (a), for improving resistance to pest organism, and/or for controlling pest population growth, and/or for preventing or reducing infestation by a pest species and/or for killing or paralyzing a pest organism, and/or for reducing the amount and the number of chemical (e.g. pesticide, fungicide, nematode) applications, and/or for reducing the environmental impact of chemical applications pesticides and/or for reducing disease incidence in a crop and/or for improving crop yield.

In one specific embodiment, the invention relates to any of the uses as described above, wherein the RNA-binding domain of the RNA delivery molecule comprises the coliphage HK022 Nun protein or a fragment thereof, said fragment comprising the RNA-binding domain of the HK022 Nun protein, preferably the RNA binding domain is a polypeptide comprising the sequence represented in any of SEQ ID NOs 2, 4, 6, 8 or 87, most preferably comprising the sequence represented in SEQ ID NO 8, and the RNA molecule which comprises the double stranded RNA molecule and which further comprises a nucleotide sequence corresponding to the binding motif for binding to the coliphage HK022 Nun protein or the fragment thereof, preferably the binding motif represented in SEQ ID NO 15 or 16, or more preferably the RNA molecule is any of the chimeric RNAi molecules as represented by any of SEQ ID NOs 45 to 48, 55, 61 to 64, 70, 76 to 79 and 85.

In another specific embodiment, the invention relates to any of the uses as described above, wherein the RNA-binding domain of the RNA delivery molecule is the *Bacillus subtilis* LicT protein or a fragment thereof, said fragment comprising the RNA binding domain, preferably the RNA binding domain is a polypeptide comprising the sequence represented in any of SEQ ID NO 10 or 12, most preferably comprising the sequence represented in SEQ ID NO 12, and the RNA molecule which comprises the double stranded RNA molecule comprises a nucleotide sequence corresponding to the binding motif for binding to the *Bacillus subtilis* LicT protein or the fragment thereof, preferably the binding motif represented in FIG. 41, or as represented in any of SEQ ID NOs 17 to 34, or more preferably the RNA molecule is any of the chimeric RNAi molecules as represented by any of SEQ ID NOs 41 to 44, 54, 57 to 60, 69, 72 to 75, and 84.

In yet another specific embodiment, the invention relates to any of the uses as described above, wherein the RNA-binding domain of the RNA delivery molecule is MS2 or a fragment thereof, said fragment comprising the RNA binding domain, and preferably the RNA binding domain is a polypeptide comprising the sequence represented in SEQ ID NO 14, and the RNA molecule which comprises the double stranded RNA molecule comprises a nucleotide sequence corresponding to the binding motif for binding to MS2 or the fragment thereof, and preferably the binding motif represented in FIG. 42, or as represented in any of SEQ ID NOs 35 to 40, or the RNA molecule is any of the chimeric RNAi molecules as represented by, any of SEQ ID NOs 49 to 52; 56, 65 to 68, 71, 80 to 83 and 86.

In yet another embodiment, the invention relates to the use of progeny or parts or derivatives of plants obtainable from any plant or essentially derived variety thereof as described herein for improving resistance to pest organism, and/or for controlling pest population growth, and/or for preventing or reducing infestation by a pest species and/or for killing or paralyzing a pest organism, and/or for reducing the amount and the number of chemical (e.g. pesticide, fungicide, nematicide) applications, and/or for reducing the environmental impact of chemical applications pesticides and/or for reducing disease incidence in a crop and/or for improving crop yield.

In one other specific embodiment, the method of the invention may also be used as a tool for experimental research, particularly in the field of functional genomics. Targeted down-regulation of pest genes by RNAi can be used in in vitro or in vivo assays in order to study gene function. Assays based on targeted down-regulation of specific pest genes, leading to a measurable phenotype may also form the basis of compound screens for novel pesticides.

H. Compositions and Kits

In a further aspect the invention relates to a composition for reducing pest population growth and/or for killing or paralyzing a pest organism and/or for improving plant resistance to pest organisms, for improving resistance to pest organism, and/or for controlling pest population growth, and/or for preventing or reducing infestation by a pest species and/or for killing or paralyzing a pest organism, for reducing disease incidence in a crop and/or for improving crop yield, said composition comprising at least one RNA delivery molecule as defined herein, and more preferably comprising at least one RNA delivery molecule and/or at least one chimeric RNAi molecule as herein described.

According to one embodiment, the invention relates to a composition comprising at least one RNA delivery molecule as defined herein, and more preferably comprising at least one RNA delivery molecule and/or at least one chimeric RNAi molecule as herein described and a physiological or agronomical acceptable carrier, excipient or diluent. The invention also encompasses the use of said composition as a pesticide for a plant or for propagation or reproductive material of a plant.

According to yet another embodiment, the invention relates to a composition comprising at least one RNA delivery molecule as defined herein, and more preferably comprising at least one RNA delivery molecule and/or at least one chimeric RNAi molecule as herein described, and a physiological agronomical acceptable carrier, excipient or diluent.

The composition may contain further components which serve to stabilise the dsRNA and/or prevent degradation of the dsRNA during prolonged storage of the composition.

The composition may still further contain components which enhance or promote uptake of the RNA delivery molecule and/or the chimeric RNAi molecule by the pest organism. These may include, for example, chemical agents which generally promote the uptake of RNA into cells e.g. lipofectamin etc., and enzymes or chemical agents capable of digesting the fungal cell wall, e.g. a chitinase.

The composition may be in any suitable physical form for application to the pest, to substrates, to cells (e.g. plant cells), or to organism infected by or susceptible to infection by a pest species. In another embodiment, the invention provides a composition comprising:
(a) at least one RNA delivery molecule according to the present invention, and
(b) at least one RNA molecule which comprises double-stranded RNA comprising annealed complementary strands, one of which has a nucleotide sequence which is complementary to at least part of a target nucleotide sequence of a target gene of a pest species, and which further comprises a nucleotide sequence which binds to the RNA-binding domain of the RNA delivery molecule of (a)

provided that the RNA delivery molecule is recognized and may bind to the RNA binding protein or RNA binding domain of the RNA delivery molecule.

The RNA molecule contained in said compositions may be (partially) self-complementary or comprise a sense and antisense strand forming a double stranded portion.

In another embodiment, the invention provides a composition comprising:
at least one RNA delivery molecule according to the present invention, and
at least one chimeric RNAi molecule comprising
at least a double-stranded RNA comprising annealed complementary strands, one of which has a nucleotide sequence which is complementary to at least part of a target nucleotide of a target gene of said pest species (i.e. capable of causing RNAi interference) and
a sequence recognized by an RNA binding protein or RNA binding domain, for instance as represented in any of SEQ ID NOs 15 to 40, or as represented in FIG. 41 or 42.

In yet another embodiment, the present invention relates to a composition comprising:
an RNA delivery molecule as defined herein, and
at least one chimeric RNAi molecule as represented by any of SEQ ID NOs 41 to 52 or any of SEQ ID NOs 54 to 56, or any of SEQ ID NOs 57 to 71, or any of SEQ ID NOs 72 to 86.

In one specific embodiment, the invention relates to a composition, ne specific embodiment, the invention relates to any of the uses as described above, wherein
the RNA-binding domain of the RNA delivery molecule comprises the coliphage HK022 Nun protein or a fragment thereof, said fragment comprising the RNA-binding domain of the HK022 Nun protein, preferably the RNA binding domain is a polypeptide comprising the sequence represented in any of SEQ ID NOs 2, 4, 6, 8 or 87, most preferably comprising the sequence represented in SEQ ID NO 8, and
the RNA molecule which comprises the double stranded RNA molecule and which further comprises a nucleotide sequence corresponding to the binding motif for binding to the coliphage HK022 Nun protein or the fragment thereof, preferably the binding motif represented in SEQ ID NO 15 or 16, or
more preferably the RNA molecule is any of the chimeric RNAi molecules as represented by any of SEQ ID NOs 45 to 48, 55, 61 to 64, 70, 76 to 79 and 85.

In another specific embodiment, the invention relates to a composition, wherein
the RNA-binding domain of the RNA delivery molecule is the *Bacillus subtilis* LicT protein or a fragment thereof, said fragment comprising the RNA binding domain, preferably the RNA binding domain is a polypeptide comprising the sequence represented in any of SEQ ID NO 10 or 12, most preferably comprising the sequence represented in SEQ ID NO 12, and the RNA molecule which comprises the double stranded RNA molecule comprises a nucleotide sequence corresponding to the binding motif for binding to the *Bacillus subtilis* LicT protein or the fragment thereof, preferably the binding motif represented in FIG. 41, or as represented in any of SEQ ID NOs 17 to 34, or more preferably the RNA molecule is any of the chimeric RNAi molecules as represented by any of SEQ ID NOs 41 to 44, 54, 57 to 60, 69, 72 to 75, and 84.

In yet another specific embodiment, the invention relates to a composition, wherein the RNA-binding domain of the RNA delivery molecule is MS2 or a fragment thereof, said fragment comprising the RNA binding domain, and preferably the RNA binding domain is a polypeptide comprising the sequence represented in SEQ ID NO 14, and the RNA molecule which comprises the double stranded RNA molecule comprises a nucleotide sequence corresponding to the binding motif for binding to MS2 or the fragment thereof, and preferably the binding motif represented in FIG. 42, or as represented in any of SEQ ID NOs 35 to 40, or the RNA molecule is any of the chimeric RNAi molecules as represented by any of SEQ ID NOs 49 to 52, 56, 65 to 68, 71, 80 to 83 and 86.

In addition, the present invention also relates to methods for producing an RNA delivery molecule described herein comprising:

(a) introducing into a host cell an isolated DNA molecule encoding any of the RNA delivery molecules of the invention, an nucleic acid encoding any of the RNA delivery molecules of the invention or a vector comprising said nucleic acid;

(b) growing the host cell under conditions suitable for expression of the RNA delivery molecule; and (c) isolating the RNA delivery molecule produced by the host cell.

In a preferred embodiment the present invention relates to a method for producing an RNA delivery molecule, wherein the RNA binding domain of said delivery molecule comprises a polypeptide comprising the coliphage HK022 Nun protein (for instance as represented in SEQ ID NO 2), a homologue thereof, or a fragment thereof comprising the RNA-binding domain, said fragment preferably comprising amino acids 1 to 47 (SEQ ID NO 4) of the aminoterminal sequence, more preferably comprising amino acids 13 to 47 (SEQ ID NO 6) of the aminoterminal sequence, most preferably comprising amino acids 22 to 47 (SEQ ID NO 8) of the aminoterminal sequence of the HK022 Nun protein.

In another preferred embodiment the present invention relates to a method for producing an RNA delivery molecule, wherein the RNA binding domain of said delivery molecule comprises a polypeptide comprising the *Bacillus subtilis* LicT protein (for instance as represented in SEQ ID NO 10), a homologue thereof, or a fragment thereof comprising the RNA-binding domain, said fragment preferably comprising amino acids 1 to 56 (SEQ ID NO 12) of the aminoterminal sequence of the LicT protein.

In yet another preferred embodiment the present invention relates to a method for producing an RNA delivery molecule, wherein the RNA binding domain of said delivery molecule comprises a polypeptide comprising the bacteriophage MS2 coat protein (for instance as represented in SEQ ID NO 14), a homologue thereof, or a fragment thereof comprising the RNA-binding domain.

In addition, the present invention also relates to methods for producing a chimeric RNAi molecule described herein comprising:

introducing into a host cell an isolated DNA molecule encoding any of the chimeric RNAi molecules of the invention;

growing the host cell under conditions suitable for expression of the chimeric RNAi molecule; and isolating the chimeric RNAi molecule produced by the host cell.

In a preferred embodiment the present invention relates to a method for producing a chimeric RNAi molecule wherein the chimeric RNAi molecule comprises:

at least one nucleotide sequence recognized by an RNA-binding protein or RNA-binding domain, for instance as represented in any of SEQ ID NOs 15 to 40, or an RNA secondary structure as represented in FIG. 41 or 42, and at least one nucleotide sequence corresponding to a target nucleotide sequence of a target gene of a pest species.

According to another preferred embodiment, the present invention relates to a method for producing a chimeric RNAi molecule wherein the chimeric RNAi molecule has a sequence as represented any of FIGS. 43 to 54 (any of SEQ ID NOs 41 to 52) or FIGS. 56 to 58 (any of SEQ ID NOs 54 to 56), or any of FIGS. 60 to 74 (any of SEQ ID NOs 57 to 71), or any of FIGS. 76 to 90 (any of SEQ ID NOs 72 to 86).

In addition, the present invention also relates to methods for producing a complex comprising an RNA delivery molecule as defined herein, and at least one chimeric RNAi molecule as defined herein comprising:

introducing into a host cell an isolated nucleic acid encoding any of the RNA delivery molecules of the invention and an a chimeric RNAi molecule as defined herein; provided that the chimeric RNAi molecule comprises a sequence which is specifically recognized and able to be bound by the RNA delivery molecule, growing the host cell under conditions suitable for expression of the RNA delivery molecule and the chimeric RNAi molecule; and isolating the complex of the RNA delivery molecule with the chimeric RNAi molecule produced by the host cell.

In the context of preparing an RNA delivery molecule, a chimeric RNAi molecule or a complex comprising an RNA delivery molecule as defined herein, the term "host cell" may any prokaryotic or eukaryotic cell, such as a bacterial, insect, fungal, plant or animal cell.

In more specific embodiment the invention relates to methods for producing specific complexes as represented in Table 3 or 4.

According to another embodiment, the present invention also relates to a kit comprising at least one RNA delivery molecule as described herein. According to yet another embodiment, the present invention also relates to a kit comprising at least one chimeric RNAi molecule as described herein. According to yet another embodiment, the present invention also relates to a kit comprising a nucleic acid encoding an RNA delivery molecule as described herein. The invention also relates to a kit comprising any vector described herein comprising a nucleic acid encoding any of the RNA delivery molecules and/or any of the corresponding RNAi molecule as described herein. It should be understood that these nucleic acid sequences according to the present invention may be comprised in one or in several separate vectors.

In another preferred embodiment, the invention relates to a kit comprising a composition or a complex as defined herein. Suitable combinations of specific RNA delivery molecule with chimeric RNAi molecule in such compositions or complexes are represented in Tables 5 and 6.

It is further contemplated that the "composition" of the invention may be supplied as a "kit-of-parts" comprising the RNA delivery molecule and the chimeric RNAi molecule in one or in separate containers, and a suitable diluent or carrier for the RNA in a further separate container. The invention also relates to the supply of the RNA delivery molecule and/or the chimeric RNAi molecule alone without any further components. In these embodiments the RNA delivery molecule and/or the chimeric RNAi molecule may be supplied in a concentrated form, such as a concentrated aqueous solution. It may even be supplied in frozen form or in freeze-dried or lyophilized form. The latter may be more stable for long term storage and may be de-frosted and/or reconstituted with a suitable diluent immediately prior to use.

The present invention further relates to the medical use of any of the delivery molecule, chimeric RNAi molecules, constructs, nucleotide sequences, recombinant DNA constructs or compositions thereof described herein.

In one specific embodiment, the composition is a pharmaceutical or veterinary composition for treating or preventing pest infections of humans or animals, respectively. Such compositions will comprise at least one RNA delivery molecule and at least one chimeric RNAi molecule according to the invention, wherein the chimeric RNAi molecule comprises double-stranded RNA comprising annealed complementary strands, one of which has a nucleotide sequence which is complementary to at least part of a target nucleotide sequence of a target gene of a pest species to be down-regulated and at least one carrier, excipient suitable for pharmaceutical use or for veterinary use, respectively.

The composition may be a composition suitable for topical use, such as application on the skin of an animal or human, for example as liquid compositions to be applied to the skin as drops, or by brushing, or a spray, also creams, ointments, etc. for topical application and transdermal patches.

Other conventional pharmaceutical dosage forms may also be produced, including tablets, capsules, pessiaries, suppositories, etc. The chosen form will depend upon the nature of the pest species and hence the nature of the disease it is desired to treat.

Preferred examples of pest species causing infections in human and animal are fungi. Target human pathogenic and animal pathogenic fungi include, but are not limited to the following:

In humans: *Candida* spp., particularly *Candida albicans*; Dermatophytes, including *Epidermophyton* spp., *Trichophyton* spp., and *Microsporum* spp.; *Aspergillus* spp., particularly *Aspergillus flavus, Aspergillus fumigatus, Aspergillus nidulans, Aspergillus niger, Aspergillus terreus* group; *Blastomyces dermatitidis; Coccidioides immitis; Crytococcus neoformans; Histoplasma capsulatlum* Var. *capsulatum* or Var. *duboisii, Sporothrix schenckii Fusarium* spp.; *Scopulariopsis brevicaulis; Fonsecaea* spp.

In animals: *Candida* spp.; *Microsporum* spp., particularly *Microsporum canis, Microsporum gypseum; Trichophyton mentagrophytes; Apergillus* spp.; *Cryptococcus neoformans*.

The composition may be a composition suitable for agronomical use, such as a spray, a coating, a powder and the like. In particular, the present invention provides pesticidal composition developed to be used in agriculture or horticulture.

These pesticidal compositions may be prepared in a manner known per se. For example, the active compounds can be converted into the customary formulations, such as solutions, emulsions, wettable powders, water dispersible granules, suspensions, powders, dusting agents, foaming agents, pastes, soluble powders, granules, suspo-emulsion concentrates, microcapsules fumigants, natural and synthetic materials impregnated with active compound and very fine capsules and polymeric substances.

Furthermore, the pesticidal compositions according to the present invention may comprise a synergist. The RNA delivery molecule and/or chimeric RNAi molecules, constructs, nucleotide sequences, or compositions thereof according to the invention, as such or in their formulations, can also be used in a mixture with known fungicides, bactericides, acaricides, nematicides or insecticides, to widen, for example, the activity spectrum or to prevent the development of resistance. In many cases, this results in synergistic effects, i.e. the activity of the mixture exceeds the activity of the individual components.

Additionally the RNA delivery molecule and/or chimeric RNAi molecules, constructs, nucleotide sequences or compositions thereof according to the invention, as such or in their formulations or above-mentioned mixtures, can also be used in a mixture with other known active compounds, such as herbicides, fertilizers and/or growth regulators.

The present invention also relates to fibrous pesticide composition and its use as pesticide, wherein the fibrous composition comprises a non-woven fiber and an effective amount of at least one of the RNA delivery molecule and/or chimeric RNAi molecules, nucleotide sequences, recombinant DNA constructs or compositions thereof described herein, covalently attached or stably adsorbed to the fiber.

In a further particular embodiment, the fiber is biodegradable and the adsorbed the RNA delivery molecule and/or chimeric RNAi molecules or compositions thereof as described herein, can be slowly released into a localized area of the environment to control pests in that area over a period of time.

The present invention also encompasses solid formulations of slow-release pesticidal composition comprising the molecules or constructs as described herein, and their use as pesticide. The formulations release the RNA delivery molecules and/or the chimeric RNAi molecule as described herein (a) into the environment (soil, aqueous medium, plants) in a controlled and slow fashion (complete release within several days up to a few months).

The present invention also relates to surfactant-diatomaceous earth compositions for pesticidal use in the form of dry spreadable granules comprising at least one RNA delivery molecule and/or at least one chimeric RNAi molecule as described herein. The granules comprises in addition to the diatomaceous earth, a surfactant composition designed to provide binding, rewetting and disintegration properties to the granules. By diatomaceous earth is meant a silica material characterized by a large surface area per unit volume. Diatomaceous earth is a naturally occurring material and consists mainly of accumulated shells or frustules of intricately structured amorphous hydrous silica secreted by diatoms.

The present invention also provides solid, water-insoluble lipospheres and their use as pesticide, wherein said lipospheres are formed of a solid hydrophobic core having a layer of a phospholipid embedded on the surface of the core, containing at least one RNA delivery molecule and/or chimeric RNAi molecule as described herein in the core, in the phospholipid, adhered to the phospholipid, or a combination thereof.

The pesticidal compound containing lipospheres have several advantages including stability, low cost of reagents, ease of manufacture, high dispersibility in an aqueous medium, a release rate for the entrapped compound that is controlled by the phospholipid coating and the carrier.

The invention further relates to pesticidal formulations in the form of microcapsules having a capsule wall made from a urea/dialdehyde precondensate and comprising at least one RNA delivery molecule and/or chimeric RNAi molecule as described herein.

In another specific embodiment, the composition may be a coating that can be applied to a substrate in order to protect said substrate from infestation by a pest species, such as a fungus and/or to prevent, arrest or reduce growth of the pest species on the substrate and thereby prevent damage caused by said pest species. In this embodiment, the composition can be used to protect any substrate or material that is susceptible to infestation by or damage caused by a pest species, for example foodstuffs and other perishable materials, and substrates such as wood. Preferred target pest species for this embodiment is are fungus species, including, but are not limited to, the following: *Stachybotrys* spp.; *Apergillus* spp.; *Alternaria* spp.; *Cladosporium* spp.

In this embodiment the composition will comprise at least one RNA delivery molecule and at least one chimeric RNAi molecule according to the invention, wherein the chimeric RNAi molecule comprises double-stranded RNA comprising annealed complementary strands, one of which has a nucleotide sequence which is complementary to at least part of a target nucleotide sequence of a target gene of the pest species to be down-regulated and optionally at least one carrier, excipient suitable for the intended use.

The nature of the excipients and the physical form of the composition may vary depending upon the nature of the substrate that it is desired to treat. For example, the composition may be a liquid that is brushed or sprayed onto or imprinted into the material or substrate to be treated, or a coating that is applied to the material or substrate to be treated.

The present invention further encompasses a method for treating and/or preventing fungal infestation on a substrate comprising applying an effective amount of any of the compositions described herein to said substrate.

The present invention also relates to methods for treating and/or preventing pest infestation on a substrate comprising applying an effective amount of a RNA delivery molecule and/or a chimeric RNAi molecule, nucleic acid, vector, or a composition thereof as described herein to said substrate.

The present invention also relates to methods for treating and/or preventing pest growth and/or pest infestation of a plant or propagative or reproductive material of a plant comprising applying an effective amount of a RNA delivery molecule and/or a chimeric RNAi molecule, nucleic acid, vector, or a composition thereof as described herein to a plant or to propagation or reproductive material of a plant.

In another embodiment, the invention relates to a method for controlling pest growth on a cell or an organism or for preventing pest infestation of a cell or an organism susceptible to infection to said pest species, comprising contacting said pest species with any of the RNA delivery molecule and/or the chimeric RNAi molecule, nucleic acid, vector, or a composition thereof described herein, whereby the dsRNA is taken up by said pest species and thereby controls growth or prevents infestation.

Bacteria can be engineered to produce any of the dsRNA or dsRNA constructs of the invention. These bacteria can be eaten by the pest species. When taken up, the dsRNA can initiate an RNAi response, leading to the degradation of the target mRNA and weakening or killing of the feeding pest.

Therefore, in a more specific embodiment, said RNA delivery molecule and/or the chimeric RNAi molecule is expressed by a prokaryotic, such as a bacterial, or eukaryotic, such as a yeast, host cell or host organism.

Some bacteria have a very close interaction with the host plant, such as symbiotic *Rhizobium* with the Leguminosea (for example Soy). Such recombinant bacteria could be mixed with the seeds (ie coating) and used as soil improvers. Alternatively, dsRNA producing bacteria can be sprayed directly onto the crops, for instance *Bacillus thuringiensis* species. Possible applications, include intensive greenhouse cultures, for instance crops that are less interesting from a GMO point of view, as well as broader field crops such as soy.

This approach has several advantages, eg: since the problem of possible dicing by a plant host is not present, it allows the delivery of dsRNA into the gut lumen of the feeding pest; the use of bacteria as insecticides does not involve the generation of transgenic crops, especially for certain crops where transgenic variants are difficult to obtain; there is a broad and flexible application in that different crops can be simultaneously treated on the same field and/or different pests can be simultaneously targeted, for instance by combining different bacteria producing distinct dsRNAs.

According to another specific embodiment, the invention encompasses the GMO approaches and thus relates to a method as described above wherein said double stranded RNA is expressed by said cell or organism infested with or susceptible to infestation by said pest species, for instance said cell is a plant cell or said organism is a plant.

The invention further relates to a method for increasing plant yield comprising introducing in a plant any of the RNA delivery molecule and/or chimeric RNAi molecule, nucleic acid, vector or composition thereof in an expressible format.

It should be understood that in the above described compositions and kits of the invention comprising both an RNA delivery molecule and a chimeric RNAi molecule, the sequences of the molecules should be such that the RNA binding protein or RNA-binding domain in the RNA delivery molecule recognizes and binds to the RNA recognition site, specific for the RNA binding protein or RNA-binding domain, in the chimeric RNAi molecule.

The invention will be further understood with reference to the following non-limiting examples.

EXAMPLES

The practice of the present invention will employ, unless otherwise indicated, conventional techniques used in recombinant DNA technology, molecular biology, biological testing, and the like, which are within the skill of the art. Such techniques are explained fully in the literature.

In Example 1, several constructs for RNA delivery molecules are described including possible ways for making them. In Example 2, several constructs for chimeric RNAi molecules are described. It should be clear that the present invention is not limited to the specific constructs exemplified herein.

Example 1

Non-Limiting Examples of RNA Delivery Vehicles According to the Invention

The RNA delivery vehicle consists of a targeting protein such as transferrin of the target species fused to an RNA binding protein such as MS2, Nun or licT. The organization of the RNA delivery vehicles is: HIS-RNA-binding protein/domain-linker-transferrin.

Genbank Accession Numbers:
- Bacteriophage λ Nun protein: P18683, VNBPHK
- *Bacillus subtilis* LicT protein: P39805, S47216, BAA11696, CAA82194
- Bacteriophage MS2 coat protein: P03612, CAA23989, NP_040648, VCBPIM2, 721932A
- Human transferrin protein: P02787, O43890 Q9NQB8 Q9UHV0
- *Drosophila melanogaster* transferrin homolog Tsf1: NM_078677
- *Drosophila melanogaster* transferrin homolog Tsf2: NM_079320
- *Galanthus nivalis* agglutinin: P30617, JE0136, S19735
- Potato Leafroll virus capsid protein: VCVQL2, AAL77965, AAL77957
- Potato Leafroll virus read-through protein: NP_056751, AAN38829, AAL77959

1.1. Full-Length Nun Protein Linked to Transferrin

Step 1: To obtain the Nun gene sequence, PCR is performed with primers pR11 and pR12 on bacteriophage λ DNA and the PCR product is cloned into the TOPO TA Cloning® vector (Invitrogen) and sequence verified.

pR11 is a sense primer starting at the ATG startcodon of the Nun gene; pR12 is an antisense primer starting at the TAA stopcodon of the Nun gene.

Step 2: For cloning the Nun ORF behind the His-tag, PCR is performed with primers pR13 and pR14 on the vector resulting from step 1. The PCR product is digested with NcoI and SpeI, cloned into the pFastBac™ HTa vector (Invitrogen) digested with NcoI and SpeI, and sequence verified.

pR13 is the same primer as pR11 but the ATG startcodon of the Nun gene is preceded by a NcoI restriction site; pR14 is the same primer as pR12 but lacks the TAA stopcodon of the Nun gene; this gene-specific sequence is preceded by the linker encoding sequence and a SpeI site.

Step 3: To obtain the transferrin sequence, PCR is performed with primers pE11 and pE12 on a human cDNA library and the PCR product is cloned into the TOPO TA Cloning® vector and sequence verified.

pE11 is a sense primer starting at the ATG startcodon of the transferrin gene; pE12 is an antisense primer starting at the TAA stopcodon of the transferrin gene.

Step 4: To make the Nun-transferrin fusion gene, PCR is performed with primers pE13 and pE14 on the vector resulting from step 3. The PCR product is digested with SpeI and XbaI, cloned into the vector resulting from step 2 digested with SpeI and XbaI, and sequence verified.

pE13 is the same primer as pE11 but the ATG startcodon of the transferrin gene is preceded by a SpeI restriction site; pE14 is the same primer as pE12 but the TAA stopcodon of the transferrin gene is preceded by an XbaI restriction site.

1.2. N-Terminal 47 Amino Acids of Nun Protein Linked to Transferrin

To obtain this fusion construct the same cloning steps are performed as in Example 1.1, but in Step 2 PCR primer pR14 is replaced by PCR primer pR18.

pPR18 is an antisense primer starting at codon 47 (nucleotides 139-141) instead of at the TAA stopcodon; again, this gene-specific sequence is preceded by the linker encoding sequence and a SpeI site.

1.3. Amino Acids 13-47 of Nun Protein Linked to Transferrin

To obtain this fusion construct the same cloning steps are performed as in Example 1.1, but in Step 2 PCR primer pR13 is replaced by PCR primer pR15 and pR14 is replaced by PCR primer pR18.

pR15 is a sense primer starting at nucleotide 37 (codon 13) of the Nun gene; this gene-specific sequence is preceded by a NcoI restriction site; pR18 is the same as in Example 1.2.

1.4. Amino Acids 22-47 of Nun Protein Linked to Transferrin

To obtain this fusion construct the same cloning steps are performed as in Example 1.1, but in Step 2 PCR primer pR13 is replaced by PCR primer pR17 and pR14 is replaced by PCR primer pR18.

pR17 is a sense primer starting at nucleotide 64 (codon 22) of the Nun gene; this gene-specific sequence is preceded by a NcoI restriction site; pR18 is the same as in Example 1.2.

1.5. *Drosophila Melanogaster* Transferrin

*Drosophila melanogaster* contains two transferrin homologs, Tsf1 and Tsf2. Both *Drosophila melanogaster* transferrin homologs are fused to the full-length Nun protein or to either of the Nun dsRNA-binding domain fragments following the same strategies as in Examples 2.1 through 2.4, but replacing the human transferrin-specific sequence of the primers pE11 through pE14 with *Drosophila melanogaster* transferrin-specific sequence.

1.6. Full-Length LicT Protein Linked to Transferrin

Step 1: To obtain the LicT gene sequence, PCR is performed with primers pR21 and pR22 on *Bacillus subtilis* DNA and the PCR product is cloned into the TOPO TA Cloning® vector and sequence verified.

pR21 is a sense primer starting at the ATG startcodon of the LicT gene; pR22 is an antisense primer starting at the TAA stopcodon of the LicT gene.

Step 2: For cloning the LicT ORF behind the His-tag, PCR is performed with primers pR23 and pR24 on the vector resulting from step 1. The PCR product is digested with BspHI and SpeI, cloned into the pFastBac™HTa vector digested with NcoI and SpeI, and sequence verified.

pR23 is the same primer as pR21 but the ATG startcodon of the LicT gene is preceded by a BspHI restriction site; pR24 is the same primer as pR22 but lacks the TAA stopcodon of the LicT gene; this gene-specific sequence is preceded by the linker encoding sequence and a SpeI site.

Step 3 and Step 4 are identical to Step 3 and Step 4 of Example 1.1.

1.7. N-terminal 56 amino acids of LicT Protein Linked to Transferrin

To obtain this fusion construct the same cloning steps are performed as in Example 1.6, but in Step 2 PCR primer pR24 is replaced by PCR primer pR26.

pR26 is an antisense primer starting at codon 56 (nucleotides 166-168) instead of at the TAA stopcodon; again, this gene-specific sequence is preceded by the linker encoding sequence and a SpeI site.

1.8. *Drosophila melanogaster* Transferrin

*Drosophila melanogaster* contains two transferrin homologs, Tsf1 and Tsf2. Both *Drosophila melanogaster* transferrin homologs are fused to the full-length LicT protein or to its N-terminal dsRNA-binding domain following the same strategies as in Examples 1.6 and 1.7, but replacing the human transferrin-specific sequence of the primers pE11 through pE14 with *Drosophila melanogaster* transferrin-specific sequence.

1.9 Full-Length MS2 Protein Linked to Human Transferrin

Step 1: To obtain the MS2 gene sequence, PCR is performed with primers pR31 and pR32 on bacteriophage MS2 DNA and the PCR product is cloned into the TOPO TA Cloning® vector and sequence verified.

pR31 is a sense primer starting at the ATG startcodon of the MS2 coat protein gene; pR32 is an antisense primer starting at the TAA stopcodon of the MS2 coat protein gene.

Step 2: For cloning the MS2 coat protein ORF behind the His-tag, PCR is performed with primers pR33 and pR34 on the vector resulting from step 1. The PCR product is digested with NcoI and SpeI, cloned into the pFastBac™HTa vector digested with NcoI and SpeI, and sequence verified.

pR33 is the same primer as pR31 but the ATG startcodon of the MS2 coat protein gene is made part of a NcoI restriction site; pR34 is the same primer as pR32 but lacks the TAA stopcodon of the MS2 coat protein gene; this gene-specific sequence is preceded by the linker encoding sequence and a SpeI site.

Step 3 and Step 4 are identical to Step 3 and Step 4 of Example 1.1.

1.10. *Drosophila melanogaster* Transferrin

*Drosophila melanogaster* contains two transferrin homologs Tsf1 and Tsf2. Both *Drosophila melanogaster* transferrin homologs are fused to the MS2 coat protein following the same strategies as in Example 1.9, but replacing the human transferrin-specific sequence of the primers pE11 through pE14 with *Drosophila melanogaster* transferrin-specific sequence.

1.11. Full-Length Nun Protein Linked to *Galanthus nivalis* Agglutinin

Step 1 and Step 2 are identical to Step 1 and Step 2 of Example 1.1.

Step 3: To obtain the *Galanthus nivalis* agglutinin sequence, PCR is performed with primers pE21 and pE22 on a *Galanthus nivalis* (Common Snowdrop) cDNA library and the PCR product is cloned into the TOPO TA Cloning® vector and sequence verified.

pE21 is a sense primer starting at the ATG startcodon of the *Galanthus nivalis* agglutinin gene; pE22 is an antisense primer starting at the TAA stopcodon of the *Galanthus nivalis* agglutinin gene.

Step 4: To make the Nun—*Galanthus nivalis* agglutinin fusion gene, PCR is performed with primers pE23 and pE24 on the vector resulting from step 3. The PCR product is digested with SpeI and XbaI, cloned into the vector resulting from step 2 digested with SpeI and XbaI, and sequence verified.

pE23 is the same primer as pE21 but the ATG startcodon of the *Galanthus nivalis* agglutinin gene is preceded by a SpeI restriction site; pE24 is the same primer as pE22 but the TAA stopcodon of the *Galanthus nivalis* agglutinin gene is preceded by an XbaI restriction site.

1.12. N-terminal 47 Amino Acids of Nun Protein Linked to *Galanthus nivalis* Agglutinin To obtain this fusion construct the same cloning steps are performed as in Example 1.11, but in Step 2 PCR primer pR14 is replaced by PCR primer pR18.

pR18 is the same as in Example 1.2.

1.13. Amino acids 13-47 of Nun Protein Linked to *Galanthus Nivalis* Agglutinin

To obtain this fusion construct the same cloning steps are performed as in Example 1.11, but in Step 2 PCR primer pR13 is replaced by PCR primer pR15 and pR14 is replaced by PCR primer pR18.

pR15 is the same as in Example 1.3.; pR18 is the same as in Example 1.2.

1.14. Amino acids 22-47 of Nun Protein Linked to *Galanthus nivalis* Agglutinin

To obtain this fusion construct the same cloning steps are performed as in Example 1.11, but in Step 2 PCR primes pR13 is replaced by PCR primer pR17 and pR14 is replaced by PCR primer pR18.

pR17 is the same as in Example 1.4.; pR18 is the same as in Example 1.2.

1.15. Full-Length LicT Protein Linked to *Galanthus Nivalis* Agglutinin

Step 1 and Step 2 are identical to Step 1 and Step 2 of Example 1.6.

Step 3 and Step 4 are identical to Step 3 and Step 4 of Example 1.11.

1.16. N-terminal 56 Amino Acids of LicT Protein Linked to *Galanthus Nivalis* Agglutinin To obtain this fusion construct the same cloning steps are performed as in Example 1.15, but in Step 2 PCR primer pR24 is replaced by PCR primer pR26.

pR26 is the same as in Example 1.7.

1.17 Full-Length MS2 Protein Linked to Human *Galanthus Nivalis* Agglutinin

Step 1 and Step 2 are identical to Step 1 and Step 2 of Example 1.9.

Step 3 and Step 4 are identical to Step 3 and Step 4 of Example 1.11.

1.18. Full-Length Nun Protein Linked to Potato Leafroll Virus Capsid Protein

Step 1 and Step 2 are identical to Step 1 and Step 2 of Example 1.1.

Step 3: To obtain the Potato Leafroll virus capsid protein genomic sequence, PCR is performed with primers pE31 and pE32 on Potato Leafroll virus cDNA and the PCR product is cloned into the TOPO TA Cloning® vector and sequence verified.

pE31 is a sense primer starting at the ATG startcodon of the Potato Leafroll virus capsid protein gene; pE32 is an antisense primer starting at the TAA stopcodon of Potato Leafroll virus capsid protein gene.

Step 4: To make the Nun-Potato Leafroll virus capsid protein fusion gene, PCR is performed with primers pE33 and pE34 on the vector resulting from step 3. The PCR product is digested with SpeI and XbaI, cloned into the vector resulting from step 2 digested with SpeI and XbaI, and sequence verified.

pE33 is the same primer as pE31 but the ATG startcodon of the Potato Leafroll virus capsid protein gene is preceded by a SpeI restriction site; pE34 is the same primer as pE32 but the TAA stopcodon of the Potato Leafroll virus capsid protein gene is preceded by an XbaI restriction site.

1.19. N-Terminal 47 Amino Acids of Nun Protein Linked to Potato Leafroll Virus Capsid Protein To obtain this fusion construct the same cloning steps are performed as in Example 1.18, but in Step 2 PCR primer pR14 is replaced by PCR primer pR18.

pR18 is the same as in Example 1.2.

1.20. Amino Acids 13-47 Amino Acids of Nun Protein Linked to Potato Leafroll Virus Capsid Protein To obtain this fusion construct the same cloning steps are performed as in Example 1.18, but in Step 2 PCR primer pR13 is replaced by PCR primer pR15 and pR14 is replaced by PCR primer pR18.

1.21. Amino acids 22-47 Amino Acids of Nun Protein Linked to Potato Leafroll Virus Capsid Protein To obtain this fusion construct the same cloning steps are performed as in Example 1.18, but in Step 2 PCR primer pR13 is replaced by PCR primer pR17 and pR14 is replaced by PCR primer pR18.

pR15 is the same as in Example 1.3.; pR18 is the same as in Example 1.2.

1.22 Potato Leafroll Virus Read-Through Protein

Potato Leafroll virus read-through protein is fused to the full-length Nun protein or to either of the Nun dsRNA-binding domain fragments following the same strategies as in Examples 1.18 through 1.21, but in Step 3 PCR primer pE32 is replaced by PCR primer pE36 and in Step 4 PCR primer pE34 is replaced by PCR primer pE38.

pE36 is an antisense primer starting at the TAA stopcodon of Potato Leafroll virus read-through protein gene; pE38 is the same primer as pE36 but the TAA stopcodon of the Potato Leafroll virus read-through protein gene is preceded by an XbaI restriction site.

1.23. Full-Length LicT Protein Linked to Potato Leafroll Virus Capsid Protein

Step 1 and Step 2 are identical to Step 1 and Step 2 of Example 1.6

Step 3 and Step 4 are identical to Step 3 and Step 4 of Example 1.18.

1.24. N-terminal 56 Amino Acids of LicT Protein Linked to Potato Leafroll Virus Capsid Protein To obtain this fusion construct the same cloning steps are performed as in Example 1.23, but in Step 2 PCR primer pR24 is replaced by PCR primer pR26.

pR26 is the same as in Example 1.7.

1.25 Potato Leafroll Virus Read-Through Protein

Potato Leafroll virus read-through protein is fused to the full-length LicT protein or to its N-terminal dsRNA-binding domain following the same strategies as in Examples 1.23 and 1.24, but in Step 3 PCR primer pE32 is replaced by PCR primer pE36 and in Step 4 PCR primer pE34 is replaced by PCR primer pE38.

pR36 and pR38 are the same as in Example 1.22

1.26 Full-Length MS2 Protein Linked to Potato Leafroll Virus Capsid Protein

Step 1 and Step 2 are identical to Step 1 and Step 2 of Example 1.9.

Step 3 and Step 4 are identical to Step 3 and Step 4 of Example 1.18.

1.27 Full-Length MS2 Protein Linked to Potato Leafroll Virus Read-Through Protein Potato Leafroll virus read-through protein is fused to the full-length MS2 protein following the same strategies as in Example 2.26, but in Step 3 PCR primer pE32 is replaced by PCR primer pE36 and in Step 4 PCR primer pE34 is replaced by PCR primer pE38.

pR36 and pR38 are the same as in Example 1.22.

Example 2

Non-Limiting Examples for the Construction of Chimeric RNAi Molecules that Recognize RNA Delivery Molecules According to the Invention The chimeric RNAi molecule is principally a hairpin construct that contains at least one target RNA sequence and, in the loop(s) or at the 3' or 5' end, at least one recognition sequence for an RNA-binding protein, such as for instance MS2, Nun or licT.

Target genes from the target species are cloned accordingly. Examples of target genes in *C. elegans* include β-tubulin (Genbank accession NM_066966), sup-35 (Genbank accession number X73845) unc-22 (Genbank accession Z73899) and 60S ribosomal protein L9 (Genbank accession NM_066259), see Table 7. The length of the tested target RNA sequence is 80-450 base pairs.

TABLE 7

Overview of the examples: different genes in four different plant pest species, *Caenorhabditis elegans*, *Nilaparvata lugens*, *Diabrotica virgifera*, *Meloidogyne incognita*, and *Magnaporthe grisea*.

| | *C. elegans* | *M. incognita* | *Nilaparvata lugens* *Diabrotica virgifera* | *M. grisae* |
|---|---|---|---|---|
| Target gene | β-tubulin rpl-9, sup-35, unc-22 | β-tubulin rpl-9 | β-tubulin rpl-9 | β-tubulin rpl-9 |
| In vitro uptake | Drinking assay | Drinking assay | Bio Assay | Soaking |
| In planta | X | Hairy root assay, whole plant | Whole plant | Hairy root, whole plant |

Promoters useful for the expression of dsRNA are a promoter from an RNA PoII, an RNA PoIII, an RNA PoIIII, T7 RNA polymerase or SP6 RNA polymerase.

Several non-limiting constructs of chimeric RNAi molecules according to the invention are exemplified in FIGS. 43 to 54, FIGS. 56 to 58, FIGS. 60 to 74 and FIGS. 76 to 90. The chimeric RNAi molecules consist of a least two modules: at least one dsRNA sequence against the pest target gene, and (at least one) sequence recognized by the Lict, Nun or MS2 protein or RNA binding domain thereof. The target sequence can be any species-specific sequence that induces lethality or any other severe phenotype in the target species. The RNA binding protein recognition sequence is recognized by the RNA binding protein, such as LicT, Nun or MS2. In case of two recognition sequences in the molecule, these can be recognized by the same RNA binding protein, or by two different RNA binding proteins. In the examples of FIGS. 43 to 54, 60 to 71 and 76 to 87, each of these constructs comprises at least one recognition site for an RNA-binding domain and a species-specific target sequence for down-regulation of tubulin (see FIG. 55, 59 or 75). In the examples of FIGS. 56 to 58, 72 to 74 and 88 to 90 each of these constructs comprises at least cone recognition site for an RNA-binding domain and a species-specific target sequence for down-regulation of unc-22 (see FIG. 55).

Example 3

Non-Limiting Examples of *C. Elegans* Assays to Measure the Efficiency of dsRNA Delivery to Target Cells Using the Constructs According to the Invention In the following example, several assays are described which are used to follow efficacy of RNAi in pest species.

A) Preparation of RNA Vehicle Complex (RVC)

The RNA vehicle complex principally consists of an RNAi mediating molecule (dsRNA or hairpin as described in example 2) to induce RNAi in the target organism and an RNA delivery vehicle (as described in example 1) to increase the efficiency of endo- and/or transcytosis RNA Delivery Vehicle Production and Purification of the RNA Delivery Vehicle in the Baculovirus Expression System:

RNA delivery vehicles, as described in Example 1, are produced in insect Sf9 cells after transfection with recombinant baculoviruses using the Bac-to-Bac® Baculovirus Expression System (Invitrogen). The His-tagged RNA delivery vehicles are protein purified over a HiTrap™ Chelating HP nickel column (Amersham Boisciences). The His-tag is removed by cleavage with recombinant TEV protease (Invitrogen). Protein purification with nickel-chelating resin and rTEV cleavage are also used when RNA delivery vehicle protein is obtained after expression in bacteria or the yeast *Pichia Pastoris*.

RNAi Mediating Molecule Expression and Purification Using Bacteria Expression System The RNAi mediating molecule is obtained using T7 polymerase transcription of the template DNA following the provided protocol of RNA dsRNA kit manufacturers (e.g. T7 RiboMAX™ Express RNAi System, Promega or obtained by Megascript RNAi™ kit, Ambion)

B) Administration of RNA Vehicle Complex (RVC) to *C. elegans*

The RVC complex can be delivered to the *C. elegans* gut by feeding on agar plates, soaking in liquid medium or injection into the gut lumen.

RVC Delivery into *C. elegans* by Soaking and Injection

RNAi is induced by injection of dsRNA into *C. elegans* or by feeding *C. elegans* a solution with dsRNA, called soaking (Gonczy P, Echeverri C, Oegema K, Coulson A, Jones S J, Copley R R, Duperon J, Oegema J, Brehm M, Cassin E, Hannak E, Kirkham M, Pichler S, Flohrs K, Goessen A, Leidel S, Alleaume A M, Martin C, Ozlu N, Bork P, Hyman A A. Nature. 2000 408 page 331-6; Maeda I, Kohara Y, Yamamoto M, Sugimoto A. Curr Biol. 2001 11 page 171-6). These methods can also be used to induce RNAi by feeding with RVC. The RVC complex is prepared by mixing the RNA vehicle protein and the RNA construct in physiological buffer. This solution is either injected into the gut lumen of *C. elegans* or *C. elegans* is soaked in a solution containing the RVC complex In the latter case, the *C. elegans* would drink the RVC in the solution and consequently ingest it into the gut. A variation of this theme is to add the RVC solution on top of *E. coli* seeded agar plates on which *C. elegans* can feed.

RVC Delivery by Feeding

RNAi by feeding is induced in *C. elegans* by feeding with *E. coli*, which expresses dsRNA against the target gene (Fraser A G, Kamath R S, Zipperlen P, Martinez-Campos M, Sohrmann M, Ahringer J. Nature. 2000 408 page 325-30). Similarly, *E. coli* is co-transformed with a vector expressing the chimeric RNAi molecule against the target gene and a vector expressing the RNA delivery vehicle. *C. elegans* feeds on these *E. coli* and ingests RNA and protein to form the RVC. Upon digestion of *E. coli*, the RVC is released into the gut lumen.

All three delivery methods provide the RVC complex to the apical gut surface. The vehicle binds to apical surface proteins that mediate receptor-mediated endocytosis or are endocytosed specifically. This binding greatly enhances absorption into the gut C) Measurement of Improved RNAi Effectiveness in *C. elegans*

The effectiveness of the RVC to induce RNAi is measured using a specific and visible movement phenotype, "twitcher". Down-regulation by RNAi or mutations in the *C. elegans* gene unc-22, which encodes Twitchin, causes convulsive muscle contractions called "twichter" phenotype (Benian G M et al. 1989. *Sequence of an unusually large protein implicated in regulation of myosin activity in C. elegans*. Nature 342: 45-50). In this experiment the following test reagents are used:

1) Standard dsRNA (RNA without vehicle) against unc-22
2) RVC consisting of e.g., transferrin (see Example 1, 1.1 and 1.9) and RNA against unc-22 (see Example 2, 2.1)

RVC and standard dsRNA are administered to *C. elegans* for example by soaking (as described under A). Different concentrations of RVC and standard dsRNA are tested in 24 or 96-well plates. Ten to fifty L1 larvae are placed into each well and grown for several days until adulthood at 25° C., whereby sufficient food (*E. coli*) is supplied. Adults are examined for the presence of the "twitcher" phenotype using a dissection microscope. Depending on the efficiency of RNAi against unc-22 a certain fraction of animals of a population will exhibit the "twitcher" phenotype. The fraction of animals exhibiting the twitcher phenotype increases with increasing concentration of dsRNA in a dose-dependent manner. If the RVC complex increases delivery of effective RNAi mediating molecules by enhanced endo/transcytosis, the fraction of animals with "twitcher" phenotype is greater at a given concentration (concentration of the RNA molecules is identical) compared to standard dsRNA. As a result, the dose-response curve obtained with RVC is shifted to lower concentrations. The extent of the shift is a means to measure changed efficiency of the RVC. Similarly, the same protocol can be used to test essential genes such as β-tubulin, which cause growth delay and death.

Example 4

Non-Limiting Examples of an Insect Bio Assay to Measure the Efficiency of dsRNA Delivery to Target Cells Using the Constructs According to the Invention The effectiveness of the RVC (RNA vehicle complex) to induce RNAi in the target pest such as corn root worm or planthopper is measured by its potential to increase insect mortality. The selected pest gene is an essential gene and it has been demonstrated that knock down by RNAi causes impaired viability or lethality. In this experiment the following test reagents are used:

1) Standard dsRNA (RNA without vehicle) against pest gene
2) RVC consisting of e.g., transferrin (see Example 1, 1.5 and 1.10) and RNA (see example 2, 2.x) against pest gene.

RVC and standard dsRNA are applied to the surface of casein and wheat germ modified artificial diet for corn rootworm (Marrone, P. G., F. D. Ferri, T. R. Mosley, and L. J.

Meinke. 1985. J. Econ. Entomol. 78:290-293). Different concentrations of RVC and standard dsRNA are tested in 48 or 96-well plates. Each well is infested with one to six neonate corn root worms (respectively 50 to 100 animals per condition) and grown for 4 to 12 days at 25° C. and ~50% relative humidity. Similar for planthopper: Infestation with third-instar nymphs or adults in 24 or 48-well plates, which are grown at 25° C. and 60% relative humidity under long-day (16 L/8 D) conditions (Ito M, Okui H, Nakagawa H, Mio S, Kinoshita A, Obayashi T, Miura T, Nagai J, Yokoi S, Ichinose R, Tanaka K, Kodama S, Iwasaki T, Miyake T. Takashio M, Iwabuchi J. (2002). Biosci Biotechnol Biochem. 2002. 66:240-614) Plates are examined for larval and adult mortality using a dissection microscope. Increasing concentration of dsRNA or RVC increases mortality in a dose-dependent manner. If the RVC complex increases the number of RNAi mediating molecules by enhanced endo/transcytosis, the mortality is greater compared to standard dsRNA at a given concentration. As a result, the dose-response curve obtained with RVC is shifted to lower concentrations respectively the $LD_{50}$ is reduced ($LD_{50}$ is defined as the concentration that caused 50% mortality of the test population).

Example 5

Non-Limiting Examples Assay to Monitor dsRNA Delivery to Target Cells Using Labeled Constructs According to the Invention Endo/transcytosis is monitored using labeled RNA and labeled vehicles. In this experiment the following test reagents are used:
A Labeled vehicle
B Labeled RNAi
C Co-labeled RVC
Reagents are applied to *C. elegans* animals and the uptake from gut lumen (apical) into the gut cell, across the gut cell into the pseudocoelom (basolateral) is monitored. Fluorecence technology might apply using FITC labeled vehicle and Cy3 labeled-Uracil incorporated into the RNA molecule. Given the potential processing during endo/transcytosis and the potential dilution of RNA molecules in the liquid of the pseudocoelom, radioactive labeling using for example $S^{35}$ is preferred.
Results.
The vehicle may accumulate on the apical surface, in the gut cell and potentially at the basolateral surface (in case the vehicle was transcytosed). Similarly, labeled RNA may be visible on the gut cell surface/in the gut cells. It is expected that the RNA delivered via the RVC complex is accumulated significantly higher on/in the gut than plein RNA proving the concept of improved endo/transcytosis via RVC.
Stability of the dsRNA Constructs of the Present Invention in Plant Cells
The stability of the expressed constructs are analyzed with quantitative real-time PCR to determine the quantity of the expressed construct of the invention present in the transgenic plant cell relative to the quantities present in control transgenic plants, expressing a control dsRNA construct. The method to monitor PCR in real-time is described previously and is based on Taqman probes or intercalating dyes (SYBR green). The expressed dsRNA constructs are quantified relative towards a standard dilution series of the template. The results are normalized by using the quantitative PCR data of a set of housekeeping genes from the same samples (Vandesompele et al., Genome Biology 2002, 3:research 0034.1-0034.11).

Example 6

Non-Limiting Examples of an Insect in Planta Assay to Measure the Efficiency of dsRNA Delivery to Target Cells Using the Constructs According to the Invention Plant transformation always requires co-transformation of the plant with a construct containing the RNA delivery vehicle and a construct containing the RNA mediating molecule. The constructs of the present invention are cloned behind the CaMV35S promoter, a root or leave specific promoter or a feeding site specific promoter in a binary vector suitable for plant transformation. The binary vectors are transferred to *Agrobacterium rhizogenes* by three-parental mating (e.g. by *E. coli* HB101 containing pRK2013 helper plasmid). The binary vectors are transferred from *E. coli* into *Agrobacterium tumifaciens*. Subsequently crops plants (such as tomato, soybean, cotton or Tobacco) are co-transformed with the constructs (one containing the RNA delivery vehicle and one containing the RNA mediating molecule) via *Agrobacterium*-mediated transformation. As a control, *Agrobacterium* without binary vector is used. (Example of a protocol for corn transformation: Frame B R, Shou H, Chikwamba R K, Zhang Z, Xiang C, Fonger T M, Pegg S E, Li B, Nettleton D S, Pei D, Wang K. (2002) *Agrobacterium tumefaciens*-mediated transformation of maize embryos using a standard binary vector system. Plant Physiol. 129 page 13-22.). (Example of a protocol for rice transformation: Breitler J C, Meynard D, Van Boxtel J, Royer M, Bonnot F, Cambillau L, Guiderdoni E. (2004). A novel two T-DNA binary vector allows efficient generation of marker-free transgenic plants in three elite cultivars of rice (*Oryza sativa* L.). Transgenic Res 13:271-87).
A) Corn Rootworm
Plant tissues are transformed with the constructs of the present invention and then regenerated into whole plants. Whole-transgenic plants are infested with corn rootworm eggs. Three parameters are scored: (1) Insect mortality, by which after various time points insects are collected and examined for stage of development and mortality compared to non-transformed plants and insecticide treated plants. (2) Plant-resistance, by which the quality of the roots are examined with a rating system such as nodes destroyed, roots pruned or undamaged roots. (3) Plant health, by which plant growth and root density of transformed versus non-transformed versus nematicide treated plants are compared. (A protocol describing the steps from shot gun mediated corn transformation to corn root worm resistance measurement can be found in Moellenbeck D J, Peters M L, Bing J W, Rouse J R, Higgins L S, Sims L, Nevshemal T, Marshall L, Ellis R T, Bystrak P G, Lang B A, Stewart J L, Kouba K, Sondag V, Gustafson V, Nour K, Xu D, Swenson J, Zhang J, Czapla T, Schwab G, Jayne S, Stockhoff B A, Narva K, Schnepf H E, Stelman S J, Poutre C, Koziel M, Duck N. (2001). Insecticidal proteins from *Bacillus thuringiensis* protect corn from corn rootworms. Nat. Biotechnol. 19 page 668-72.)
B) Planthopper
Plants (or plant) tissues are transformed with the constructs of the present invention and then regenerated into whole plants. Whole-transgenic plants are infested with plant hopper neonates, third instar nymphs or adults. Three parameters are scored: (1) Insect mortality, by which after various time points insects are collected and examined for stage of development and mortality compared to non-transformed plants and insecticide treated plants. (2) Plant-resistance, by which the quality of the rice stem and rice leaves are examined with a rating system such as rice stem/leaves have severe feeding damage, rice stem/leaves have limited feeding damage or undamaged steem/leaves. (3) Plant health, by which plant growth, steem length and leaf quality of transformed versus non-transformed versus nematicide treated plants are compared (a protocol describing the steps from rice transformation to plant hopper bio assay can be found in (Nayak P, Basu D, Das S, Basu A, Ghosh D, Ramakrishnan N A, Ghosh M, Sen S K. (1997). Proc Natl Acad Sci USA. 94:2111-6).

SEQUENCE LISTING

```
<160> NUMBER OF SEQ ID NOS: 90

<210> SEQ ID NO 1
<211> LENGTH: 339
<212> TYPE: DNA
<213> ORGANISM: Coliphage HK022

<400> SEQUENCE: 1
atgcttatgg tgaaaaagac tatttatgtt aatcctgaca gcggacaaaa cagaaaagta      60
tctgatagag gtcttacatc tcgagacagg aggagaatag cgagatggga aaaaggata     120 gcatatgcat taaaaaacgg tgtgacacct ggatttaatg ctatagatga cggtcctgaa     180
tataagatta atgaagaccc aatggacaaa gttgacaaag cattagcaac accatttcct     240
cgcgatgtcg aaaaaattga agatgaaaaa tatgaggatg taatgcacag agttgttaat     300
cacgctcacc agcgaaaccc aaacaaaaag tggtcataa                            339

<210> SEQ ID NO 2
<211> LENGTH: 112
<212> TYPE: PRT
<213> ORGANISM: Coliphage HK022

<400> SEQUENCE: 2

Met Leu Met Val Lys Lys Thr Ile Tyr Val Asn Pro Asp Ser Gly Gln
1               5                   10                  15

Asn Arg Lys Val Ser Asp Arg Gly Leu Thr Ser Arg Asp Arg Arg
            20                  25                  30

Ile Ala Arg Trp Glu Lys Arg Ile Ala Tyr Ala Leu Lys Asn Gly Val
        35                  40                  45

Thr Pro Gly Phe Asn Ala Ile Asp Asp Gly Pro Glu Tyr Lys Ile Asn
    50                  55                  60

Glu Asp Pro Met Asp Lys Val Asp Lys Ala Leu Ala Thr Pro Phe Pro
65                  70                  75                  80

Arg Asp Val Glu Lys Ile Glu Asp Glu Lys Tyr Glu Asp Val Met His
                85                  90                  95

Arg Val Val Asn His Ala His Gln Arg Asn Pro Asn Lys Lys Trp Ser
            100                 105                 110

<210> SEQ ID NO 3
<211> LENGTH: 141
<212> TYPE: DNA
<213> ORGANISM: Coliphage HK022

<400> SEQUENCE: 3
atgcttatgg tgaaaaagac tatttatgtt aatcctgaca gcggacaaaa cagaaaagta      60
tctgatagag gtcttacatc tcgagacagg aggagaatag cgagatggga aaaaggata     120 gcatatgcat taaaaaacgg t                                              141

<210> SEQ ID NO 4
<211> LENGTH: 47
<212> TYPE: PRT
<213> ORGANISM: Coliphage HK022
```

```
<400> SEQUENCE: 4

Met Leu Met Val Lys Lys Thr Ile Tyr Val Asn Pro Asp Ser Gly Gln
1               5                   10                  15

Asn Arg Lys Val Ser Asp Arg Gly Leu Thr Ser Arg Asp Arg Arg
            20                  25                  30

Ile Ala Arg Trp Glu Lys Arg Ile Ala Tyr Ala Leu Lys Asn Gly
        35                  40                  45

<210> SEQ ID NO 5
<211> LENGTH: 105
<212> TYPE: DNA
<213> ORGANISM: Coliphage HK022

<400> SEQUENCE: 5
gacagcggac aaaacagaaa agtatctgat agaggtctta catctcgaga caggaggaga      60
atagcgagat gggaaaaaag gatagcatat gcattaaaaa acggt                    105

<210> SEQ ID NO 6
<211> LENGTH: 35
<212> TYPE: PRT
<213> ORGANISM: Coliphage HK022

<400> SEQUENCE: 6

Asp Ser Gly Gln Asn Arg Lys Val Ser Asp Arg Gly Leu Thr Ser Arg
1               5                   10                  15

Asp Arg Arg Arg Ile Ala Arg Trp Glu Lys Arg Ile Ala Tyr Ala Leu
            20                  25                  30

Lys Asn Gly
        35

<210> SEQ ID NO 7
<211> LENGTH: 78
<212> TYPE: DNA
<213> ORGANISM: Coliphage HK022

<400> SEQUENCE: 7
gatagaggtc ttacatctcg agacaggagg agaatagcga gatgggaaaa aaggatagca      60
tatgcattaa aaaacggt                                                   78

<210> SEQ ID NO 8
<211> LENGTH: 26
<212> TYPE: PRT
<213> ORGANISM: Coliphage HK022

<400> SEQUENCE: 8

Asp Arg Gly Leu Thr Ser Arg Asp Arg Arg Ile Ala Arg Trp Glu
1               5                   10                  15

Lys Arg Ile Ala Tyr Ala Leu Lys Asn Gly
            20                  25

<210> SEQ ID NO 9
<211> LENGTH: 834
<212> TYPE: DNA
<213> ORGANISM: Bacillus subtilis

<400> SEQUENCE: 9
atgaaaattg cgaaggtgat caacaataat gtgatcagcg tggtcaatga acaggggaaa      60
gaattggtcg tcatgggcag ggggctcgcg tttcagaaaa agtccggcga tgatgtcgat     120
gaagcccgca ttgagaaagt gttcacgctc gataacaagg atgtatcaga aaagttcaaa     180
```

```
acccttttgt atgatatacc gatcgagtgt atggaagtat ccgaagagat tatcagctac    240
gcaaaattac agctcggcaa aaagctcaac gacagcatct atgtgtcgct gaccgaccat    300
attaactttg ccatccagcg caaccagaaa gggcttgata tcaaaaacgc cttgctgtgg    360
gaaacaaaac ggctctacaa agacgaattt gcgatcggca agaagcgtt  ggttatggta    420 aaaaacaaga ctggtgtgtc tctgccagag gatgaagcag gctttattgc tctgcatatt    480
gtaaatgccg agctgaatga agagatgccc aatattatca acattacaaa agtcatgcaa    540
gagattttga gtattgtaaa ataccatttt aagattgaat caacgaaga  atcgcttcac    600 tattatcggt tcgtcaccca cttaaagttt ttcgcgcagc gtctatttaa cggcactcac    660
atggaaagcc aagacgattt tttgctggat acagtgaaag aaaagtatca tcgcgcgtat    720
gaatgcacga gaaaaatcca aacctacatt gagcgggagt atgagcacaa gctcacaagt    780
gacgagctgc tgtatttaac cattcacata gaaagggtag ttaaacaagc ataa         834
```

```
<210> SEQ ID NO 10
<211> LENGTH: 277
<212> TYPE: PRT
<213> ORGANISM: Bacillus subtilis

<400> SEQUENCE: 10

Met Lys Ile Ala Lys Val Ile Asn Asn Val Ile Ser Val Val Asn
1               5                   10                  15

Glu Gln Gly Lys Glu Leu Val Val Met Gly Arg Gly Leu Ala Phe Gln
            20                  25                  30

Lys Lys Ser Gly Asp Asp Val Asp Glu Ala Arg Ile Glu Lys Val Phe
        35                  40                  45

Thr Leu Asp Asn Lys Asp Val Ser Glu Lys Phe Lys Thr Leu Leu Tyr
    50                  55                  60

Asp Ile Pro Ile Glu Cys Met Glu Val Ser Glu Ile Ile Ser Tyr
65                  70                  75                  80

Ala Lys Leu Gln Leu Gly Lys Lys Leu Asn Asp Ser Ile Tyr Val Ser
                85                  90                  95

Leu Thr Asp His Ile Asn Phe Ala Ile Gln Arg Asn Gln Lys Gly Leu
            100                 105                 110

Asp Ile Lys Asn Ala Leu Leu Trp Glu Thr Lys Arg Leu Tyr Lys Asp
        115                 120                 125

Glu Phe Ala Ile Gly Lys Glu Ala Leu Val Met Val Lys Asn Lys Thr
    130                 135                 140

Gly Val Ser Leu Pro Glu Asp Glu Ala Gly Phe Ile Ala Leu His Ile
145                 150                 155                 160

Val Asn Ala Glu Leu Asn Glu Glu Met Pro Asn Ile Ile Asn Ile Thr
                165                 170                 175

Lys Val Met Gln Glu Ile Leu Ser Ile Val Lys Tyr His Phe Lys Ile
            180                 185                 190

Glu Phe Asn Glu Glu Ser Leu His Tyr Tyr Arg Phe Val Thr His Leu
        195                 200                 205

Lys Phe Phe Ala Gln Arg Leu Phe Asn Gly Thr His Met Glu Ser Gln
    210                 215                 220

Asp Asp Phe Leu Leu Asp Thr Val Lys Glu Lys Tyr His Arg Ala Tyr
225                 230                 235                 240

Glu Cys Thr Lys Lys Ile Gln Thr Tyr Ile Glu Arg Glu Tyr Glu His
                245                 250                 255
```

Lys Leu Thr Ser Asp Glu Leu Leu Tyr Leu Thr Ile His Ile Glu Arg
            260                 265                 270

Val Val Lys Gln Ala
        275

<210> SEQ ID NO 11
<211> LENGTH: 168
<212> TYPE: DNA
<213> ORGANISM: Bacillus subtilis

<400> SEQUENCE: 11
atgaaaattg cgaaggtgat caacaataat gtgatcagcg tggtcaatga acaggggaaa        60
gaattggtcg tcatgggcag ggggctcgcg tttcagaaaa agtccggcga tgatgtcgat       120
gaagcccgca ttgagaaagt gttcacgctc gataacaagg atgtatca                    168

<210> SEQ ID NO 12
<211> LENGTH: 56
<212> TYPE: PRT
<213> ORGANISM: Bacillus subtilis

<400> SEQUENCE: 12

Met Lys Ile Ala Lys Val Ile Asn Asn Asn Val Ile Ser Val Val Asn
1               5                   10                  15

Glu Gln Gly Lys Glu Leu Val Val Met Gly Arg Gly Leu Ala Phe Gln
            20                  25                  30

Lys Lys Ser Gly Asp Asp Val Asp Glu Ala Arg Ile Glu Lys Val Phe
        35                  40                  45

Thr Leu Asp Asn Lys Asp Val Ser
    50                  55

<210> SEQ ID NO 13
<211> LENGTH: 393
<212> TYPE: DNA
<213> ORGANISM: Bacteriophage MS2

<400> SEQUENCE: 13
atggcttcta actttactca gttcgttctc gtcgacaatg gcggaactgg cgacgtgact        60
gtcgccccaa gcaacttcgc taacggggtc gctgaatgga tcagctctaa ctcgcgttca       120
caggcttaca agtaacctg tagcgttcgt cagagctctg cgcagaatcg caaatacacc       180
atcaaagtcg aggtgcctaa agtggcaacc cagactgttg gtggtgtaga gcttcctgta       240
gccgcatggc gttcgtactt aaatatggaa ctaaccattc caattttcgc tacgaattcc       300
gactgcgagc ttattgttaa ggcaatgcaa ggtctcctaa agatggaaa cccgattccc        360 tcagcaatcg cagcaaactc cggcatctac taa                                    393

<210> SEQ ID NO 14
<211> LENGTH: 130
<212> TYPE: PRT
<213> ORGANISM: Bacteriophage MS2

<400> SEQUENCE: 14

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

-continued

```
Val Arg Gln Ser Ser Ala Gln Asn Arg Lys Tyr Thr Ile Lys Val Glu
 50                  55                  60
Val Pro Lys Val Ala Thr Gln Thr Val Gly Gly Val Glu Leu Pro Val
 65                  70                  75                  80
Ala Ala Trp Arg Ser Tyr Leu Asn Met Glu Leu Thr Ile Pro Ile Phe
                 85                  90                  95
Ala Thr Asn Ser Asp Cys Glu Leu Ile Val Lys Ala Met Gln Gly Leu
            100                 105                 110
Leu Lys Asp Gly Asn Pro Ile Pro Ser Ala Ile Ala Ala Asn Ser Gly
        115                 120                 125
Ile Tyr
    130

<210> SEQ ID NO 15
<211> LENGTH: 15
<212> TYPE: RNA
<213> ORGANISM: Artificial Sequence
<220> FEATURE:
<223> OTHER INFORMATION: boxB RNA sequence

<400> SEQUENCE: 15
gcccugaaaa agggc                                                      15

<210> SEQ ID NO 16
<211> LENGTH: 11
<212> TYPE: RNA
<213> ORGANISM: Artificial Sequence
<220> FEATURE:
<223> OTHER INFORMATION: 11mer of the box B RNA sequence

<400> SEQUENCE: 16
gcccugaaaa a                                                          11

<210> SEQ ID NO 17
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 17
ggauuguuac ugcgaaagca ggcaaaacc                                       29

<210> SEQ ID NO 18
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 18
ggauuguuac ugauaaagca ggcaaaacc                                       29

<210> SEQ ID NO 19
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)
```

```
<400> SEQUENCE: 19
gguuuguuac ugauaaagca ggcaagacc                                        29

<210> SEQ ID NO 20
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 20
ggauugugac ugguaaagca ggcaagacc                                        29

<210> SEQ ID NO 21
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 21
acguguuacu gauucgauca ggcaucagu                                        29

<210> SEQ ID NO 22
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 22
ggauuguuac ugcacaggca ggcaagacc                                        29

<210> SEQ ID NO 23
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 23
ggaauguaac ugcacaggca ggcaguacc                                        29

<210> SEQ ID NO 24
<211> LENGTH: 30
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 24
agauuguuac cgauucgauc gggcaaaacc                                       30

<210> SEQ ID NO 25
<211> LENGTH: 29
<212> TYPE: RNA
```

```
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 25
ggauuguuac ugauaaugca ggcaagacc                                         29

<210> SEQ ID NO 26
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 26
acguguaacu aauucgauua ggcaugagu                                         29

<210> SEQ ID NO 27
<211> LENGTH: 34
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 27
gugaauguua guaacauuga uuacgcauga ucac                                   34

<210> SEQ ID NO 28
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 28
ggauagugau uauuaaguua agcuagacc                                         29

<210> SEQ ID NO 29
<211> LENGTH: 35
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 29
uguggauugu gacuauuuaa uuaggcgaga ccaca                                  35

<210> SEQ ID NO 30
<211> LENGTH: 44
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 30
ggauugcgac uguauauccc ucagcgggaa auacaggcaa aacc                        44
```

```
<210> SEQ ID NO 31
<211> LENGTH: 30
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 31
ggguugcuac ugccauuggc aggcaaaacc                                          30

<210> SEQ ID NO 32
<211> LENGTH: 30
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 32
ggauuguuac cgcacuaagc gggcaaaacc                                          30

<210> SEQ ID NO 33
<211> LENGTH: 29
<212> TYPE: RNA
<213> ORGANISM: Artificial Sequence
<220> FEATURE:
<223> OTHER INFORMATION: RNA nucleotide sequence recognized by a protein
      homologous to the Bacillus subtilis LicT protein (family of the
      LicT/SacY)

<400> SEQUENCE: 33
ggauuguuac ugcauucgca ggcaaaacc                                           29

<210> SEQ ID NO 34
<211> LENGTH: 29
<212> TYPE: RNA
<213> ORGANISM: Artificial Sequence
<220> FEATURE:
<223> OTHER INFORMATION: The 29-mer sequence recognition pattern on the
      B.subtilis ribonucleic anti-terminator (RAT) for binding to LicT;
      N = A, G, U or C
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (8)..(8)
<223> OTHER INFORMATION: n is a, c, g, or u
<220> FEATURE:
<221> NAME/KEY: misc_feature
<222> LOCATION: (13)..(16)
<223> OTHER INFORMATION: n is a, c, g, or u
<220> FEATURE:
<221> NAME/KEY: misc_feature
<222> LOCATION: (26)..(27)
<223> OTHER INFORMATION: n is a, c, g, or u

<400> SEQUENCE: 34
ggnuugunac ugnnnnagca ggcaanncc                                           29

<210> SEQ ID NO 35
<211> LENGTH: 19
<212> TYPE: RNA
<213> ORGANISM: Artificial Sequence
<220> FEATURE:
```

```
<223> OTHER INFORMATION: An RNA recognition sequence for the
      bacteriophage MS2 coat protein

<400> SEQUENCE: 35
acaugaggau cacccauga                                                      19

<210> SEQ ID NO 36
<211> LENGTH: 14
<212> TYPE: RNA
<213> ORGANISM: Artificial Sequence
<220> FEATURE:
<223> OTHER INFORMATION: An RNA recognition sequence for the
      bacteriophage MS2 coat protein

<400> SEQUENCE: 36
ccacagucac aggg                                                           14

<210> SEQ ID NO 37
<211> LENGTH: 18
<212> TYPE: RNA
<213> ORGANISM: Artificial Sequence
<220> FEATURE:
<223> OTHER INFORMATION: An RNA recognition sequence for the
      bacteriophage MS2 coat protein

<400> SEQUENCE: 37
ccggaggauc accacggg                                                       18

<210> SEQ ID NO 38
<211> LENGTH: 18
<212> TYPE: RNA
<213> ORGANISM: Artificial Sequence
<220> FEATURE:
<223> OTHER INFORMATION: An RNA recognition sequence for the
      bacteriophage MS2 coat protein

<400> SEQUENCE: 38
ccggaggauc accacggg                                                       18

<210> SEQ ID NO 39
<211> LENGTH: 14
<212> TYPE: RNA
<213> ORGANISM: Artificial Sequence
<220> FEATURE:
<223> OTHER INFORMATION: An RNA recognition sequence for the
      bacteriophage MS2 coat protein

<400> SEQUENCE: 39
ucgccaacag gcgg                                                           14

<210> SEQ ID NO 40
<211> LENGTH: 19
<212> TYPE: RNA
<213> ORGANISM: Artificial Sequence
<220> FEATURE:
<223> OTHER INFORMATION: A 19-mer sequence recognition pattern for
      binding to the bacteriophage MS2 coat protein, wherein N1-N5 are
      the reverse complementary of N15-N19 and N7-N8 are the reverse
      complementary of N13-N14
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (7)..(8)
<223> OTHER INFORMATION: n is a, c, g, or u
<220> FEATURE:
<221> NAME/KEY: misc_feature
```

<222> LOCATION: (10)..(10)
<223> OTHER INFORMATION: n is a, c, g, or u
<220> FEATURE:
<221> NAME/KEY: misc_feature
<222> LOCATION: (13)..(19)
<223> OTHER INFORMATION: n is a, c, g, or u

<400> SEQUENCE: 40
nnnnnrnnan yannnnnnn         19

<210> SEQ ID NO 41
<211> LENGTH: 574
<212> TYPE: DNA
<213> ORGANISM: Artificial Sequence
<220> FEATURE:
<223> OTHER INFORMATION: chimeric RNAi molecule

<400> SEQUENCE: 41
cggaccgcat acgtcttcc ttctctgttg ttccgtcgcc taaggtctct gacacggtcg      60
ttgagcccta caacgcaact ctttctgttc atcaacttgt tgagaacacc gacgagactt     120
actgcatcgg gattgttact gcgaaagcag gcaaaacccg atgcagtaag tctcgtcggt     180
gttctcaaca agttgatgaa cagaaagagt tgcgttgtag ggctcaacga ccgtgtcaga     240
gaccttaggc gacggaacaa cagagaagga agacgtaatg cggtccggat actcctcacg     300
aatctttgaa atgagcaaag ttcccattcc agagccagtt ccaccaccaa gcagtgagt      360 caattgaaaa ccttgaagac aatcacaacc ctcagcctct tttcgaacaa catccaggat     420
tgttactgcg aaagcaggca aaacctggat gttgttcgaa agaggctga gggttgtgat      480 tgtcttcaag gttttcaatt gactcactcg cttggtggtg gaactggctc tggaatggga     540
actttgctca tttcaaagat tcgtgaggag tatc                                 574

<210> SEQ ID NO 42
<211> LENGTH: 568
<212> TYPE: DNA
<213> ORGANISM: Artificial Sequence
<220> FEATURE:
<223> OTHER INFORMATION: chimeric RNAi molecule

<400> SEQUENCE: 42
cagacagaat catgagctca ttctcggttg taccatcgcc aaaggtgtcc gacacagttg      60
tagaaccata caatgccacc ctctccgtcc accagcttgt tgagaacacc gatgagacct     120
actgcattgg attgttactg cgaaagcagg caaaaccaat gcagtaggtc tcatcggtgt     180
tctcaacaag ctggtggacg gagagggtgg cattgtatgg ttctacaact gtgtcggaca     240
cctttggcga tggtacaacc gagaatgagc tcatgattct gtctgggtac tcttcgcgga     300
ttttggagat gagaagtgtt cccattccag atccggttcc tcctccgaga gagtgagtga     360
gttggaatcc ttgaagacaa tcgcatcctt cggcttcctt gcggatcacg tcggattgtt     420
actgcgaaag caggcaaaac cgacgtgatc cgcaaggaag ccgaaggatg cgattgtctt     480
caaggattcc aactcactca ctctctcgga ggaggaaccg gatctggaat gggaacactt     540
ctcatctcca aaatccgcga agagtacc                                        568

<210> SEQ ID NO 43
<211> LENGTH: 744
<212> TYPE: DNA
<213> ORGANISM: Artificial Sequence
<220> FEATURE:
<223> OTHER INFORMATION: chimeric RNAi molecule

```
<400> SEQUENCE: 43
tacccagaat gccggagacg tcgtcgtcca tccctacaac agcatcctag ccatgaggag      60
attgacacag aatgccgact cggtggtggt gctggataac ggcgctctct cacatattgc     120
agccgataga ctccacgtgc aagagccgtc ttttcagcag acaaatcaac tgggattgtt     180
actgcgaaag caggcaaaac ccagttgatt tgtctgctga aaagacggct cttgcacgtg     240
gagtctatcg gctgcaatat gtgagagagc gccgttatcc agcaccacca ccgagtcggc     300
attctgtgtc aatctcctca tggctaggat gctgttgtag ggatggacga cgacgtctcc     360
ggcattctgg gtatccggaa ataccgaata cgtttgtatg atcttcttgg gaaatcggtc     420
atttagcctt tccaagagga atgagcccag acctgagcct gtgccaccag caatcgaatg     480
cagcatcata aagccctcga gtgagtcgct tccatctgct tccctatcaa tcatctccat     540
aatgggattg ttactgcgaa agcaggcaaa acccattatg agatgattg ataggggaagc     600 agatggaagc gactcactcg agggctttat gatgctgcat tcgattgctg gtggcacagg     660
ctcaggtctg ggctcattcc tcttggaaag gctaaatgac cgatttccca agaagatcat     720
acaaacgtat tcggtatttc cgga                                            744

<210> SEQ ID NO 44
<211> LENGTH: 574
<212> TYPE: DNA
<213> ORGANISM: Artificial Sequence
<220> FEATURE:
<223> OTHER INFORMATION: chimeric RNAi molecule

<400> SEQUENCE: 44
cagacagaat catgaacacc tactccgttg tgccctcacc aaaggtatcc gacacagttg      60
tcgagccata caatgccacc ctctccgttc atcagctcgt cgaaaacacc gatgaaacct     120
actgtatcgg gattgttact gcgaaagcag gcaaacccg atacagtagg tttcatcggt     180
gttttcgacg agctgatgaa cggagagggt ggcattgtat ggctcgacaa ctgtgtcgga     240
tacctttggt gagggcacaa cggagtaggt gttcatgatt ctgtctgggt attcctcgcg     300
gattttcgag atcagcaatg ttcccattcc tgatccggta ccacctccca acgaatgagt     360
cagctggaat ccctgtaagc aatcgcagct ctcggcttcc tttctgacta cgtcgaggat     420
tgttactgcg aaagcaggca aaacctcgac gtagtcagaa aggaagccga gagctgcgat     480
tgcttacagg gattccagct gactcattcg ttgggaggtg gtaccggatc aggaatggga     540
acattgctga tctcgaaaat ccgcgaggaa tacc                                 574

<210> SEQ ID NO 45
<211> LENGTH: 546
<212> TYPE: DNA
<213> ORGANISM: Artificial Sequence
<220> FEATURE:
<223> OTHER INFORMATION: chimeric RNAi molecule

<400> SEQUENCE: 45
cggaccgcat tacgtcttcc ttctctgttg ttccgtcgcc taaggtctct gacacggtcg      60
ttgagcccta caacgcaact ctttctgttc atcaacttgt tgagaacacc gacgagactt     120
actgcatcgg ccctgaaaaa gggccgatgc agtaagtctc gtcggtgttc tcaacaagtt     180
gatgaacaga aagagttgcg ttgtagggct caacgaccgt gtcagagacc ttaggcgacg     240
gaacaacaga gaaggaagac gtaatgcggt ccggatactc ctcacgaatc tttgaaatga     300
gcaaagttcc cattccagag ccagttccac caccaagcga gtgagtcaat gaaaaaccctt    360
```

```
gaagacaatc acaaccctca gcctcttttc gaacaacatc cagccctgaa aaagggctgg    420
atgttgttcg aaaagaggct gagggttgtg attgtcttca aggttttcaa ttgactcact    480
cgcttggtgg tggaactggc tctggaatgg gaactttgct catttcaaag attcgtgagg    540
agtatc                                                               546
```

<210> SEQ ID NO 46
<211> LENGTH: 540
<212> TYPE: DNA
<213> ORGANISM: Artificial Sequence
<220> FEATURE:
<223> OTHER INFORMATION: chimeric RNAi molecule

<400> SEQUENCE: 46

```
cagacagaat catgagctca ttctcggttg taccatcgcc aaaggtgtcc gacacagttg     60
tagaaccata caatgccacc ctctccgtcc accagcttgt tgagaacacc gatgagacct    120
actgcattgc cctgaaaaag gcaatgcag taggtctcat cggtgttctc aacaagctgg     180
tggacggaga gggtggcatt gtatggttct acaactgtgt cggacacctt ggcgatggt     240 acaaccgaga atgagctcat gattctgtct gggtactctt cgcggatttt ggagatgaga    300
agtgttccca ttccagatcc ggttcctcct ccgagagagt gagtgagttg gaatccttga    360
agacaatcgc atccttcggc ttccttgcgg atcacgtcgc cctgaaaaag gcgacgtga     420 tccgcaagga agccgaagga tgcgattgtc ttcaaggatt ccaactcact cactctctcg    480
gaggaggaac cggatctgga atgggaacac ttctcatctc caaaatccgc gaagagtacc    540
```

<210> SEQ ID NO 47
<211> LENGTH: 716
<212> TYPE: DNA
<213> ORGANISM: Artificial Sequence
<220> FEATURE:
<223> OTHER INFORMATION: chimeric RNAi molecule

<400> SEQUENCE: 47

```
tacccagaat gccggagacg tcgtcgtcca tccctacaac agcatcctag ccatgaggag     60
attgacacag aatgccgact cggtggtggt gctggataac ggcgctctct cacatattgc    120
agccgataga ctccacgtgc aagagccgtc ttttcagcag acaaatcaac tggccctgaa    180
aaagggccag ttgatttgtc tgctgaaaag acggctcttg cacgtggagt ctatcggctg    240
caatatgtga gagagcgccg ttatccagca ccaccaccga gtcggcattc tgtgtcaatc    300
tcctcatggc taggatgctg ttgtagggat ggacgacgc gtctccggca ttctgggtat     360
ccggaaatac cgaatacgtt tgtatgatct tcttgggaaa tcggtcattt agccttccca    420
agaggaatga gccagaccct gagcctgtgc caccagcaat cgaatgcagc atcataaagc    480
cctcgagtga gtcgcttcca tctgcttccc tatcaatcat ctccataatg gccctgaaaa    540
agggccatta tggagatgat tgataggaa gcagatggaa gcgactcact cgagggcttt    600
atgatgctgc attcgattgc tggtggcaca ggctcaggtc tgggctcatt cctcttggaa    660
aggctaaatg accgatttcc caagaagatc atacaaacgt attcggtatt tccgga        716
```

<210> SEQ ID NO 48
<211> LENGTH: 546
<212> TYPE: DNA
<213> ORGANISM: Artificial Sequence
<220> FEATURE:
<223> OTHER INFORMATION: chimeric RNAi molecule

```
<400> SEQUENCE: 48
cagacagaat catgaacacc tactccgttg tgccctcacc aaaggtatcc gacacagttg    60
tcgagccata caatgccacc ctctccgttc atcagctcgt cgaaaacacc gatgaaacct   120
actgtatcgg ccctgaaaaa gggccgatac agtaggtttc atcggtgttt tcgacgagct   180
gatgaacgga gagggtggca ttgtatggct cgacaactgt gtcggatacc tttggtgagg   240
gcacaacgga gtaggtgttc atgattctgt ctgggtattc ctcgcggatt ttcgagatca   300
gcaatgttcc cattcctgat ccggtaccac ctcccaacga atgagtcagc tggaatccct   360
gtaagcaatc gcagctctcg gcttcctttc tgactacgtc gagccctgaa aaagggctcg   420
acgtagtcag aaaggaagcc gagagctgcg attgcttaca gggattccag ctgactcatt   480
cgttgggagg tggtaccgga tcaggaatgg gaacattgct gatctcgaaa atccgcgagg   540
aatacc                                                             546

<210> SEQ ID NO 49
<211> LENGTH: 554
<212> TYPE: DNA
<213> ORGANISM: Artificial Sequence
<220> FEATURE:
<223> OTHER INFORMATION: chimeric RNAi molecule

<400> SEQUENCE: 49
cggaccgcat tacgtcttcc ttctctgttg ttccgtcgcc taaggtctct gacacggtcg    60
ttgagcccta caacgcaact ctttctgttc atcaacttgt tgagaacacc gacgagactt   120
actgcatcga catgaggatc acccatgacg atgcagtaag tctcgtcggt gttctcaaca   180
agttgatgaa cagaaagagt tgcgttgtag ggctcaacga ccgtgtcaga gaccttaggc   240
gacggaacaa cagagaagga agacgtaatg cggtccggat actcctcacg aatctttgaa   300
atgagcaaag ttcccattcc agagccagtt ccaccaccaa gcgagtgagt caattgaaaa   360
ccttgaagac aatcacaacc ctcagcctct tttcgaacaa catccaacat gaggatcacc   420
catgatggat gttgttcgaa agaggctgaa gggttgtgat tgtcttcaag gttttcaatt   480
gactcactcg cttggtggtg gaactggctc tggaatggga actttgctca tttcaaagat   540
tcgtgaggag tatc                                                    554

<210> SEQ ID NO 50
<211> LENGTH: 548
<212> TYPE: DNA
<213> ORGANISM: Artificial Sequence
<220> FEATURE:
<223> OTHER INFORMATION: chimeric RNAi molecule

<400> SEQUENCE: 50
cagacagaat catgagctca ttctcggttg taccatcgcc aaaggtgtcc gacacagttg    60
tagaaccata caatgccacc ctctccgtcc accagcttgt tgagaacacc gatgagacct   120
actgcattac atgaggatca cccatgaaat gcagtaggtc tcatcggtgt tctcaacaag   180
ctggtggacg gagagggtgg cattgtatgg ttctacaact gtgtcggaca cctttggcga   240
tggtacaacc gagaatgagc tcatgattct gtctgggtac tcttcgcgga ttttggagat   300
gagaagtgtt cccattccag atccggttcc tcctccgaga gagtgagtga gttggaatcc   360
ttgaagacaa tcgcatcctt cggcttcctt gcggatcacg tcacatgagg atcacccatg   420
agacgtgatc cgcaaggaag ccgaaggatg cgattgtctt caaggattcc aactcactca   480
ctctctcgga ggaggaaccg gatctggaat gggaacactt ctcatctcca aaatccgcga   540
``` agagtacc 548

<210> SEQ ID NO 51
<211> LENGTH: 724
<212> TYPE: DNA
<213> ORGANISM: Artificial Sequence
<220> FEATURE:
<223> OTHER INFORMATION: chimeric RNAi molecule

<400> SEQUENCE: 51

```
tacccagaat gccggagacg tcgtcgtcca tccctacaac agcatcctag ccatgaggag     60
attgacacag aatgccgact cggtggtggt gctggataac ggcgctctct cacatattgc    120
agccgataga ctccacgtgc aagagccgtc ttttcagcag acaaatcaac tgacatgagg    180
atcacccatg acagttgatt tgtctgctga aaagacggct cttgcacgtg gagtctatcg    240
gctgcaatat gtgagagagc gccgttatcc agcaccacca ccgagtcggc attctgtgtc    300
aatctcctca tggctaggat gctgttgtag ggatggacga cgacgtctcc ggcattctgg    360
gtatccggaa ataccgaata cgtttgtatg atcttcttgg gaaatcggtc atttagcctt    420
tccaagagga atgagcccag acctgagcct gtgccaccag caatcgaatg cagcatcata    480
aagccctcga gtgagtcgct tccatctgct tccctatcaa tcatctccat aatgacatga    540
ggatcaccca tgacattatg gagatgattg atagggaagc agatggaagc gactcactcg    600
agggctttat gatgctgcat tcgattgctg gtggcacagg ctcaggtctg ggctcattcc    660
tcttggaaag gctaaatgac cgatttccca agaagatcat acaaacgtat cggtatttc    720
cgga                                                                  724
```

<210> SEQ ID NO 52
<211> LENGTH: 554
<212> TYPE: DNA
<213> ORGANISM: Artificial Sequence
<220> FEATURE:
<223> OTHER INFORMATION: chimeric RNAi molecule

<400> SEQUENCE: 52

```
cagacagaat catgaacacc tactccgttg tgccctcacc aaaggtatcc gacacagttg     60
tcgagccata caatgccacc ctctccgttc atcagctcgt cgaaaacacc gatgaaacct    120
actgtatcga catgaggatc acccatgacg atacagtagg tttcatcggt gttttcgacg    180
agctgatgaa cggagagggt ggcattgtat ggctcgacaa ctgtgtcgga tacctttggt    240
gagggcacaa cggagtaggt gttcatgatt ctgtctgggt attcctcgcg gattttcgag    300
atcagcaatg ttcccattcc tgatccggta ccacctccca acgaatgagt cagctggaat    360
ccctgtaagc aatcgcagct ctcggcttcc tttctgacta cgtcgaacat gaggatcacc    420
catgatcgac gtagtcagaa aggaagccga gagctgcgat tgcttacagg gattccagct    480
gactcattcg ttgggaggtg gtaccggatc aggaatggga acattgctga tctcgaaaat    540
ccgcgaggaa tacc                                                       554
```

<210> SEQ ID NO 53
<211> LENGTH: 15
<212> TYPE: DNA
<213> ORGANISM: Artificial Sequence
<220> FEATURE:
<223> OTHER INFORMATION: linker polypeptide

<400> SEQUENCE: 53

```
ggggsggggs ggggs                                                     15
```

<210> SEQ ID NO 54
<211> LENGTH: 898
<212> TYPE: DNA
<213> ORGANISM: Artificial Sequence
<220> FEATURE:
<223> OTHER INFORMATION: chimeric RNAi molecule

<400> SEQUENCE: 54

```
atacttctcg tggaacatgg caggaagtcg gaactttccc agattgtaca gccaaggtta    60
ataagcttgt tcctggaaag gaatacgcat tccgtgtcaa ggcagtcaat cttcaaggag   120
aatcaaaacc attggaagct gaagaaccaa ttattgcaaa gaatcaattt gatgttcctg   180
atccagttga caaaccagag gttactgact ggattgttac tgcgaaagca ggcaaaacca   240
gtcagtaacc tctggtttgt caactggatc aggaacatca aattgattct ttgcaataat   300
tggttcttca gcttccaatg gttttgattc tccttgaaga ttgactgcct tgacacggaa   360
tgcgtattcc tttccaggaa caagcttatt aaccttggct gtacaatctg ggaaagttcc   420
gacttcctgc catgttccac gagaagtatc catcttctca acaatgtagt gaagaacatc   480
agttcctccg ttatcagttg gaggcttcca gttcaatgta catccttcct tatggatctc   540
gtcaatcttg agtggtcctt ctggagttcc tggtacatca agaacagtaa cattgcactg   600
agcagtatct tttccatgct cattttcaac aatgattttg taaactccag tatctccacg   660
gattgttact gcgaaagcag gcaaaaccgt ggagatactg gagtttacaa aatcattgtt   720
gaaaatgagc atgaaaaga tactgctcag tgcaatgtta ctgttcttga tgtaccagga    780
actccagaag gaccactcaa gattgacgag atccataagg aaggatgtac attgaactgg   840
aagcctccaa ctgataacgg aggaactgat gttcttcact acattgttga agatgg       898
```

<210> SEQ ID NO 55
<211> LENGTH: 870
<212> TYPE: DNA
<213> ORGANISM: Artificial Sequence
<220> FEATURE:
<223> OTHER INFORMATION: chimeric RNAi molecule

<400> SEQUENCE: 55

```
atacttctcg tggaacatgg caggaagtcg gaactttccc agattgtaca gccaaggtta    60
ataagcttgt tcctggaaag gaatacgcat tccgtgtcaa ggcagtcaat cttcaaggag   120
aatcaaaacc attggaagct gaagaaccaa ttattgcaaa gaatcaattt gatgttcctg   180
atccagttga caaaccagag gttactgact gccctgaaaa agggcagtca gtaacctctg   240
gtttgtcaac tggatcagga acatcaaatt gattctttgc aataattggt tcttcagctt   300
ccaatggttt tgattctcct tgaagattga ctgccttgac acggaatgcg tattcctttc   360
caggaacaag cttattaacc ttggctgtac aatctgggaa agttccgact tcctgccatg   420
ttccacgaga agtatccatc ttctcaacaa tgtagtgaag aacatcagtt cctccgttat   480
cagttggagg cttccagttc aatgtacatc cttccttatg gatctcgtca atcttgagtg   540
gtccttctgg agttcctggt acatcaagaa cagtaacatt gcactgagca gtatcttttc   600
catgctcatt ttcaacaatg attttgtaaa ctccagtatc tccacgccct gaaaagggc    660
gtggagatac tggagtttac aaaatcattg ttgaaaatga gcatgaaaaa gatactgctc   720
agtgcaatgt tactgttctt gatgtaccag gaactccaga aggaccactc aagattgacg   780
agatccataa ggaaggatgt acattgaact ggaagcctcc aactgataac ggaggaactg   840
```

```
atgttcttca ctacattgtt gagaagatgg                                    870

<210> SEQ ID NO 56
<211> LENGTH: 878
<212> TYPE: DNA
<213> ORGANISM: Artificial Sequence
<220> FEATURE:
<223> OTHER INFORMATION: chimeric RNAi molecule

<400> SEQUENCE: 56
atacttctcg tggaacatgg caggaagtcg gaactttccc agattgtaca gccaaggtta    60
ataagcttgt tcctggaaag gaatacgcat tccgtgtcaa ggcagtcaat cttcaaggag   120
aatcaaaacc attggaagct gaagaaccaa ttattgcaaa gaatcaattt gatgttcctg   180
atccagttga caaccagag gttactgact acatgaggat cacccatgaa gtcagtaacc    240
tctggtttgt caactggatc aggaacatca aattgattct ttgcaataat tggttcttca   300
gcttccaatg gttttgattc tccttgaaga ttgactgcct tgacacggaa tgcgtattcc   360
tttccaggaa caagcttatt aaccttggct gtacaatctg ggaaagttcc gacttcctgc   420
catgttccac gagaagtatc catcttctca acaatgtagt gaagaacatc agttcctccg   480
ttatcagttg gaggcttcca gttcaatgta catccttcct tatggatctc gtcaatcttg   540
agtggtcctt ctggagttcc tggtacatca agaacagtaa cattgcactg agcagtatct   600
tttccatgct cattttcaac aatgattttg taaactccag tatctccaca catgaggatc   660
acccatgagt ggagatactg gagtttacaa aatcattgtt gaaatgagc atggaaaaga    720
tactgctcag tgcaatgtta ctgttcttga tgtaccagga actccagaag gaccactcaa   780
gattgacgag atccataagg aaggatgtac attgaactgg aagcctccaa ctgataacgg   840
aggaactgat gttcttcact acattgttga gaagatgg                           878

<210> SEQ ID NO 57
<211> LENGTH: 545
<212> TYPE: DNA
<213> ORGANISM: Artificial Sequence
<220> FEATURE:
<223> OTHER INFORMATION: chimeric RNAi molecule

<400> SEQUENCE: 57
tggatgttgt tcgaaaagag gctgagggtt gtgattgtct tcaaggtttt caattgactc    60
actcgcttgg tggtggaact ggctctggaa tgggaacttt gctcatttca aagattcgtg   120
aggagtatcc ggaccgcatt acgtcttcct tctctgttgt tccgtcgcct aaggtctctg   180
acacggtcgt tgagccctac aacgcaactc tttctgttca tcaacttgtt gagaacaccg   240
acgagactta ctgcatcggg attgttactg cgaaagcagg caaaacccga tgcagtaagt   300
ctcgtcggtg ttctcaacaa gttgatgaac agaaagagtt gcgttgtagg gctcaacgac   360
cgtgtcagag accttaggcg acggaacaac agagaaggaa gacgtaatgc ggtccggata   420
ctcctcacga atctttgaaa tgagcaaagt tcccattcca gagccagttc caccaccaag   480
cgagtgagtc aattgaaaac cttgaagaca atcacaaccc tcagcctctt ttcgaacaac   540
atcca                                                               545

<210> SEQ ID NO 58
<211> LENGTH: 539
<212> TYPE: DNA
<213> ORGANISM: Artificial Sequence
<220> FEATURE:
```

<223> OTHER INFORMATION: chimeric RNAi molecule

<400> SEQUENCE: 58

| gacgtgatcc gcaaggaagc cgaaggatgc gattgtcttc aaggattcca actcactcac | 60 |
| tctctcggag gaggaaccgg atctggaatg ggaacacttc tcatctccaa aatccgcgaa | 120 |
| gagtacccag acagaatcat gagctcattc tcggttgtac catcgccaaa ggtgtccgac | 180 |
| acagttgtag aaccatacaa tgccacccte tccgtccacc agcttgttga aacaccgat | 240 |
| gagacctact gcattggatt gttactgcga aagcaggcaa aaccaatgca gtaggtctca | 300 |
| tcggtgttct caacaagctg gtggacgag agggtggcat tgtatggttc tacaactgtg | 360 |
| tcggacacct ttggcgatgg tacaaccgag aatgagctca tgattctgtc tgggtactct | 420 |
| tcgcggattt tggagatgag aagtgttccc attccagatc cggttcctcc tccgagagag | 480 |
| tgagtgagtt ggaatccttg aagacaatcg catccttcgg cttccttgcg gatcacgtc | 539 |

<210> SEQ ID NO 59
<211> LENGTH: 715
<212> TYPE: DNA
<213> ORGANISM: Artificial Sequence
<220> FEATURE:
<223> OTHER INFORMATION: chimeric RNAi molecule

<400> SEQUENCE: 59

| cattatggag atgattgata gggaagcaga tggaagcgac tcactcgagg gctttatgat | 60 |
| gctgcattcg attgctggtg gcacaggctc aggtctgggc tcattcctct tggaaaggct | 120 |
| aaatgaccga tttcccaaga agatcataca acgtattcg gtatttccgg atacccagaa | 180 |
| tgccggagac gtcgtcgtcc atccctacaa cagcatccta gccatgagga gattgacaca | 240 |
| gaatgccgac tcgtggtgg tgctggataa cggcgctctc tcacatattg cagccgatag | 300 |
| actccacgtg caagagccgt cttttcagca gacaaatcaa ctgggattgt tactgcgaaa | 360 |
| gcaggcaaaa cccagttgat ttgtctgctg aaaagacggc tcttgcacgt ggagtctatc | 420 |
| ggctgcaata tgtgagagag cgccgttatc cagcaccacc accgagtcgg cattctgtgt | 480 |
| caatctcctc atggctagga tgctgttgta gggatggacg acgacgtctc cggcattctg | 540 |
| ggtatccgga ataccgaat acgtttgtat gatcttcttg ggaaatcggt catttagcct | 600 |
| ttccaagagg aatgagccca gacctgagcc tgtgccacca gcaatcgaat gcagcatcat | 660 |
| aaagccctcg agtgagtcgc ttccatctgc ttccctatca atcatctcca taatg | 715 |

<210> SEQ ID NO 60
<211> LENGTH: 545
<212> TYPE: DNA
<213> ORGANISM: Artificial Sequence
<220> FEATURE:
<223> OTHER INFORMATION: chimeric RNAi molecule

<400> SEQUENCE: 60

| tcgacgtagt cagaaaggaa gccgagagct gcgattgctt acagggattc cagctgactc | 60 |
| attcgttggg aggtggtacc ggatcaggaa tgggaacatt gctgatctcg aaaatccgcg | 120 |
| aggaataccc agacagaatc atgaacacct actccgttgt gccctcacca aaggtatccg | 180 |
| acacagttgt cgagccatac aatgccaccc tctccgttca tcagctcgtc gaaaacaccg | 240 |
| atgaaaccta ctgtatcggg attgttactg cgaaagcagg caaaaccga tacagtaggt | 300 |
| ttcatcggtg ttttcgacga gctgatgaac ggagagggtg gcattgtatg gctcgacaac | 360 |
| tgtgtcggat acctttggtg agggcacaac ggagtaggtg ttcatgattc tgtctgggta | 420 |

```
ttcctcgcgg attttcgaga tcagcaatgt tcccattcct gatccggtac cacctcccaa      480
cgaatgagtc agctggaatc cctgtaagca atcgcagctc tcggcttcct ttctgactac      540
gtcga                                                                  545

<210> SEQ ID NO 61
<211> LENGTH: 531
<212> TYPE: DNA
<213> ORGANISM: Artificial Sequence
<220> FEATURE:
<223> OTHER INFORMATION: chimeric RNAi molecule

<400> SEQUENCE: 61
tggatgttgt tcgaaaagag gctgagggtt gtgattgtct tcaaggtttt caattgactc       60
actcgcttgg tggtggaact ggctctggaa tgggactttt gctcatttca aagattcgtg      120
aggagtatcc ggaccgcatt acgtcttcct tctctgttgt tccgtcgcct aaggtctctg      180
acacggtcgt tgagccctac aacgcaactc tttctgttca tcaacttgtt gagaacaccg      240
acgagactta ctgcatcggc cctgaaaaag gccgatgca gtaagtctcg tcggtgttct      300
caacaagttg atgaacagaa agagttgcgt tgtagggctc aacgaccgtg tcagagacct      360
taggcgacgg aacaacagag aaggaagacg taatgcggtc cggatactcc tcacgaatct      420
ttgaaatgag caaagttccc attccagagc cagttccacc accaagcgag tgagtcaatt      480
gaaaaccttg aagacaatca caaccctcag cctcttttcg aacaacatcc a              531

<210> SEQ ID NO 62
<211> LENGTH: 525
<212> TYPE: DNA
<213> ORGANISM: Artificial Sequence
<220> FEATURE:
<223> OTHER INFORMATION: chimeric RNAi molecule

<400> SEQUENCE: 62
gacgtgatcc gcaaggaagc cgaaggatgc gattgtcttc aaggattcca actcactcac       60
tctctcggag gaggaaccgg atctggaatg gaacacttc tcatctccaa atccgcgaa      120 gagtacccag acagaatcat gagctcattc tcggttgtac catcgccaaa ggtgtccgac      180
acagttgtag aaccatacaa tgccacccctc tccgtccacc agcttgttga gaacaccgat      240
gagacctact gcattgccct gaaaaagggc aatgcagtag gtctcatcgg tgttctcaac      300
aagctggtgg acgagaggg tggcattgta tggttctaca actgtgtcgg cacctttgg      360 cgatggtaca accgagaatg agctcatgat tctgtctggg tactcttcgc ggattttgga      420
gatgagaagt gttcccattc cagatccggt tcctcctccg agagagtgag tgagttggaa      480
tccttgaaga caatcgcatc cttcggcttc cttgcggatc acgtc                      525

<210> SEQ ID NO 63
<211> LENGTH: 701
<212> TYPE: DNA
<213> ORGANISM: Artificial Sequence
<220> FEATURE:
<223> OTHER INFORMATION: chimeric RNAi molecule

<400> SEQUENCE: 63
cattatggag atgattgata gggaagcaga tggaagcgac tcactcgagg gctttatgat       60
gctgcattcg attgctggtg gcacaggctc aggtctgggc tcattcctct tggaaaggct      120
aaatgaccga tttcccaaga agatcataca acgtattcg gtatttccgg atacccagaa      180
```

```
tgccggagac gtcgtcgtcc atccctacaa cagcatccta gccatgagga gattgacaca    240
gaatgccgac tcggtggtgg tgctggataa cggcgctctc tcacatattg cagccgatag    300
actccacgtg caagagccgt cttttcagca gacaaatcaa ctggccctga aaaagggcca    360
gttgatttgt ctgctgaaaa gacggctctt gcacgtggag tctatcggct gcaatatgtg    420
agagagcgcc gttatccagc accaccaccg agtcggcatt ctgtgtcaat ctcctcatgg    480
ctaggatgct gttgtaggga tggacgacga cgtctccggc attctgggta tccggaaata    540
ccgaatacgt ttgtatgatc ttcttgggaa atcggtcatt tagcctttcc aagaggaatg    600
agcccagacc tgagcctgtg ccaccagcaa tcgaatgcag catcataaag ccctcgagtg    660
agtcgcttcc atctgcttcc ctatcaatca tctccataat g                      701

<210> SEQ ID NO 64
<211> LENGTH: 531
<212> TYPE: DNA
<213> ORGANISM: Artificial Sequence
<220> FEATURE:
<223> OTHER INFORMATION: chimeric RNAi molecule

<400> SEQUENCE: 64
tcgacgtagt cagaaaggaa gccgagagct gcgattgctt acagggattc cagctgactc     60
attcgttggg aggtggtacc ggatcaggaa tgggaacatt gctgatctcg aaaatccgcg    120
aggaataccc agacagaatc atgaacacct actccgttgt gccctcacca aaggtatccg    180
acacagttgt cgagccatac aatgccaccc tctccgttca tcagctcgtc gaaaacaccg    240
atgaaaccta ctgtatcggc cctgaaaaag gccgataca gtaggtttca tcggtgtttt    300
cgacgagctg atgaacggag agggtggcat tgtatggctc gacaactgtg tcggatacct    360
ttggtgaggg cacaacggag taggtgttca tgattctgtc tgggtattcc tcgcggattt    420
tcgagatcag caatgttccc attcctgatc cggtaccacc tcccaacgaa tgagtcagct    480
ggaatccctg taagcaatcg cagctctcgg cttcctttct gactacgtcg a             531

<210> SEQ ID NO 65
<211> LENGTH: 535
<212> TYPE: DNA
<213> ORGANISM: Artificial Sequence
<220> FEATURE:
<223> OTHER INFORMATION: chimeric RNAi molecule

<400> SEQUENCE: 65
tggatgttgt tcgaaaagag gctgagggtt gtgattgtct tcaaggtttt caattgactc     60
actcgcttgg tggtggaact ggctctggaa tgggaacttt gctcatttca agattcgtg    120 aggagtatcc ggaccgcatt acgtcttcct tctctgttgt tccgtcgcct aaggtctctg    180
acacggtcgt tgagccctac aacgcaactc tttctgttca tcaacttgtt gagaacaccg    240
acgagactta ctgcatcgac atgaggatca cccatgacga tgcagtaagt ctcgtcggtg    300
ttctcaacaa gttgatgaac agaaagagtt gcgttgtagg gctcaacgac cgtgtcagag    360
accttaggcg acggaacaac agagaaggaa gacgtaatgc ggtccggata ctcctcacga    420
atctttgaaa tgagcaaagt tcccattcca gagccagttc caccaccaag cgagtgagtc    480
aattgaaaac cttgaagaca atcacaaccc tcagcctctt ttcgaacaac atcca         535

<210> SEQ ID NO 66
<211> LENGTH: 529
<212> TYPE: DNA
<213> ORGANISM: Artificial Sequence
```

```
<220> FEATURE:
<223> OTHER INFORMATION: chimeric RNAi molecule

<400> SEQUENCE: 66
gacgtgatcc gcaaggaagc cgaaggatgc gattgtcttc aaggattcca actcactcac    60
tctctcggag gaggaaccgg atctggaatg gaacacttc tcatctccaa aatccgcgaa   120
gagtacccag acagaatcat gagctcattc tcggttgtac catcgccaaa ggtgtccgac   180
acagttgtag aaccatacaa tgccaccctc tccgtccacc agcttgttga aacaccgat    240 gagacctact gcattacatg aggatcaccc atgaaatgca gtaggtctca tcggtgttct   300
caacaagctg gtggacggag agggtggcat tgtatggttc tacaactgtg tcggacacct   360
ttggcgatgg tacaaccgag aatgagctca tgattctgtc tgggtactct tcgcggattt   420
tggagatgag aagtgttccc attccagatc cggttcctcc tccgagagag tgagtgagtt   480
ggaatccttg aagacaatcg catccttcgg cttccttgcg gatcacgtc               529

<210> SEQ ID NO 67
<211> LENGTH: 705
<212> TYPE: DNA
<213> ORGANISM: Artificial Sequence
<220> FEATURE:
<223> OTHER INFORMATION: chimeric RNAi molecule

<400> SEQUENCE: 67
cattatggag atgattgata gggaagcaga tggaagcgac tcactcgagg gctttatgat    60
gctgcattcg attgctggtg gcacaggctc aggtctgggc tcattcctct tggaaaggct   120
aaatgaccga tttcccaaga agatcataca acgtattcg gtatttccgg atacccagaa    180
tgccggagac gtcgtcgtcc atccctacaa cagcatccta gccatgagga gattgacaca   240
gaatgccgac tcggtggtgg tgctggataa cggcgctctc tcacatattg cagccgatag   300
actccacgtg caagagccgt cttttcagca gacaaatcaa ctgacatgag gatcacccat   360
gacagttgat ttgtctgctg aaaagacggc tcttgcacgt ggagtctatc ggctgcaata   420
tgtgagagag cgccgttatc agcaccacc accgagtcgg cattctgtgt caatctcctc   480
atggctagga tgctgttgta gggatggacg acgacgtctc cggcattctg ggtatccgga   540
aataccgaat acgtttgtat gatcttcttg ggaaatcggt catttagcct ttccaagagg   600
aatgagccca gacctgagcc tgtgccacca gcaatcgaat gcagcatcat aaagccctcg   660
agtgagtcgc ttccatctgc ttccctatca atcatctcca taatg                  705

<210> SEQ ID NO 68
<211> LENGTH: 535
<212> TYPE: DNA
<213> ORGANISM: Artificial Sequence
<220> FEATURE:
<223> OTHER INFORMATION: chimeric RNAi molecule

<400> SEQUENCE: 68
tcgacgtagt cagaaaggaa gccgagagct gcgattgctt acagggattc cagctgactc    60
attcgttggg aggtggtacc ggatcaggaa tgggaacatt gctgatctcg aaaatccgcg   120
aggaataccc agacagaatc atgaacacct actccgttgt gccctcacca aaggtatccg   180
acacagttgt cgagccatac aatgccaccc tctccgttca tcagctcgtc gaaaacaccg   240
atgaaaccta ctgtatcgac atgaggatca cccatgacga tacagtaggt ttcatcggtg   300
ttttcgacga gctgatgaac ggagagggtg gcattgtatg gctcgacaac tgtgtcggat   360
```

```
acctttggtg agggcacaac ggagtaggtg ttcatgattc tgtctgggta ttcctcgcgg    420
attttcgaga tcagcaatgt tcccattcct gatccggtac cacctcccaa cgaatgagtc    480
agctggaatc cctgtaagca atcgcagctc tcggcttcct ttctgactac gtcga         535

<210> SEQ ID NO 69
<211> LENGTH: 869
<212> TYPE: DNA
<213> ORGANISM: Artificial Sequence
<220> FEATURE:
<223> OTHER INFORMATION: chimeric RNAi molecule

<400> SEQUENCE: 69
gtggagatac tggagtttac aaaatcattg ttgaaaatga gcatggaaaa gatactgctc     60
agtgcaatgt tactgttctt gatgtaccag gaactccaga aggaccactc aagattgacg    120
agatccataa ggaaggatgt acattgaact ggaagcctcc aactgataac ggaggaactg    180
atgttcttca ctacattgtt gagaagatgg atacttctcg tggaacatgg caggaagtcg    240
gaactttccc agattgtaca gccaaggtta ataagcttgt tcctggaaag gaatacgcat    300
tccgtgtcaa ggcagtcaat cttcaaggag aatcaaaacc attggaagct gaagaaccaa    360
ttattgcaaa gaatcaattt gatgttcctg atccagttga caaaccagag gttactgact    420
ggattgttac tgcgaaagca ggcaaaacca gtcagtaacc tctggtttgt caactggatc    480
aggaacatca aattgattct tgcaataat tggttcttca gcttccaatg gttttgattc     540
tccttgaaga ttgactgcct tgacacggaa tgcgtattcc tttccaggaa caagcttatt    600
aaccttggct gtacaatctg ggaaagttcc gacttcctgc catgttccac gagaagtatc    660
catcttctca acaatgtagt gaagaacatc agttcctccg ttatcagttg gaggcttcca    720
gttcaatgta catccttcct tatggatctc gtcaatcttg agtggtcctt ctggagttcc    780
tggtacatca agaacagtaa cattgcactg agcagtatct tttccatgct cattttcaac    840
aatgattttg taaactccag tatctccac                                      869

<210> SEQ ID NO 70
<211> LENGTH: 855
<212> TYPE: DNA
<213> ORGANISM: Artificial Sequence
<220> FEATURE:
<223> OTHER INFORMATION: chimeric RNAi molecule

<400> SEQUENCE: 70
gtggagatac tggagtttac aaaatcattg ttgaaaatga gcatggaaaa gatactgctc     60
agtgcaatgt tactgttctt gatgtaccag gaactccaga aggaccactc aagattgacg    120
agatccataa ggaaggatgt acattgaact ggaagcctcc aactgataac ggaggaactg    180
atgttcttca ctacattgtt gagaagatgg atacttctcg tggaacatgg caggaagtcg    240
gaactttccc agattgtaca gccaaggtta ataagcttgt tcctggaaag gaatacgcat    300
tccgtgtcaa ggcagtcaat cttcaaggag aatcaaaacc attggaagct gaagaaccaa    360
ttattgcaaa gaatcaattt gatgttcctg atccagttga caaaccagag gttactgact    420
gccctgaaaa agggcagtca gtaacctctg gtttgtcaac tggatcagga acatcaaatt    480
gattctttgc aataattggt tcttcagctt ccaatggttt tgattctcct tgaagattga    540
ctgccttgac acggaatgcg tattcctttc caggaacaag cttattaacc ttggctgtac    600
aatctgggaa agttccgact tcctgccatg ttccacgaga agtatccatc ttctcaacaa    660
tgtagtgaag aacatcagtt cctccgttat cagttggagg cttccagttc aatgtacatc    720
```

```
cttccttatg atctcgtca atcttgagtg gtccttctgg agttcctggt acatcaagaa    780
cagtaacatt gcactgagca gtatctttc catgctcatt tcaacaatg attttgtaaa    840 ctccagtatc tccac                                                   855
```

<210> SEQ ID NO 71
<211> LENGTH: 859
<212> TYPE: DNA
<213> ORGANISM: Artificial Sequence
<220> FEATURE:
<223> OTHER INFORMATION: chimeric RNAi molecule

<400> SEQUENCE: 71

```
gtggagatac tggagtttac aaaatcattg ttgaaaatga gcatggaaaa gatactgctc     60
agtgcaatgt tactgttctt gatgtaccag gaactccaga aggaccactc aagattgacg    120
agatccataa ggaaggatgt acattgaact ggaagcctcc aactgataac ggaggaactg    180
atgttcttca ctacattgtt gagaagatgg atacttctcg tggaacatgg caggaagtcg    240
gaactttccc agattgtaca gccaaggtta ataagcttgt tcctggaaag gaatacgcat    300
tccgtgtcaa gcagtcaat cttcaaggag aatcaaaacc attggaagct gaagaaccaa    360
ttattgcaaa gaatcaattt gatgttcctg atccagttga caaaccagag gttactgact    420
acatgaggat cacccatgaa gtcagtaacc tctggtttgt caactggatc aggaacatca    480
aattgattct ttgcaataat tggttcttca gcttccaatg gttttgattc tccttgaaga    540
ttgactgcct tgacacggaa tgcgtattcc tttccaggaa caagcttatt aaccttggct    600
gtacaatctg ggaaagttcc gacttcctgc catgttccac gagaagtatc catcttctca    660
acaatgtagt gaagaacatc agttcctccg ttatcagttg gaggcttcca gttcaatgta    720
catccttcct tatggatctc gtcaatcttg agtggtcctt ctggagttcc tggtacatca    780
agaacagtaa cattgcactg agcagtatct tttccatgct catttcaac aatgattttg    840 taaactccag tatctccac                                               859
```

<210> SEQ ID NO 72
<211> LENGTH: 545
<212> TYPE: DNA
<213> ORGANISM: Artificial Sequence
<220> FEATURE:
<223> OTHER INFORMATION: chimeric RNAi molecule

<400> SEQUENCE: 72

```
cgatgcagta agtctcgtcg gtgttctcaa caagttgatg aacagaaaga gttgcgttgt     60
agggctcaac gaccgtgtca gagaccttag gcgacggaac aacagagaag gaagacgtaa    120
tgcggtccgg atactcctca cgaatctttg aaatgagcaa agttcccatt ccagagccag    180
ttccaccacc aagcgagtga gtcaattgaa aaccttgaag acaatcacaa ccctcagcct    240
cttttcgaac aacatccagg attgttactg cgaaagcagg caaaacctgg atgttgttcg    300
aaaagaggct gagggttgtg attgtcttca aggttttcaa ttgactcact cgcttggtgg    360
tggaactggc tctggaatgg gaactttgct catttcaaag attcgtgagg agtatccgga    420
ccgcattacg tcttccttct ctgttgttcc gtcgcctaag gtctctgaca cggtcgttga    480
gccctacaac gcaactcttt ctgttcatca acttgttgag aacaccgacg agacttactg    540
catcg                                                              545
```

<210> SEQ ID NO 73

```
<211> LENGTH: 539
<212> TYPE: DNA
<213> ORGANISM: Artificial Sequence
<220> FEATURE:
<223> OTHER INFORMATION: chimeric RNAi molecule

<400> SEQUENCE: 73
aatgcagtag gtctcatcgg tgttctcaac aagctggtgg acggagaggg tggcattgta      60
tggttctaca actgtgtcgg acacctttgg cgatggtaca accgaaatg agctcatgat     120
tctgtctggg tactcttcgc ggattttgga gatgagaagt gttcccattc cagatccggt     180
tcctcctccg agagagtgag tgagttggaa tccttgaaga caatcgcatc cttcggcttc     240
cttgcggatc acgtcggatt gttactgcga aagcaggcaa aaccgacgtg atccgcaagg     300
aagccgaagg atgcgattgt cttcaaggat tccaactcac tcactctctc ggaggaggaa     360
ccggatctgg aatgggaaca cttctcatct ccaaaatccg cgaagagtac ccagacagaa     420
tcatgagctc attctcggtt gtaccatcgc caaaggtgtc cgacacagtt gtagaaccat     480
acaatgccac cctctccgtc caccagcttg ttgagaacac cgatgagacc tactgcatt      539

<210> SEQ ID NO 74
<211> LENGTH: 715
<212> TYPE: DNA
<213> ORGANISM: Artificial Sequence
<220> FEATURE:
<223> OTHER INFORMATION: chimeric RNAi molecule

<400> SEQUENCE: 74
cagttgattt gtctgctgaa aagacggctc ttgcacgtgg agtctatcgg ctgcaatatg      60
tgagagagcg ccgttatcca gcaccaccac cgagtcggca ttctgtgtca atctcctcat     120
ggctaggatg ctgttgtagg gatggacgac gacgtctccg gcattctggg tatccggaaa     180
taccgaatac gtttgtatga tcttcttggg aaatcggtca tttagccttt ccaagaggaa     240
tgagcccaga cctgagcctg tgccaccagc aatcgaatgc agcatcataa agccctcgag     300
tgagtcgctt ccatctgctt ccctatcaat catctccata atgggattgt tactgcgaaa     360
gcaggcaaaa cccattatgg agatgattga tagggaagca gatggaagcg actcactcga     420
gggctttatg atgctgcatt cgattgctgg tggcacaggc tcaggtctgg gctcattcct     480
cttggaaagg ctaaatgacc gatttcccaa gaagatcata caaacgtatt cggtatttcc     540
ggatacccag aatgccggag acgtcgtcgt ccatccctac aacagcatcc tagccatgag     600
gagattgaca cagaatgccg actcggtggt ggtgctggat aacggcgctc tctcacatat     660
tgcagccgat agactccacg tgcaagagcc gtcttttcag cagacaaatc aactg          715

<210> SEQ ID NO 75
<211> LENGTH: 545
<212> TYPE: DNA
<213> ORGANISM: Artificial Sequence
<220> FEATURE:
<223> OTHER INFORMATION: chimeric RNAi molecule

<400> SEQUENCE: 75
cgatacagta ggtttcatcg gtgttttcga cgagctgatg aacggagagg gtggcattgt      60
atggctcgac aactgtgtcg gataccttg tgagggcac aacggagtag gtgttcatga     120
ttctgtctgg gtattcctcg cggattttcg agatcagcaa tgttcccatt cctgatccgg     180
taccacctcc caacgaatga gtcagctgga atccctgtaa gcaatcgcag ctctcggctt     240
cctttctgac tacgtcgagg attgttactg cgaaagcagg caaaacctcg acgtagtcag     300
```

```
aaaggaagcc gagagctgcg attgcttaca gggattccag ctgactcatt cgttgggagg    360
tggtaccgga tcaggaatgg gaacattgct gatctcgaaa atccgcgagg aatacccaga    420
cagaatcatg aacacctact ccgttgtgcc ctcaccaaag gtatccgaca cagttgtcga    480
gccatacaat gccaccctct ccgttcatca gctcgtcgaa acaccgatg aaacctactg     540 tatcg                                                                545

<210> SEQ ID NO 76
<211> LENGTH: 531
<212> TYPE: DNA
<213> ORGANISM: Artificial Sequence
<220> FEATURE:
<223> OTHER INFORMATION: chimeric RNAi molecule

<400> SEQUENCE: 76
cgatgcagta agtctcgtcg gtgttctcaa caagttgatg aacagaaaga gttgcgttgt     60
agggctcaac gaccgtgtca gagaccttag gcgacggaac aacagagaag gaagacgtaa    120
tgcggtccgg atactcctca cgaatctttg aaatgagcaa agttcccatt ccagagccag    180
ttccaccacc aagcgagtga gtcaattgaa aaccttgaag acaatcacaa ccctcagcct    240
cttttcgaac aacatccagc cctgaaaaag gctggatgt tgttcgaaaa gaggctgagg     300
gttgtgattg tcttcaaggt tttcaattga ctcactcgct tggtggtgga actggctctg    360
gaatgggaac tttgctcatt tcaaagattc gtgaggagta tccggaccgc attacgtctt    420
ccttctctgt tgttccgtcg cctaaggtct ctgacacggt cgttgagccc tacaacgcaa    480 ctcttttctgt tcatcaactt gttgagaaca ccgacgagac ttactgcatc g             531

<210> SEQ ID NO 77
<211> LENGTH: 525
<212> TYPE: DNA
<213> ORGANISM: Artificial Sequence
<220> FEATURE:
<223> OTHER INFORMATION: chimeric RNAi molecule

<400> SEQUENCE: 77
aatgcagtag gtctcatcgg tgttctcaac aagctggtgg acggagaggg tggcattgta     60
tggttctaca actgtgtcgg acacctttgg cgatggtaca accgagaatg agctcatgat    120
tctgtctggg tactcttcgc ggattttgga gatgagaagt gttcccattc cagatccggt    180
tcctcctccg agagagtgag tgagttggaa tccttgaaga caatcgcatc cttcggcttc    240
cttgcggatc acgtcgccct gaaaaagggc gacgtgatcc gcaaggaagc cgaaggatgc    300
gattgtcttc aaggattcca actcactcac tctctcggag gaggaaccgg atctggaatg    360
ggaacacttc tcatctccaa aatccgcgaa gagtacccag acagaatcat gagctcattc    420
tcggttgtac catcgccaaa ggtgtccgac acagttgtag aaccatacaa tgccaccctc    480
tccgtccacc agcttgttga gaacaccgat gagacctact gcatt                    525

<210> SEQ ID NO 78
<211> LENGTH: 701
<212> TYPE: DNA
<213> ORGANISM: Artificial Sequence
<220> FEATURE:
<223> OTHER INFORMATION: chimeric RNAi molecule

<400> SEQUENCE: 78
cagttgattt gtctgctgaa aagacggctc ttgcacgtgg agtctatcgg ctgcaatatg     60
```

```
tgagagagcg ccgttatcca gcaccaccac cgagtcggca ttctgtgtca atctcctcat    120
ggctaggatg ctgttgtagg gatggacgac gacgtctccg gcattctggg tatccggaaa    180
taccgaatac gtttgtatga tcttcttggg aaatcggtca tttagccttt ccaagaggaa    240
tgagcccaga cctgagcctg tgccaccagc aatcgaatgc agcatcataa agccctcgag    300
tgagtcgctt ccatctgctt ccctatcaat catctccata atggccctga aaagggcca     360 ttatggagat gattgatagg gaagcagatg gaagcgactc actcgagggc tttatgatgc    420
tgcattcgat tgctggtggc acaggctcag gtctgggctc attcctcttg gaaaggctaa    480
atgaccgatt tcccaagaag atcatacaaa cgtattcggt atttccggat acccagaatg    540
ccggagacgt cgtcgtccat ccctacaaca gcatcctagc catgaggaga ttgacacaga    600
atgccgactc ggtggtggtg ctggataacg gcgctctctc acatattgca gccgatagac    660
tccacgtgca agagccgtct tttcagcaga caaatcaact g                        701

<210> SEQ ID NO 79
<211> LENGTH: 531
<212> TYPE: DNA
<213> ORGANISM: Artificial Sequence
<220> FEATURE:
<223> OTHER INFORMATION: chimeric RNAi molecule

<400> SEQUENCE: 79
cgatacagta ggtttcatcg gtgttttcga cgagctgatg aacggagagg gtggcattgt     60
atggctcgac aactgtgtcg gatacctttg gtgagggcac aacggagtag gtgttcatga    120
ttctgtctgg gtattcctcg cggattttcg agatcagcaa tgttcccatt cctgatccgg    180
taccacctcc caacgaatga gtcagctgga atccctgtaa gcaatcgcag ctctcggctt    240 cctttcgac tacgtcgagc cctgaaaaag ggctcgacgt agtcagaaag gaagccgaga     300
gctgcgattg cttacaggga ttccagctga ctcattcgtt gggaggtggt accggatcag    360
gaatgggaac attgctgatc tcgaaaatcc gcgaggaata cccagacaga atcatgaaca    420
cctactccgt tgtgccctca ccaaaggtat ccgacacagt tgtcgagcca taatgcca      480 ccctctccgt tcatcagctc gtcgaaaaca ccgatgaaac ctactgtatc g              531

<210> SEQ ID NO 80
<211> LENGTH: 535
<212> TYPE: DNA
<213> ORGANISM: Artificial Sequence
<220> FEATURE:
<223> OTHER INFORMATION: chimeric RNAi molecule

<400> SEQUENCE: 80
cgatgcagta agtctcgtcg gtgttctcaa caagttgatg aacagaaaga gttgcgttgt     60
agggctcaac gaccgtgtca gagaccttag gcgacggaac aacagagaag gaagacgtaa    120
tgcggtccgg atactcctca cgaatctttg aaatgagcaa agttcccatt ccagagccag    180
ttccaccacc aagcgagtga gtcaattgaa aaccttgaag acaatcacaa ccctcagcct    240
cttttcgaac aacatccaac atgaggatca cccatgatgg atgttgttcg aaaagaggct    300
gagggttgtg attgtcttca aggttttcaa ttgactcact cgcttggtgg tggaactggc    360
tctggaatgg gaactttgct catttcaaag attcgtgagg agtatccgga ccgcattacg    420
tcttccttct ctgttgttcc gtcgcctaag gtctctgaca cggtcgttga gccctacaac    480
gcaactcttt ctgttcatca acttgttgag aacaccgacg agacttactg catcg         535
```

```
<210> SEQ ID NO 81
<211> LENGTH: 529
<212> TYPE: DNA
<213> ORGANISM: Artificial Sequence
<220> FEATURE:
<223> OTHER INFORMATION: chimeric RNAi molecule

<400> SEQUENCE: 81
aatgcagtag gtctcatcgg tgttctcaac aagctggtgg acggagaggg tggcattgta      60
tggttctaca actgtgtcgg acacctttgg cgatggtaca accgagaatg agctcatgat     120
tctgtctggg tactcttcgc ggattttgga gatgagaagt gttcccattc cagatccggt     180
tcctcctccg agagagtgag tgagttggaa tccttgaaga caatcgcatc cttcggcttc     240
cttgcggatc acgtcacatg aggatcaccc atgagacgtg atccgcaagg aagccgaagg     300
atgcgattgt cttcaaggat tccaactcac tcactctctc ggaggaggaa ccggatctgg     360
aatgggaaca cttctcatct ccaaaatccg cgaagagtac ccagacagaa tcatgagctc     420
attctcggtt gtaccatcgc caaggtgtc cgacacagtt gtagaaccat acaatgccac      480
cctctccgtc caccagcttg ttgagaacac cgatgagacc tactgcatt                 529

<210> SEQ ID NO 82
<211> LENGTH: 705
<212> TYPE: DNA
<213> ORGANISM: Artificial Sequence
<220> FEATURE:
<223> OTHER INFORMATION: chimeric RNAi molecule

<400> SEQUENCE: 82
cagttgattt gtctgctgaa aagacggctc ttgcacgtgg agtctatcgg ctgcaatatg      60
tgagagagcg ccgttatcca gcaccaccac cgagtcggca ttctgtgtca atctcctcat     120
ggctaggatg ctgttgtagg gatggacgac gacgtctccg gcattctggg tatccggaaa     180
taccgaatac gtttgtatga tcttcttggg aaatcggtca tttagccttt ccaagaggaa     240
tgagcccaga cctgagcctg tgccaccagc aatcgaatgc agcatcataa agccctcgag     300
tgagtcgctt ccatctgctt ccctatcaat catctccata atgacatgag gatcacccat     360
gacattatgg agatgattga tagggaagca gatggaagcg actcactcga gggctttatg     420
atgctgcatt cgattgctgg tggcacaggc tcaggtctgg gctcattcct cttggaaagg     480
ctaaatgacc gatttcccaa gaagatcata caaacgtatt cggtatttcc ggatacccag     540
aatgccggag acgtcgtcgt ccatccctac aacagcatcc tagccatgag gagattgaca     600
cagaatgccg actcggtggt ggtgctggat aacggcgctc tctcacatat tgcagccgat     660
agactccacg tgcaagagcc gtcttttcag cagacaaatc aactg                     705

<210> SEQ ID NO 83
<211> LENGTH: 535
<212> TYPE: DNA
<213> ORGANISM: Artificial Sequence
<220> FEATURE:
<223> OTHER INFORMATION: chimeric RNAi molecule

<400> SEQUENCE: 83
cgatacagta ggtttcatcg gtgttttcga cgagctgatg aacggagagg gtggcattgt      60
atggctcgac aactgtgtcg gatacctttg gtgagggcac aacggagtag gtgttcatga     120
ttctgtctgg gtattcctcg cggattttcg agatcagcaa tgttcccatt cctgatccgg     180
taccacctcc caacgaatga gtcagctgga atccctgtaa gcaatcgcag ctctcggctt     240
```

```
cctttctgac tacgtcgaac atgaggatca cccatgatcg acgtagtcag aaaggaagcc    300
gagagctgcg attgcttaca gggattccag ctgactcatt cgttgggagg tggtaccgga    360
tcaggaatgg gaacattgct gatctcgaaa atccgcgagg aatacccaga cagaatcatg    420
aacacctact ccgttgtgcc ctcaccaaag gtatccgaca cagttgtcga gccatacaat    480
gccaccctct ccgttcatca gctcgtcgaa acaccgatg  aaacctactg tatcg         535

<210> SEQ ID NO 84
<211> LENGTH: 869
<212> TYPE: DNA
<213> ORGANISM: Artificial Sequence
<220> FEATURE:
<223> OTHER INFORMATION: chimeric RNAi molecule

<400> SEQUENCE: 84
agtcagtaac ctctggtttg tcaactggat caggaacatc aaattgattc tttgcaataa     60
ttggttcttc agcttccaat ggttttgatt ctccttgaag attgactgcc ttgacacgga    120
atgcgtattc ctttccagga acaagcttat taaccttggc tgtacaatct gggaaagttc    180
cgacttcctg ccatgttcca cgagaagtat ccatcttctc aacaatgtag tgaagaacat    240
cagttcctcc gttatcagtt ggaggcttcc agttcaatgt acatccttcc ttatggatct    300
cgtcaatctt gagtggtcct tctggagttc ctggtacatc aagaacagta acattgcact    360
gagcagtatc ttttccatgc tcattttcaa caatgatttt gtaaactcca gtatctccac    420
ggattgttac tgcgaaagca ggcaaaaccg tggagatact ggagtttaca aaatcattgt    480
tgaaaatgag catggaaaag atactgctca gtgcaatgtt actgttcttg atgtaccagg    540
aactccagaa ggaccactca agattgacga gatccataag gaaggatgta cattgaactg    600
gaagcctcca actgataacg gaggaactga tgttcttcac tacattgttg agaagatgga    660
tacttctcgt ggaacatggc aggaagtcgg aactttccca gattgtacag ccaaggttaa    720
taagcttgtt cctggaaagg aatacgcatt ccgtgtcaag gcagtcaatc ttcaaggaga    780
atcaaaacca ttggaagctg aagaaccaat tattgcaaag aatcaatttg atgttcctga    840
tccagttgac aaaccagagg ttactgact                                      869

<210> SEQ ID NO 85
<211> LENGTH: 855
<212> TYPE: DNA
<213> ORGANISM: Artificial Sequence
<220> FEATURE:
<223> OTHER INFORMATION: chimeric RNAi molecule

<400> SEQUENCE: 85
agtcagtaac ctctggtttg tcaactggat caggaacatc aaattgattc tttgcaataa     60
ttggttcttc agcttccaat ggttttgatt ctccttgaag attgactgcc ttgacacgga    120
atgcgtattc ctttccagga acaagcttat taaccttggc tgtacaatct gggaaagttc    180
cgacttcctg ccatgttcca cgagaagtat ccatcttctc aacaatgtag tgaagaacat    240
cagttcctcc gttatcagtt ggaggcttcc agttcaatgt acatccttcc ttatggatct    300
cgtcaatctt gagtggtcct tctggagttc ctggtacatc aagaacagta acattgcact    360
gagcagtatc ttttccatgc tcattttcaa caatgatttt gtaaactcca gtatctccac    420
gccctgaaaa agggcgtgga gatactggag tttacaaaat cattgttgaa aatgagcatg    480
gaaaagatac tgctcagtgc aatgttactg ttcttgatgt accaggaact ccagaaggac    540
cactcaagat tgacgagatc cataaggaag gatgtacatt gaactggaag cctccaactg    600
```

```
ataacggagg aactgatgtt cttcactaca ttgttgagaa gatggatact tctcgtggaa      660
catggcagga agtcggaact ttcccagatt gtacagccaa ggttaataag cttgttcctg      720
gaaaggaata cgcattccgt gtcaaggcag tcaatcttca aggagaatca aaaccattgg      780
aagctgaaga accaattatt gcaaagaatc aatttgatgt tcctgatcca gttgacaaac      840
cagaggttac tgact                                                      855
```

<210> SEQ ID NO 86
<211> LENGTH: 859
<212> TYPE: DNA
<213> ORGANISM: Artificial Sequence
<220> FEATURE:
<223> OTHER INFORMATION: chimeric RNAi molecule

<400> SEQUENCE: 86

```
agtcagtaac ctctggtttg tcaactggat caggaacatc aaattgattc tttgcaataa       60
ttggttcttc agcttccaat ggttttgatt ctccttgaag attgactgcc ttgacacgga      120
atgcgtattc ctttccagga acaagcttat taaccttggc tgtacaatct gggaaagttc      180
cgacttcctg ccatgttcca cgagaagtat ccatcttctc aacaatgtag tgaagaacat      240
cagttcctcc gttatcagtt ggaggcttcc agttcaatgt acatccttcc ttatggatct      300
cgtcaatctt gagtggtcct tctggagttc ctggtacatc aagaacagta acattgcact      360
gagcagtatc ttttccatgc tcattttcaa caatgatttt gtaaactcca gtatctccac      420
acatgaggat cacccatgag tggagatact ggagtttaca aaatcattgt tgaaaatgag      480
catggaaaag atactgctca gtgcaatgtt actgttcttg atgtaccagg aactccagaa      540
ggaccactca agattgacga gatccataag gaaggatgta cattgaactg gaagcctcca      600
actgataacg gaggaactga tgttcttcac tacattgttg agaagatgga tacttctcgt      660
ggaacatggc aggaagtcgg aactttccca gattgtacag ccaaggttaa taagcttgtt      720
cctggaaagg aatacgcatt ccgtgtcaag gcagtcaatc ttcaaggaga atcaaaacca      780
ttggaagctg aagaaccaat tattgcaaag aatcaatttg atgttcctga tccagttgac      840
aaaccagagg ttactgact                                                  859
```

<210> SEQ ID NO 87
<211> LENGTH: 36
<212> TYPE: PRT
<213> ORGANISM: Bacteriophage lambda

<400> SEQUENCE: 87

```
Met Asp Ala Gln Thr Arg Arg Arg Glu Arg Arg Ala Glu Lys Gln Ala
1               5                   10                  15

Gln Trp Lys Ala Ala Asn Pro Leu Leu Val Gly Val Ser Ala Lys Pro
            20                  25                  30

Val Asn Arg Pro
        35
```

<210> SEQ ID NO 88
<211> LENGTH: 4
<212> TYPE: PRT
<213> ORGANISM: Artificial Sequence
<220> FEATURE:
<223> OTHER INFORMATION: linker polypeptide

<400> SEQUENCE: 88

```
Ile Glu Asp Arg
1
```

-continued

```
<210> SEQ ID NO 89
<211> LENGTH: 6
<212> TYPE: PRT
<213> ORGANISM: Artificial Sequence
<220> FEATURE:
<223> OTHER INFORMATION: linker polypeptide

<400> SEQUENCE: 89

Leu Val Pro Gly Arg Ser
1               5

<210> SEQ ID NO 90
<211> LENGTH: 9
<212> TYPE: PRT
<213> ORGANISM: Artificial Sequence
<220> FEATURE:
<223> OTHER INFORMATION: linker polypeptide

<400> SEQUENCE: 90

Pro Gly Ile Ser Gly Gly Gly Gly Gly
1               5
```

The invention claimed is:

1. A method for delivering a double-stranded RNA molecule to a pest species, comprising co-expressing in a plant cell of:

a) an RNA delivery molecule consisting of a polypeptide sequence comprising i) at least one sequence-specific RNA-binding domain, ii) at least one targeting polypeptide, able to bind to a cellular endocytosis and/or transcytosis receptor molecule, and iii) optionally at least one peptide linker for linking the sequence-specific RNA binding domain (i) to the targeting polypeptide (ii), and b) an RNA molecule which comprises double-stranded RNA comprising annealed complementary strands, one of which has a nucleotide sequence which is complementary to at least part of a target nucleotide sequence of a target gene of a pest species, and which further comprises a nucleotide sequence which specifically binds to the sequence-specific RNA-binding domain of the RNA delivery molecule of (a); and feeding said plant cell to said pest species.

2. The method of claim 1, wherein the nucleotide sequence which binds to the sequence-specific RNA-binding domain of the RNA delivery molecule of (a) is a nucleotide sequence as provided by SEQ ID NO:40.

3. The method of claim 1, wherein the sequence-specific RNA-binding domain of (a)(i) is a polypeptide comprising the bacteriophage MS2 coat protein as represented in SEQ ID NO:14.

4. The method of claim 1, wherein the targeting polypeptide of (a)(ii) is a snowdrop lectin.

* * * * *